(12) United States Patent
Buswell et al.

(10) Patent No.: US 12,691,243 B2
(45) Date of Patent: Jul. 28, 2026

(54) MEDICAL TUBES FOR BREATHING CIRCUIT

(71) Applicant: Fisher & Paykel Healthcare Limited, Auckland (NZ)

(72) Inventors: Matthew Liam Buswell, Auckland (NZ); Gavin Walsh Millar, Auckland (NZ); James William Stanton, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1051 days.

(21) Appl. No.: 16/964,411

(22) PCT Filed: Jan. 24, 2019

(86) PCT No.: PCT/NZ2019/050004
§ 371 (c)(1),
(2) Date: Jul. 23, 2020

(87) PCT Pub. No.: WO2019/147142
PCT Pub. Date: Aug. 1, 2019

(65) Prior Publication Data
US 2021/0046272 A1 Feb. 18, 2021

Related U.S. Application Data

(60) Provisional application No. 62/621,463, filed on Jan. 24, 2018.

(51) Int. Cl.
| | |
|---|---|
| *A61M 16/08* | (2006.01) |
| *A61M 16/10* | (2006.01) |
| *A61M 16/16* | (2006.01) |

(52) U.S. Cl.
CPC .... *A61M 16/0875* (2013.01); *A61M 16/0883* (2014.02); *A61M 16/1095* (2014.02);
(Continued)

(58) Field of Classification Search
CPC .. A61M 16/00; A61M 16/08; A61M 16/0875; A61M 16/0883; A61M 16/109;
(Continued)

(56) References Cited

U.S. PATENT DOCUMENTS

| | | | |
|---|---|---|---|
| 101,959 | A | 4/1870 | Wright |
| 111,975 | A | 2/1871 | Rickard |

(Continued)

FOREIGN PATENT DOCUMENTS

| | | |
|---|---|---|
| AU | 2006320626 | 6/2007 |
| CN | 101396576 | 4/2009 |

(Continued)

OTHER PUBLICATIONS

International Search Report and Written Opinion for International Application No. PCT/NZ2019/050004 mailed May 13, 2019; 26 pages.

(Continued)

*Primary Examiner* — Joseph D. Boecker
(74) *Attorney, Agent, or Firm* — VIA LLP

(57) ABSTRACT
A breathing circuit for use in respiratory therapy includes an inspiratory tube and an expiratory tube. The inspiratory tube of the breathing circuit has a smooth bore. The expiratory tube of the breathing circuit is corrugated. Preferably, the expiratory tube is vapor permeable. Using the combination of a smooth bore inspiratory tube with a corrugated expiratory tube has the unexpected result of improving the performance of the breathing circuit and its components.

19 Claims, 13 Drawing Sheets

(52) U.S. Cl.
CPC ..... *A61M 16/0808* (2013.01); *A61M 16/0833*
(2014.02); *A61M 16/109* (2014.02); *A61M*
*16/16* (2013.01); *A61M 2205/7536* (2013.01);
*A61M 2240/00* (2013.01)

(58) Field of Classification Search
CPC .............. A61M 16/1095; A61M 16/16; A61M
2205/3368
See application file for complete search history.

(56) References Cited

U.S. PATENT DOCUMENTS

| | | | |
|---|---|---|---|
| 111,981 | A | 2/1871 | Sewell |
| 142,018 | A | 8/1873 | Holmes |
| 152,016 | A | 6/1874 | Lana |
| 181,975 | A | 9/1876 | Pedley |
| 181,984 | A | 9/1876 | Rice et al. |
| 242,018 | A | 5/1881 | Miller |
| 281,977 | A | 7/1883 | Coons |
| 2,898,941 | A | 8/1959 | Kilcup |
| 3,307,542 | A | 3/1967 | Andreasen |
| 3,858,615 | A | 1/1975 | Weigl |
| 3,865,106 | A | 2/1975 | Palush |
| 4,007,737 | A | 2/1977 | Paluch |
| 4,265,235 | A * | 5/1981 | Fukunaga ............. A61M 16/08 |
| | | | 128/911 |
| 4,463,755 | A | 8/1984 | Suzuki |
| 4,967,744 | A | 11/1990 | Chua |
| 5,357,948 | A | 10/1994 | Eilentropp |
| 5,404,873 | A | 4/1995 | Leagre et al. |
| 5,501,212 | A | 3/1996 | Psaros |
| 5,735,266 | A | 4/1998 | Smith |
| 5,778,872 | A | 7/1998 | Fukunaga et al. |
| 5,937,856 | A | 8/1999 | Jonasson |
| 6,078,730 | A * | 6/2000 | Huddart ................ A61M 16/08 |
| | | | 219/536 |
| 6,167,883 | B1 | 1/2001 | Beran |
| 6,209,539 | B1 | 4/2001 | Loescher et al. |
| 6,398,197 | B1 | 6/2002 | Dickinson |
| 6,523,538 | B1 | 2/2003 | Wikefeldt |
| 6,536,428 | B1 * | 3/2003 | Smith ................... A61M 16/08 |
| | | | 128/204.17 |
| 6,595,203 | B1 | 7/2003 | Bird |
| 6,598,604 | B1 | 7/2003 | Seakins |
| 8,360,059 | B2 | 1/2013 | Koulechov |
| 8,402,970 | B2 | 3/2013 | Levi |
| 8,944,056 | B2 | 2/2015 | Virr |
| 9,108,227 | B2 | 8/2015 | Frater |
| 9,182,062 | B2 | 11/2015 | Kwok |
| 2001/0054422 | A1 | 12/2001 | Smith et al. |
| 2002/0002976 | A1 | 1/2002 | Smith |
| 2002/0078733 | A1 | 6/2002 | Seakins |
| 2002/0100320 | A1 | 8/2002 | Smith |
| 2002/0124847 | A1 | 9/2002 | Smith |
| 2003/0075176 | A1 | 4/2003 | Fukunaga et al. |
| 2003/0111249 | A1 | 6/2003 | Edirisuriya |
| 2003/0154977 | A1 | 8/2003 | White |
| 2003/0188746 | A1 | 10/2003 | Daugherty |
| 2003/0230306 | A1 | 12/2003 | Castor |
| 2004/0079371 | A1 | 4/2004 | Gray |
| 2004/0081784 | A1 | 4/2004 | Smith |
| 2004/0105848 | A1 | 6/2004 | Ranganathan |
| 2005/0150505 | A1 | 7/2005 | Burrow et al. |
| 2005/0152733 | A1 | 7/2005 | Patel |
| 2007/0125379 | A1 | 6/2007 | Pierro et al. |
| 2008/0251082 | A1 | 10/2008 | Sinha |
| 2008/0276938 | A1 | 11/2008 | Jeppesen |
| 2010/0132706 | A1 | 6/2010 | Nashed |
| 2010/0224195 | A1 | 9/2010 | Henry |
| 2011/0108031 | A1 | 5/2011 | Korneff |
| 2012/0125332 | A1 | 5/2012 | Niland et al. |
| 2012/0125333 | A1* | 5/2012 | Bedford .............. A61M 16/109 |
| | | | 128/205.12 |
| 2012/0152247 | A1 | 6/2012 | Labollita |
| 2012/0266888 | A1 | 10/2012 | Dwyer |

| | | | |
|---|---|---|---|
| 2013/0098360 | A1* | 4/2013 | Hurmez ........... A61M 16/1075 |
| | | | 128/203.12 |
| 2014/0158128 | A1 | 6/2014 | Heimel |
| 2014/0202462 | A1* | 7/2014 | Stoks ................... B29C 53/785 |
| | | | 604/526 |
| 2014/0283829 | A1 | 9/2014 | Miller |
| 2014/0283834 | A1 | 9/2014 | Ahmad et al. |
| 2014/0318535 | A1 | 10/2014 | Bullock |
| 2014/0338666 | A1 | 11/2014 | Visveshwara |
| 2015/0101597 | A1 | 4/2015 | Boucher |
| 2015/0108670 | A1* | 4/2015 | Magee .............. A61M 16/1085 |
| | | | 261/142 |
| 2015/0306333 | A1 | 10/2015 | Amadio et al. |
| 2015/0352308 | A1 | 12/2015 | Cullen |
| 2016/0022949 | A1 | 1/2016 | Milne et al. |
| 2016/0030698 | A1 | 2/2016 | Kolk et al. |
| 2016/0303342 | A1 | 10/2016 | Dwyer et al. |
| 2017/0072156 | A1 | 3/2017 | Nashed |
| 2018/0104436 | A1 | 4/2018 | Leonard et al. |
| 2018/0311459 | A1 | 11/2018 | Winkler et al. |
| 2021/0252248 | A1* | 8/2021 | Stanton ............... A61M 16/109 |

FOREIGN PATENT DOCUMENTS

| | | | |
|---|---|---|---|
| CN | | 202724409 U | 2/2013 |
| CN | | 104955510 | 9/2015 |
| CN | | 105339032 | 2/2016 |
| CN | | 105343971 | 2/2016 |
| EP | | 0579384 A1 | 1/1994 |
| EP | | 0621050 A2 | 10/1994 |
| EP | | 1075849 | 5/2005 |
| EP | | 1621224 | 2/2006 |
| JP | | S63246176 | 10/1988 |
| JP | | H08229129 | 9/1996 |
| JP | | 2009297514 | 12/2009 |
| JP | | 2010046107 | 3/2010 |
| JP | | 2013-514849 | 5/2013 |
| JP | | 2014530737 | 11/2014 |
| JP | | 2015509813 | 4/2015 |
| JP | | 2016-055120 | 4/2016 |
| WO | | 2003022342 A1 | 3/2003 |
| WO | | 2004024429 A1 | 3/2004 |
| WO | | 2006019323 A1 | 2/2006 |
| WO | WO 2011/077250 | | 6/2011 |
| WO | | 2011162622 A1 | 12/2011 |
| WO | WO 2011/149362 | | 12/2011 |
| WO | | 2012033421 A1 | 3/2012 |
| WO | WO 2012/164407 | | 12/2012 |
| WO | WO 2013/055235 | | 4/2013 |
| WO | | 2013137753 A1 | 9/2013 |
| WO | | 2013147623 A1 | 10/2013 |
| WO | | 2013162386 A1 | 10/2013 |
| WO | WO 2014/003579 | | 1/2014 |
| WO | | 2014077706 A1 | 5/2014 |
| WO | WO 2014/088430 | | 6/2014 |
| WO | WO-2014088430 A1 * | | 6/2014 ........ A61M 16/0875 |
| WO | | 2014129911 A1 | 8/2014 |
| WO | | 2014142677 A1 | 9/2014 |
| WO | | 2014142679 A1 | 9/2014 |
| WO | | 2014142682 A1 | 9/2014 |
| WO | | 2015038013 A1 | 3/2015 |
| WO | | 2015038014 A1 | 3/2015 |
| WO | | 2015174859 | 11/2015 |
| WO | | 2016048172 A1 | 3/2016 |
| WO | WO 2016/080847 | | 5/2016 |
| WO | WO 2016/085354 | | 6/2016 |
| WO | WO-2016085354 A1 * | | 6/2016 .......... A61B 5/0813 |
| WO | WO 2018/016975 | | 1/2018 |
| WO | WO 2018/217105 | | 8/2018 |
| WO | WO 2019/147142 | | 8/2019 |

OTHER PUBLICATIONS

International Search Report, PCT/NZ2017/050099, dated Oct. 18, 2017, 10 pages.
International Preliminary Report on Patentability, PCT/NZ2017/050099, dated Jan. 22, 2019, 15 pages.

(56)        References Cited

OTHER PUBLICATIONS

Examination Report received in Chinese Application No. 201980020895.
6, dated Jun. 8, 2024.
Declaration by Gavin Millar, U.S. Appl. No. 16/964,411, dated Jan.
31, 2025, 7 pages.

* cited by examiner

Error in Tidal Volume during Invasive Ventilation by Introducing a 10% Error in Breathing Circuit Compliance ($C_{bs}$)

301

403

601

301

MEDICAL TUBES FOR BREATHING CIRCUIT

INCORPORATION BY REFERENCE

This application is a U.S. National Phase of International Application No. PCT/NZ2019/050004 filed 24 Jan. 2019 which claims priority from U.S. provisional patent application 62/621,463 filed 24 Jan. 2018, the entire contents of which is hereby incorporated by reference in its entirety. This application is a continuation in part of U.S. patent application Ser. No. 16/317,920 filed 15 Jan. 2019 which is a U.S. National Phase of International Application No. PCT/NZ2017/050099 filed 21 Jul. 2017 which claims priority from U.S. provisional patent application 62/365,285 filed 21 Jul. 2016, the entire contents of each is hereby incorporated by reference in its entirety. In addition, the disclosure below references various features of U.S. patent application Ser. No. 13/517,925, published as U.S. Patent Application Publication No. 2013/0098360 A1, U.S. patent application Ser. No. 14/123,485, published as U.S. Patent Application Publication No. 2014/0202462 A1, and U.S. patent application Ser. No. 14/649,801, published as U.S. Patent Application Publication No. 2015/0306333 A1. The entire disclosures of those applications and publications are hereby made part of this specification as if set forth fully herein and incorporated by reference for all purposes, for all that they contain.

BACKGROUND

Field of the Invention

This disclosure relates generally to tubes suitable for medical use, and in particular to medical tubes for use in breathing circuits suitable for providing humidified gases to a patient and/or removing gases from a patient, such as in respiratory humidification systems.

Description of the Related Art

In breathing circuits, various components transport warm and/or humidified gases to and from patients. Respiratory humidification helps reduce the likelihood of infection and/or tissue damage.

SUMMARY

Certain features, aspects, and advantages of the present disclosure recognize a need for improvements that can increase the removal of vapor from expiratory gases in an expiratory tube while increasing the amount of vapor in humidified gases delivered to a patient through an inspiratory tube without increasing the overall resistance to flow in the tubes. Certain features, aspects, and advantages of the present disclosure recognize a need for improvements that reduce the compressible volume of a breathing circuit, or at least reduce the compressible volume of a limb of a breathing circuit. As described herein, there can be a tradeoff with both the compressible volume and resistance to flow between the inspiratory tube and the expiratory tube. There can be a reduction of compressible volume and/or resistance to flow in the inspiratory tube and an increase of compressible volume and/or resistance to flow in the expiratory tube. The reduction of compressible volume in the inspiratory tube can, at least in part, be due to a reduction in the inspiratory tube diameter. The reduction in tube diameter may be allowed by a reduction in resistance to flow which can, at least in part, be due to having a smooth bore. The increase of compressible volume in the expiratory tube can, at least in part, be due to increased surface area of the wall, diameter of the tube, cross-sectional area of the tube, or length of the walls of the expiratory tube. The increase of resistance to flow in the expiratory tube can be due, at least in part, to corrugations. The increased compressible volume and increased resistance to flow in the expiratory tube can improve its permeability due to various factors as described herein. This tradeoff between the inspiratory tube and expiratory tube can maintain the same overall compressible volume and/or resistance to flow in the breathing circuit as a whole.

The lower the compressible volume of a breathing circuit, the lower the pneumatic compliance of the breathing circuit for a fixed extensibility, and the lower the pneumatic compliance of a breathing circuit relative to the patient lung compliance, the less potential there is for error in delivered tidal volume.

A circuit kit for use in respiratory therapy for a patient can include a breathing circuit. The breathing circuit can include an inspiratory tube configured to receive the inspiratory gases flow from a gas source. The inspiratory tube can include an inspiratory inlet, an inspiratory outlet, and an inner wall enclosing an inspiratory central bore. The inner wall of the inspiratory tube can be smooth. The breathing circuit can include an expiratory tube configured to receive an expiratory gases flow from a patient. The expiratory tube can include an expiratory inlet, an expiratory outlet, and an inner wall enclosing an expiratory central bore. The inner wall of the expiratory tube can be corrugated. The inspiratory tube can have an inner diameter between 5 and 14.5 mm. The expiratory tube can have a nominal inner diameter between 15 and 22 mm. The inspiratory tube can have an inner diameter between 4 and 17 mm. The expiratory tube can have a nominal inner diameter between 10.5 and 20.5 mm.

The circuit kit can include a y piece configured for coupling the inspiratory tube and the expiratory tube. The circuit kit can include a chamber for holding a quantity of water and locating on a humidifier. The circuit kit can include a dry line for conveying flow from a ventilator or other gas source to a humidifier inlet. The inspiratory tube can have an inner diameter between 6 mm and 14 mm. The inspiratory tube can have an inner diameter between 6 mm and 13 mm. The inspiratory tube can have an inner diameter between 6 mm and 12 mm. The inspiratory tube can have an inner diameter between 6 mm and 11 mm. The inspiratory tube can have an inner diameter between 7 mm and 10 mm. The inspiratory tube can have an inner diameter between 8 mm and 9 mm. The expiratory tube can have a nominal inner diameter between 15.5 mm and 21 mm. The expiratory tube can have a nominal inner diameter between 16 mm and 20 mm. The expiratory tube can have a nominal inner diameter between 16 mm and 19 mm. The expiratory tube can have a nominal inner diameter between 18 mm and 20 mm. The expiratory tube can have a nominal inner diameter between 19 mm and 20 mm. The inspiratory tube can have an inner diameter between 6 mm and 10 mm. The inspiratory tube can have an inner diameter between 11 mm and 15 mm. The inspiratory tube can have an inner diameter between 9 mm and 13 mm. The inspiratory tube can have an inner diameter between 10 mm and 14 mm. The inspiratory tube can have an inner diameter between 7 mm and 13 mm. The inspiratory tube can have an inner diameter between 8 mm and 14 mm. The expiratory tube can have a nominal inner diameter between 11 mm and 15 mm. The expiratory tube can have a nominal inner diameter a nominal inner diameter between 12 mm and 16 mm. The expiratory tube can have a nominal inner diameter a nominal inner diameter between 14 mm and 18 mm. The expiratory tube can have a nominal inner diameter a nominal inner diameter between 16 mm and 20 mm. The expiratory tube can have a nominal inner diameter a nominal inner diameter between 13 mm and 19 mm. The expiratory tube can have a nominal inner diameter a nominal inner diameter between 14 mm and 20 mm. The inspiratory tube or expiratory tube can have a length between 1.5 m and 2.5 m. The inspiratory tube or expiratory tube can have a length between 1.6 m and 2.5 m. The inspiratory tube can enclose a heating element within the inspiratory central bore or within the wall of the tube. The expiratory tube can include a heating element. The expiratory tube can be breathable. The inner wall of the expiratory tube can be permeable to water vapor and substantially impermeable to liquid and bulk flow of the exhaled gases flowing therethrough. The inspiratory tube can include in longitudinal cross-section a plurality of bubbles each with a flattened surface forming at least part of the wall of the inspiratory central bore. The circuit kit can be suitable for treatment of patients having tidal volumes in the range of 50 ml to 300 ml. The circuit kit can be suitable for treatment of pediatric and adolescent patients. The difference between the inner diameter of the inspiratory tube and the nominal diameter of the expiratory tube can be between 1 mm and 14 mm. The inner diameter of the inspiratory tube can be smaller than the nominal diameter of the expiratory tube by a value between 1 mm and 14 mm. The inspiratory and/or expiratory tube may comprise multiple sections to accommodate other equipment such as a water trap and/or a intermediate connector with one or more sensors, and/or a PCB, and/or a controller. A system can include the circuit kit and a humidifier.

A circuit kit for use in respiratory therapy for a patient can include a breathing circuit. The breathing circuit can include an inspiratory tube configured to receive the inspiratory gases flow from a gas source. The inspiratory tube can include an inspiratory inlet, an inspiratory outlet, and an inner wall enclosing an inspiratory central bore. The inner wall of the inspiratory tube can be smooth. The breathing circuit can include an expiratory tube configured to receive an expiratory gases flow from a patient. The expiratory tube can include an expiratory inlet, an expiratory outlet, and an inner wall enclosing an expiratory central bore. The inner wall of the expiratory tube can be corrugated. The inspiratory tube can have an inner diameter from between 10 and 21 mm. The expiratory tube can have a nominal inner diameter from between 22 and 30 mm. The inspiratory tube can have an inner diameter between 9.5 and 24 mm. The expiratory tube can have a nominal inner diameter between 19 and 31.5 mm.

The circuit kit can include a y piece configured for coupling the inspiratory tube and the expiratory tube. The circuit kit can include a chamber for holding a quantity of water and locating on a humidifier. The circuit kit can include a dry line for conveying flow from a ventilator or other gas source to a humidifier outlet. The inspiratory tube can have an inner diameter between 10 mm and 20 mm. The inspiratory tube can have an inner diameter between 11 mm and 20 mm. The inspiratory tube can have an inner diameter between 11 mm and 19 mm. The inspiratory tube can have an inner diameter between 11 mm and 18 mm. The inspiratory tube can have an inner diameter between 11 mm and 17 mm. The inspiratory tube can have an inner diameter between 11 mm and 16 mm. The inspiratory tube can have an inner diameter between 11 mm and 15 mm. The inspiratory tube can have an inner diameter between 12 mm and 15 mm. The inspiratory tube can have an inner diameter between 13 mm and 14 mm. The expiratory tube can have a nominal inner diameter between 22 mm and 29 mm. The expiratory tube can have a nominal inner diameter between 23 mm and 30 mm. The expiratory tube can have a nominal inner diameter between 24 mm and 30 mm. The expiratory tube can have a nominal inner diameter between 24 mm and 29 mm. The expiratory tube can have a nominal inner diameter between 25 mm and 28 mm. The expiratory tube can have a nominal inner diameter between 25.5 mm and 27 mm. The inspiratory tube can have an inner diameter between 11 mm and 15 mm. The inspiratory tube can have an inner diameter between 12 mm and 16 mm. The inspiratory tube can have an inner diameter between 18 mm and 22 mm. The inspiratory tube can have an inner diameter between 19 mm and 23 mm. The inspiratory tube can have an inner diameter between 10 mm and 16 mm. The inspiratory tube can have an inner diameter between 17 mm and 23 mm. The expiratory tube can have a nominal inner diameter between 25 mm and 29 mm. The expiratory tube can have a nominal inner diameter between 26 mm and 30 mm. The expiratory tube can have a nominal inner diameter between 20 mm and 24 mm. The expiratory tube can have a nominal inner diameter between 21 mm and 25 mm. The expiratory tube can have a nominal inner diameter between 24 mm and 30 mm. The expiratory tube can have a nominal inner diameter between 20 mm and 26 mm. The inspiratory tube or expiratory tube can have a length between 1.5 m and 2.5 m. The inspiratory tube or expiratory tube can have a length between 1.6 m and 2.5 m. The inspiratory tube can enclose a heating element within the inspiratory central bore or within the wall of the tube. The expiratory tube can include a heating element. The expiratory tube can be breathable. The inner wall of the expiratory tube can be permeable to water vapor and substantially impermeable to liquid and bulk flow of the exhaled gases flowing therethrough. The inspiratory tube can include in longitudinal cross-section a plurality of bubbles each with a flattened surface forming at least part of the wall of the inspiratory central bore. The circuit kit can be suitable for treatment of patients having tidal volumes greater than 300 ml. The circuit kit can be suitable for treatment of adult patients. The difference between the inner diameter of the inspiratory tube and the nominal diameter of the expiratory tube can be between 1 mm and 20 mm. The inner diameter of the inspiratory tube can be smaller than the nominal diameter of the expiratory tube by a value between 1 mm and 20 mm. The inspiratory and/or expiratory tube may comprise multiple sections to accommodate other equipment such as a water trap and/or a intermediate connector with one or more sensors, and/or a PCB, and/or a controller. A system can include the circuit kit and a humidifier.

A circuit kit for use in respiratory therapy for a patient can include a breathing circuit. The breathing circuit can include an inspiratory tube configured to receive the inspiratory gases flow from a gas source. The inspiratory tube can include an inspiratory inlet, an inspiratory outlet, and an inner wall enclosing an inspiratory central bore. The inner wall of the inspiratory tube can be smooth. The breathing circuit can include an expiratory tube configured to receive an expiratory gases flow from a patient. The expiratory tube can include an expiratory inlet, an expiratory outlet, and an inner wall enclosing an expiratory central bore. The inner wall of the expiratory tube can be corrugated. The inspiratory tube can have an inner diameter from between 4 and 12 mm. The expiratory tube can have a nominal inner diameter from between 13 and 18 mm. The inspiratory tube can have an inner diameter from between 3 and 13 mm. The expiratory tube can have a nominal inner diameter from between 9.5 and 19 mm.

The circuit kit can include a y piece configured for coupling the inspiratory tube and the expiratory tube. The circuit kit can include a chamber for holding a quantity of water and locating on a humidifier. The circuit kit can include a dry line for conveying flow from a ventilator to other gas source to a humidifier inlet. The inspiratory tube can have an inner diameter between 5 mm and 11 mm. The inspiratory tube can have an inner diameter between 6 mm and 10 mm. The inspiratory tube can have an inner diameter between 6 mm and 8 mm. The inspiratory tube can have an inner diameter between 9 mm and 10 mm. The expiratory tube can have a nominal inner diameter between 13 mm and 17 mm. The expiratory tube can have a nominal inner diameter between 14 mm and 17 mm. The expiratory tube can have a nominal inner diameter between 15 mm and 16.5 mm. The expiratory tube can have a nominal inner diameter between 14 mm and 15 mm. The inspiratory tube or expiratory tube can have a length between 1.5 m and 2.5 m. The inspiratory tube or expiratory tube can have a length between 1.6 m and 2.5 m. The inspiratory tube can have an inner diameter between 5 mm and 9 mm. The inspiratory tube can have an inner diameter between 6 mm and 10 mm. The inspiratory tube can have an inner diameter between 7 mm and 11 mm. The inspiratory tube can have an inner diameter between 8 mm and 12 mm. The inspiratory tube can have an inner diameter between 4 mm and 11 mm. The inspiratory tube can have an inner diameter between 6 mm and 12 mm. The expiratory tube can have a nominal inner diameter between 13 mm and 17 mm. The expiratory tube can have a nominal inner diameter between 12 mm and 16 mm. The expiratory tube can have a nominal inner diameter between 11 mm and 15 mm. The expiratory tube can have a nominal inner diameter between 14 mm and 18 mm. The expiratory tube can have a nominal inner diameter between 12 mm and 18 mm. The expiratory tube can have a nominal inner diameter between 10 mm and 16 mm. The inspiratory tube can enclose a heating element within the inspiratory central bore or within the wall of the tube. The expiratory tube can include a heating element. The expiratory tube can be breathable. The inner wall of the expiratory tube can be permeable to water vapor and substantially impermeable to liquid and bulk flow of the exhaled gases flowing therethrough. The inspiratory tube can include in longitudinal cross-section a plurality of bubbles each with a flattened surface forming at least part of the wall of the inspiratory central bore. The circuit kit can be suitable for treatment of patients having tidal volumes less than or equal to 50 ml. The circuit kit can be suitable for treatment of neonatal patients. The difference between the inner diameter of the inspiratory tube and the nominal diameter of the expiratory tube can be between 1 mm and 14 mm. The inner diameter of the inspiratory tube can be smaller than the nominal diameter of the expiratory tube by a value between 1 mm and 14 mm. The inspiratory and/or expiratory tube may comprise multiple sections to accommodate other equipment such as a water trap and/or a intermediate connector with one or more sensors, and/or a PCB, and/or a controller. A system can include the circuit kit and a humidifier.

A circuit kit for use in respiratory therapy for a patient can be provided. The breathing circuit can include an inspiratory tube configured to receive the inspiratory gases flow from a gas source. The inspiratory tube can include an inspiratory inlet, an inspiratory outlet, and an inner wall enclosing an inspiratory central bore. The inner wall of the inspiratory tube can be smooth. The breathing circuit can include an expiratory tube configured to receive an expiratory gases flow from a patient. The expiratory tube can include an expiratory inlet, an expiratory outlet, and an inner wall enclosing an expiratory central bore. The inner wall of the expiratory tube can corrugated.

In some embodiments, the inspiratory tube can have an inner diameter between 3 mm and 11 mm and the expiratory tube can have a nominal inner diameter between 8 mm and 16 mm. The inspiratory tube can have an inner diameter between 4 mm and 8 mm. The expiratory tube can have a nominal inner diameter between 11 mm and 15 mm. The inspiratory tube can have an inner diameter between 6 mm and 10 mm. The expiratory tube can have a nominal inner diameter between 10 mm and 14 mm. The inspiratory tube or expiratory tube can have a length between 1.5 m and 2.5 m. In some embodiments, the inspiratory tube can have an inner diameter between 5 mm and 13 mm and the expiratory tube can have a nominal inner diameter between 15 mm and 23 mm. The inspiratory tube can have an inner diameter between 5 mm and 9 mm. The expiratory tube can have a nominal inner diameter between 18 mm and 22 mm. The inspiratory tube can have an inner diameter between 8 mm and 12 mm. The expiratory tube can have a nominal inner diameter between 16 mm and 20 mm. The inspiratory tube or expiratory tube can have a length between 1.5 m and 2.5 m. In some embodiments, the inspiratory tube can have an inner diameter between 10 mm and 18 mm and the expiratory tube can have a nominal inner diameter between 24 mm and 32 mm. The inspiratory tube can have an inner diameter between 9 mm and 13 mm. The expiratory tube can have a nominal inner diameter between 27 mm and 31 mm. The inspiratory tube can have an inner diameter between 15 mm and 19 mm. The expiratory tube can have a nominal inner diameter between 24 mm and 28 mm. The inspiratory tube or expiratory tube can have a length between 1.5 m and 2.5 m. The inspiratory tube can have an inner diameter and a length. The expiratory tube can have a nominal inner diameter and a length. In some embodiments, the circuit kit is suitable for treatment of adult patients. In some embodiments, the circuit kit is suitable for treatment of pediatric and adolescent patients. In some embodiments, the circuit kit is suitable for treatment of pediatric and neonatal patients.

A breathing circuit can include an inspiratory limb for carrying inspiratory gases to a patient. The inspiratory limb can include a first elongate member comprising a hollow body spirally wound to form at least in part a first elongate tube having a longitudinal axis, a first lumen extending along the longitudinal axis, and a hollow wall surrounding the lumen. The inspiratory limb can include a second elongate member spirally wound and joined between adjacent turns of the first elongate member, the second elongate member forming at least a portion of the lumen of the first elongate tube. The breathing circuit can include an expiratory limb for carrying exhaled gases from the patient. The expiratory limb can include an inlet and an outlet. The expiratory limb can include a third elongate member comprising a second tube enclosing a second lumen. The second lumen can be configured to contain a bulk flow of the exhaled gases and the second tube is permeable to water vapor and substantially impermeable to liquid water and bulk flow of the exhaled gases.

The wall of the expiratory tube can comprise a foamed or unfoamed polymer that is permeable to water vapor and substantially impermeable to liquid water and bulk flow of the exhaled gases. The foamed polymer can comprise a solid thermoplastic elastomer material having cell voids distributed throughout. The unfoamed polymer may comprise an extruded solid thermoplastic elastomer material that is permeable to water vapor and substantially impermeable to liquid water and bulk flow of the exhaled gases. The first lumen of the inspiratory limb can have a smooth bore. The second elongate member of the inspiratory limb can enclose at least one heating element. The first elongate member of the inspiratory limb can form in longitudinal cross-section a plurality of bubbles with a flattened surface at the lumen. The second elongate member of the inspiratory limb can enclose at least one heating element, and wherein the at least one inspiratory heating element is between a bubble of the plurality of bubbles and the inspiratory central bore. The third elongate member of the expiratory limb can be corrugated. The first elongate tube can enclose a heating element within its lumen. The third elongate member of the expiratory limb can enclose a heating element within the second lumen. The third elongate member of the expiratory limb can comprise a heating element attached to the inner wall of the second tube. The third elongate member of the expiratory limb can comprise a heating element embedded in the wall of the second tube. The second tube can have an inner surface adjacent to the second lumen and the expiratory limb further comprises a plurality of reinforcing ribs circumferentially arranged around the inner surface and generally longitudinally aligned between the inlet and the outlet.

A device can include a breathing circuit. The breathing circuit can include an inspiratory tube configured to receive the inspiratory gases flow from a gas source, the inspiratory tube comprising an inspiratory inlet, an inspiratory outlet, and a wall enclosing an inspiratory central bore. The inner wall of the inspiratory tube can be smooth. The breathing circuit can include an expiratory tube configured to receive an expiratory gases flow from a patient. The expiratory tube can include an expiratory inlet, an expiratory outlet, and a wall enclosing an expiratory central bore. The inner wall of the expiratory tube can be corrugated. The wall of the expiratory tube can be permeable to water vapor and substantially impermeable to liquid and bulk flow of the exhaled gases flowing therethrough.

The wall of the expiratory tube can comprise a foamed or unfoamed polymer that is permeable to water vapor and substantially impermeable to liquid water and bulk flow of the exhaled gases. The inspiratory tube can enclose a heating element within its central bore. The inspiratory tube can comprise a heating element attached to its wall. The inspiratory tube can comprise a heating element embedded in its wall. The expiratory tube can comprise a heating element within its central bore. The expiratory tube can comprise a heating element attached to its inner wall. The expiratory tube can comprise a heating embedded within its inner wall. The inspiratory tube can comprise in longitudinal cross-section a plurality of bubbles with a flattened surface at the lumen. The inspiratory tube can comprise at least one heating element, wherein the at least one inspiratory heating element is between a bubble of the plurality of bubbles and the inspiratory central bore. The expiratory tube can comprise a plurality of reinforcing ribs circumferentially arranged around the inner surface and generally longitudinally aligned between the inlet and the outlet. The breathing circuit can include a humidifier configured to humidify inspiratory gases flow to a patient. The humidifier can include a humidification chamber configured to store a volume of liquid and configured to be in fluid communication with the inspiratory gases flow. The humidifier can include a heater configured to heat the volume of liquid in the humidification chamber to create vapor, such that the inspiratory gases flow is humidified by the vapor.

A respiratory apparatus can include a humidifier configured to humidify an inspiratory gases flow to a patient. The respiratory apparatus can include an inspiratory tube configured to receive the inspiratory gases flow from the humidifier. The inspiratory tube can include an inspiratory inlet, an inspiratory outlet, and a wall enclosing an inspiratory central bore. The inner wall of the inspiratory tube can be smooth. The respiratory apparatus can include an expiratory tube configured to receive an expiratory gases flow from the patient. The expiratory tube can include an expiratory inlet, an expiratory outlet, and a wall enclosing an expiratory central bore. The expiratory central bore can be corrugated. The wall of the expiratory tube can be permeable to water vapor and substantially impermeable to liquid and bulk flow of the exhaled gases flowing therethrough.

The inspiratory tube can comprise at least one heating element within its central bore. The inspiratory tube can comprise at least one heating element attached to its inner wall. The inspiratory tube can comprise at least one heating element enclosed within its wall. The expiratory tube can comprise at least one heating element within the expiratory central bore. The expiratory tube can comprise at least one heating element attached to its inner wall. The expiratory tube can comprise at least one heating element embedded within its inner wall. The inspiratory tube can comprise a spirally wound member that forms in longitudinal cross-section a plurality of bubbles with a flattened surface at the inspiratory central bore. The inspiratory tube can enclose at least one heating element, and the at least one inspiratory heating element can be between a bubble of the plurality of bubbles and the inspiratory central bore. The wall of the expiratory tube can comprise a foamed polymer.

A respiratory apparatus can include a humidifier configured to humidify an inspiratory gases flow to a patient. The humidifier can include a humidification chamber configured to store a volume of liquid and configured to be fluid communication with the inspiratory gases flow. The humidifier can include a heater configured to heat the volume of liquid in the humidification chamber to create vapor, such that the inspiratory gases flow is humidified by the vapor. The respiratory apparatus can include an inspiratory tube configured to receive the humidified inspiratory gases flow from the humidifier. The inspiratory tube can include a wall enclosing an inspiratory central bore. The inspiratory central bore of the inspiratory tube can be smooth. The inspiratory tube can include a spirally wound first elongate member that forms in longitudinal cross-section a plurality of bubbles with a flattened surface at the inspiratory central bore. The bubbles can be configured to insulate the inspiratory central bore. The inspiratory tube can include a spirally wound second elongate member joined between adjacent turns of the first elongate member, the second elongate member forming at least a portion of the lumen of the first elongate tube and comprising at least one inspiratory heating element embedded within the second elongate member. The respiratory apparatus can include an expiratory tube configured to receive an expiratory gases flow from the patient. The expiratory tube can include a conduit enclosing an expiratory central bore. The expiratory central bore can be corrugated. The conduit can be permeable to water vapor and substantially impermeable to liquid flow therethrough. The expiratory tube can include at least one expiratory heating element within the expiratory central bore. The respiratory apparatus can include a control system configured to deliver power to the heater of the humidifier, the at least one inspiratory heating element, and the at least one expiratory heating element.

The wall of the expiratory tube can comprise a foamed or unfoamed polymer that is permeable to water vapor and substantially impermeable to liquid water and bulk flow of the exhaled gases. The foamed polymer can comprise a solid thermoplastic elastomer material having cell voids distributed throughout. The unfoamed polymer can comprise an extruded solid thermoplastic elastomer material that is permeable to water vapor and substantially impermeable to liquid water and bulk flow of the exhaled gases. The at least one inspiratory heating element can be between a bubble of the plurality of bubbles and the inspiratory central bore. The respiratory apparatus can include a patient interface assembly between the inspiratory tube and the expiratory tube. The power delivered by the control system can be calculated to provide increased humidification by the humidifier and controlled condensate management by the at least one expiratory heating element and the at least one inspiratory heating element. The respiratory apparatus can include a ventilator configured to provide the inspiratory gases flow and receive the expiratory gases flow. The ventilator can be configured to provide a pulsatile inspiratory gases flow to the humidifier. The ventilator can be configured to provide a constant inspiratory gases flow to the humidifier. The ventilator can be configured to provide a bias flow of gases.

A respiratory apparatus can include a humidifier configured to humidify an inspiratory gases flow to a patient. The respiratory apparatus can include an inspiratory tube configured to receive the inspiratory gases flow from a gas source. The inspiratory tube can include an inspiratory inlet, an inspiratory outlet, and a wall enclosing an inspiratory central bore. The inner wall of the inspiratory tube can be smooth. The respiratory apparatus can include an expiratory tube configured to receive an expiratory gases flow from a patient. The expiratory tube can include an expiratory inlet, an expiratory outlet, and a wall enclosing an expiratory central bore. The inner wall of the expiratory tube can be corrugated. The wall of the expiratory tube can be permeable to water vapor and substantially impermeable to liquid and bulk flow of the exhaled gases flowing therethrough.

The wall of the expiratory tube can comprise a foamed or unfoamed polymer that is permeable to water vapor and substantially impermeable to liquid water and bulk flow of the exhaled gases. The inspiratory tube can comprise at least one heating element within its central bore. The inspiratory tube can comprise at least one heating element attached to its inner wall. The inspiratory tube can comprise at least one heating element enclosed within its wall. The first elongate member of the inspiratory limb can form in longitudinal cross-section a plurality of bubbles with a flattened surface at the lumen. The inspiratory tube can enclose at least one heating element, and the at least one inspiratory heating element can be between a bubble of the plurality of bubbles and the inspiratory central bore. The expiratory tube can comprise at least one heating element within the expiratory central bore. The expiratory tube can comprise at least one heating element attached to its inner wall. The expiratory tube can comprise at least one heating element embedded within its inner wall. The expiratory tube can comprise a plurality of reinforcing ribs circumferentially arranged around the inner surface and generally longitudinally aligned between the inlet and the outlet. The respiratory apparatus can comprise a control system configured to deliver power to the heater of the humidifier and the at least one heating element.

A breathing circuit can comprise the combination of a smooth bore inspiratory tube with a corrugated, vapor permeable expiratory tube to increase the vapor in humidified gases delivered to a patient via the inspiratory limb of the circuit and increase the removal of vapor from expiratory gases in the expiratory limb of the circuit without increasing the overall resistance to flow of the tubes, thus avoiding increase of the pressure drop in the breathing circuit. The smooth bore inspiratory tube can provide an opportunity for a tradeoff. The smooth bore can reduce the resistance to flow, which can allow for a reduction in the diameter or cross-sectional area of the inspiratory tube while maintaining an acceptable resistance to flow. This reduction in diameter or cross-sectional area of the inspiratory tube reduces the compressible volume of the inspiratory tube. The smaller diameter inspiratory tube can reduce the compressible volume of at least a portion of the breathing circuit which reduces the potential for error in delivered tidal volume. A ventilator typically intends to deliver a set volume of gas to the patient (a 'tidal volume') for each breath. Reducing the error in delivered tidal volume can ensure that the patient is receiving the correct gas volume.

Using the combination of a smooth bore inspiratory tube with a corrugated expiratory tube has an unforeseen synergistic effect that improves performance of the breathing circuit and its components beyond expectations. Using a smooth bore inspiratory tube with a smaller internal diameter than a comparable corrugated tube can decrease the compressible volume of the tube. This decrease in compressible volume can ensure the proper volume of gas is delivered to a patient. As described herein, the inspiratory tube with a smaller internal diameter can reduce the overall compressible volume and pneumatic compliance of the breathing circuit. As described herein, the inspiratory tube with a smaller internal diameter can have a reduced compressible volume which can be a tradeoff for an increased compressible volume of the expiratory tube.

Due to practical reasons, the breathing circuit tubing compressible volume and therefore compliance is usually much larger than the patient's lungs. Factors impacting the breathing circuit tubing compressible volume include minimizing resistance to gas flow of the tubing and enabling the tubes to be long enough to manage the patient in the bed space. This is made worse by some lung disease states leading to patients with very stiff, low compliance lungs. Additionally, a low compressible volume due to decrease in length (e.g. a shortened tube) is directly at odds with both usability and breathable expiratory limbs. In practice, long tubes are generally better, such as to enable freedom of movement and positioning of the patient. In practice, higher surface area is generally better in the expiratory limb to increase breathability of the expiratory limbs.

There are potential tradeoffs between components of the breathing circuit in order to maintain a sufficiently low compressible volume. The diameter or cross-sectional area of the inspiratory tube can be reduced. However, decreasing the internal diameter of the inspiratory tube also increases resistance to flow (RTF) in the inspiratory tube. It was discovered that making the interior bore of the inspiratory tube smooth can compensate for this increase in RTF, because a smooth bore decreases RTF compared to a tube with a corrugated bore or another type of non-smooth bore. The use of a smooth bore also has the added benefit of reducing trapping of vapor and condensates. It was also discovered that, if the increased RTF resulting from decreasing the tube's internal diameter is outweighed by the decrease in RTF resulting from using a smooth bore, then there is a net decrease in RTF in the breathing circuit or at least net decrease in RTF in the inspiratory tube. The smooth bore of the inspiratory tube lowers the RTF which allows for the reduction of the diameter of the inspiratory tube which would normally increase the RTF, wherein the smoothness of the bore and the reduction in diameter can be balanced. As described herein the reduction in the diameter or cross-sectional area can reduce the compressible volume. This lowering of the compressible volume of the inspiratory tube can offset an increase of the compressible volume of the expiratory tube, such as by increasing the diameter or cross-sectional area of the expiratory tube. Increasing the diameter or cross-sectional area of expiratory tube creates a greater surface area of the expiratory tube, which increases the vapor permeability of the expiratory tube.

Certain features, aspects, and advantages of the inventive realization related to the compressible volume of the components of the breathing circuit feature a combination of one or more of the following: the decrease of the internal diameter of the inspiratory tube, the smooth bore of the inspiratory tube, the reduced compressible volume of the inspiratory tube, the increase of the compressible volume of the expiratory tube, the increase of the diameter of the expiratory tube, the increase of the surface area of the expiratory tube, and/or the increase of the vapor permeability of the expiratory tube. Certain features, aspects, and advantages of the present disclosure reflect the inventive realization that this net decrease in RTF, due to the smooth bore inspiratory tube, allows for other components of the circuit to be modified without changing the overall compressible volume, overall RTF, and/or overall pressure drop, for the circuit as a whole. The use of a smooth bore inspiratory tube can permit the use of a longer corrugated expiratory tube, which would otherwise increase RTF in the circuit. The increased length of the expiratory tube improves the ability of the tube to remove vapor from expiratory gases, due at least in part to increased residence time. The increased diameter of the expiratory tube can improve the ability of the tube to remove vapor from expiratory gases, due to the increased wall surface area through which vapor permeates. When the use of the smooth bore inspiratory tube decreases the RTF of the circuit as a whole, the increase in RTF resulting from increasing the length of the expiratory tube may not result in a net increase in RTF, a net increase in compressible volume, and/or a corresponding pressure drop, in the overall circuit. For instance, based on the design, the increased length of the expiratory tube and the decreased diameter of the smooth bore inspiratory tube can be net neutral regarding RTF.

The use of a smooth bore inspiratory tube in a breathing circuit instead of a corrugated, or similarly non-smooth wall tube, may be combined with the use of a wider (larger cross-sectional area or diameter) expiratory tube in the breathing circuit, which decreases RTF. The tradeoff may not be in RTF, which in this case decreases in both tubes. The smooth bore decreases RTF compared to a tube with a corrugated bore or another type of non-smooth bore. The decrease in RTF in the inspiratory tube may, however, be offset by a decrease in diameter or cross-sectional area increasing RTF. The larger cross-sectional area or diameter expiratory tube also decreases RTF. Instead, there can be a tradeoff of compressible volume due to change in diameter or cross-sectional area of the inspiratory tube and the expiratory tube, which decreases in the inspiratory tube but increases in the expiratory tube. The smaller diameter inspiratory tube has a smaller compressible volume. The larger diameter expiratory tube has a larger compressible volume.

A breathing circuit can comprise an inspiratory limb for carrying inspiratory gases to a patient. The inspiratory limb comprises a first elongate member comprising a hollow body spirally wound to form at least in part a first elongate tube having a longitudinal axis, a first lumen extending along the longitudinal axis, and a hollow wall surrounding the lumen. The inspiratory limb further comprises a second elongate member spirally wound and joined between adjacent turns of the first elongate member, the second elongate member forming at least a portion of an inner wall of the lumen of the first elongate tube. The breathing circuit further comprises an expiratory limb for carrying exhaled gases from the patient. The expiratory limb comprises an inlet, an outlet, and a third elongate member comprising a second tube enclosing a second lumen. The second lumen is configured to contain a bulk flow of the exhaled gases and the second tube is permeable to water vapor and substantially impermeable to liquid water and bulk flow of the exhaled gases.

The foregoing breathing circuit can also have one, some, or all of the following properties, as well as any property or properties described in this disclosure. The wall of the expiratory tube can comprise a foamed or unfoamed polymer that is permeable to water vapor and substantially impermeable to liquid water and bulk flow of the exhaled gases. For purposes of this disclosure, any material described as "permeable to water vapor and substantially impermeable to liquid water and bulk flow of gases" (or substantially similar language) is defined herein as a material that allows water vapor molecules to pass through by diffusion, facilitated diffusion, passive transport, active transport, or another similar mechanism for selectively transporting water vapor molecules, but does not have leak paths from one outer major surface of the material to another outer major surface of the material that allow passage of liquid water or bulk flow of gas through the leak paths.

The foamed polymer can comprise a solid thermoplastic elastomer material having cell voids distributed throughout. The unfoamed polymer can comprise a solid thermoplastic elastomer material that is permeable to water vapor and substantially impermeable to liquid water and bulk flow of the exhaled gases. The first lumen of the inspiratory limb can have a smooth bore. The second elongate member of the inspiratory limb can enclose at least one heating element. The first elongate member of the inspiratory limb may form in longitudinal cross-section a plurality of bubbles with a flattened surface at the lumen. The second elongate member of the inspiratory limb can further comprise at least one heating element, and the at least one inspiratory heating element can be positioned between a bubble of the plurality of bubbles and the inspiratory central bore. The third elongate member of the expiratory limb can be corrugated. The first elongate tube can enclose a heating element within its lumen. The third elongate member of the expiratory limb can enclose a heating element within the second lumen. The third elongate member of the expiratory limb can comprise a heating element attached to the inner wall of the second tube. The third elongate member of the expiratory limb can comprise a heating element embedded in the wall of the second tube. The second tube can have an inner surface adjacent to the second lumen and the expiratory limb can further comprise a plurality of reinforcing ribs circumferentially arranged around the inner surface and generally longitudinally aligned between the inlet and the outlet. The foamed polymer is desirably selected or manufactured such that the solid thermoplastic elastomer material selectively transports water vapor molecules but the cell voids distributed throughout do not form leak paths allowing passage of liquid water or bulk flow of gas through the leak paths.

A device can comprise a breathing circuit. The breathing circuit further comprises an inspiratory tube configured to receive the inspiratory gases flow from a gas source. The inspiratory tube comprises an inspiratory inlet, an inspiratory outlet, and a wall enclosing an inspiratory central bore, wherein the inner wall of the inspiratory tube is smooth. The breathing circuit further comprises an expiratory tube configured to receive an expiratory gases flow from a patient. The expiratory tube comprises an expiratory inlet, an expiratory outlet, and a wall enclosing an expiratory central bore. The inner wall of the expiratory tube is corrugated, and the wall of the expiratory tube is permeable to water vapor and substantially impermeable to liquid and gases flowing therethrough.

The foregoing device can also have one, some, or all of the following properties, as well as any property or properties described in this disclosure. The wall of the expiratory tube can comprise a foamed polymer that is permeable to water vapor and substantially impermeable to liquid water and bulk flow of the exhaled gases. The inspiratory tube can enclose a heating element within its central bore or within the wall of the tube. The inspiratory tube can comprise a heating element attached to its wall. The inspiratory tube can comprise a heating element embedded in its wall. The expiratory tube can comprise a heating element within its central bore. The expiratory tube can comprise a heating element attached to its inner wall. The expiratory tube can comprise a heating element embedded within its inner wall. The inspiratory tube can comprise in longitudinal cross-section a plurality of bubbles with a flattened surface at the lumen. The inspiratory tube can comprise at least one heating element, and the at least one inspiratory heating element can be positioned between a bubble of the plurality of bubbles and the inspiratory central bore.

Further, the expiratory tube can comprise a plurality of reinforcing ribs circumferentially arranged around the inner surface and generally longitudinally aligned between the inlet and the outlet. The breathing circuit can further comprise a humidifier configured to humidify inspiratory gases flow to be delivered to a patient. The humidifier can comprise a humidification chamber configured to store a volume of liquid and configured to be in fluid communication with the inspiratory gases flow, and a heater configured to heat the volume of liquid in the humidification chamber to create vapor such that the inspiratory gases flow is humidified by the vapor.

A respiratory apparatus can comprise a humidifier, an inspiratory tube, and an expiratory tube. The humidifier is configured to humidify an inspiratory gases flow to a patient. The inspiratory tube is configured to receive the inspiratory gases flow from the humidifier. The inspiratory tube comprises an inspiratory inlet, an inspiratory outlet, and a wall enclosing an inspiratory central bore, wherein the inner wall of the inspiratory tube is smooth. The expiratory tube is configured to receive expiratory gases flow from the patient. The expiratory tube comprises an expiratory inlet, an expiratory outlet, and a wall enclosing an expiratory central bore, wherein the expiratory central bore is corrugated, and wherein the wall of the expiratory tube is permeable to water vapor and substantially impermeable to liquid and bulk flow of the exhaled gases flowing therethrough.

The foregoing respiratory apparatus can also have one, some, or all of the following properties, as well as any property or properties described in this disclosure. The inspiratory tube can comprise at least one heating element within its central bore. The inspiratory tube can comprise at least one heating element attached to its inner wall. The inspiratory tube can comprise at least one heating element enclosed or embedded within its wall. The expiratory tube can comprises at least one heating element within the expiratory central bore. The expiratory tube can comprise at least one heating element attached to its inner wall. The expiratory tube can comprise at least one heating element embedded within its inner wall. The inspiratory tube can comprise a spirally wound member that forms in longitudinal cross-section a plurality of bubbles with a flattened surface at the inspiratory central bore. The inspiratory tube can enclose at least one heating element, and the at least one inspiratory heating element can be positioned between a bubble of the plurality of bubbles and the inspiratory central bore. The wall of the expiratory tube can comprise a foamed or unfoamed polymer.

A respiratory apparatus can comprise a humidifier, an inspiratory tube, an expiratory tube, and a control system. The humidifier is configured to humidify an inspiratory gases flow to be delivered to a patient. The humidifier comprises a humidification chamber and a heater. The humidification chamber is configured to store a volume of liquid and configured to be fluid communication with the inspiratory gases flow. The heater is configured to heat the volume of liquid in the humidification chamber to create vapor such that the inspiratory gases flow is humidified by the vapor. The inspiratory tube is configured to receive the humidified inspiratory gases flow from the humidifier. The inspiratory tube comprises a wall enclosing an inspiratory central bore, and the central bore of the inspiratory tube is smooth. The inspiratory tube further comprises a spirally wound first elongate member that forms in longitudinal cross-section a plurality of bubbles with a flattened surface at the inspiratory central bore. The bubbles are configured to insulate the inspiratory central bore. The inspiratory tube further comprises a spirally wound second elongate member joined between adjacent turns of the first elongate member. The second elongate member forms at least a portion of the lumen of the first elongate tube and comprises at least one inspiratory heating element embedded within the second elongate member. The expiratory tube is configured to receive an expiratory gases flow from the patient. The expiratory tube comprises a conduit enclosing an expiratory central bore, wherein the expiratory central bore is corrugated, and wherein the conduit is permeable to water vapor and substantially impermeable to liquid flow therethrough. The expiratory tube further comprises at least one expiratory heating element within the expiratory central bore. The control system can be configured to deliver power to the heater of the humidifier. The control system can be configured to deliver power to the at least one inspiratory heating element. The control system can be configured to deliver power to the at least one expiratory heating element. The control system can be configured to deliver power to the heater of the humidifier and the at least one inspiratory heating element. The control system can be configured to deliver power to the heater of the humidifier and the at least one expiratory heating element. The control system can be configured to deliver power to the at least one inspiratory heating element and the at least one expiratory heating element. The control system is configured to deliver power to two or more of the following: the heater of the humidifier, the at least one inspiratory heating element, and the at least one expiratory heating element. The control system is configured to deliver power to the heater of the humidifier, the at least one inspiratory heating element, and the at least one expiratory heating element.

The foregoing respiratory apparatus can also have one, some, or all of the following properties, as well as any property or properties described in this disclosure. The wall of the expiratory tube can comprise a foamed or unfoamed polymer that is permeable to water vapor and substantially impermeable to liquid water and bulk flow of the exhaled gases. The foamed polymer can comprise a solid thermoplastic elastomer material having cell voids distributed throughout. The unfoamed polymer can comprise a solid thermoplastic elastomer material that is permeable to water vapor and substantially impermeable to liquid water and bulk flow of the exhaled gases. The at least one inspiratory heating element can be between a bubble of the plurality of bubbles and the inspiratory central bore. The respiratory apparatus can further comprise a patient interface assembly between the inspiratory tube and the expiratory tube. The power delivered by the control system can be calculated to provide increased humidification by the humidifier. The power delivered by the control system can be calculated to provide controlled condensate management by the at least one expiratory heating element. The power delivered by the control system can be calculated to provide controlled condensate management by the at least one inspiratory heating element. The power delivered by the control system can be calculated to provide increased humidification by the humidifier and controlled condensate management by the at least one expiratory heating element and the at least one inspiratory heating element. The respiratory apparatus can further comprise a ventilator configured to provide the inspiratory gases flow and receive the expiratory gases flow. The ventilator can be configured to provide a pulsatile inspiratory gases flow to the humidifier. The ventilator can be configured to provide a constant inspiratory gases flow to the humidifier. The ventilator can be configured to provide a bias flow of gases.

A respiratory apparatus can comprise a humidifier, an inspiratory tube, and an expiratory tube. The humidifier is configured to humidify an inspiratory gases flow to a patient. The inspiratory tube is configured to receive the inspiratory gases flow from a gas source. The inspiratory tube comprises an inspiratory inlet, an inspiratory outlet, and a wall enclosing an inspiratory central bore, wherein the inner wall of the inspiratory tube is smooth. The expiratory tube is configured to receive an expiratory gases flow from a patient. The expiratory tube comprises an expiratory inlet, an expiratory outlet, and a wall enclosing an expiratory central bore. The inner wall of the expiratory tube is corrugated, and the wall of the expiratory tube is permeable to water vapor and substantially impermeable to liquid and gases flowing therethrough. The wall of the expiratory tube can comprise a foamed polymer that is permeable to water vapor and substantially impermeable to liquid water and bulk flow of the exhaled gases. The inspiratory tube can comprise at least one heating element within its central bore. The respiratory apparatus can also have one, some, or all of the following properties, as well as any properties described in this disclosure. The inspiratory tube can comprise at least one heating element attached to its inner wall. The inspiratory tube can comprise at least one heating element enclosed within its wall. The first elongate member of the inspiratory limb can form in longitudinal cross-section a plurality of bubbles with a flattened surface at the lumen. The inspiratory tube can enclose at least one heating element, and the at least one inspiratory heating element can be between a bubble of the plurality of bubbles and the inspiratory central bore. The expiratory tube can comprise at least one heating element within the expiratory central bore. The expiratory tube can comprise at least one heating element attached to its inner wall. The expiratory tube can comprise at least one heating element embedded within its inner wall. The expiratory tube can comprise a plurality of reinforcing ribs circumferentially arranged around the inner surface and generally longitudinally aligned between the inlet and the outlet. The respiratory apparatus can further comprise a control system configured to deliver power to the heater of the humidifier and the at least one heating element.

BRIEF DESCRIPTION OF THE DRAWINGS

Certain features, aspects, and advantages of the present disclosure now will be described with reference to the drawings. The drawings and the associated descriptions are provided to illustrate certain features, aspects, and advantages of the present disclosure and not to limit the scope of the disclosure.

DETAILED DESCRIPTION

Breathing Circuit Comprising One or More Medical Tubes

Figure 1:
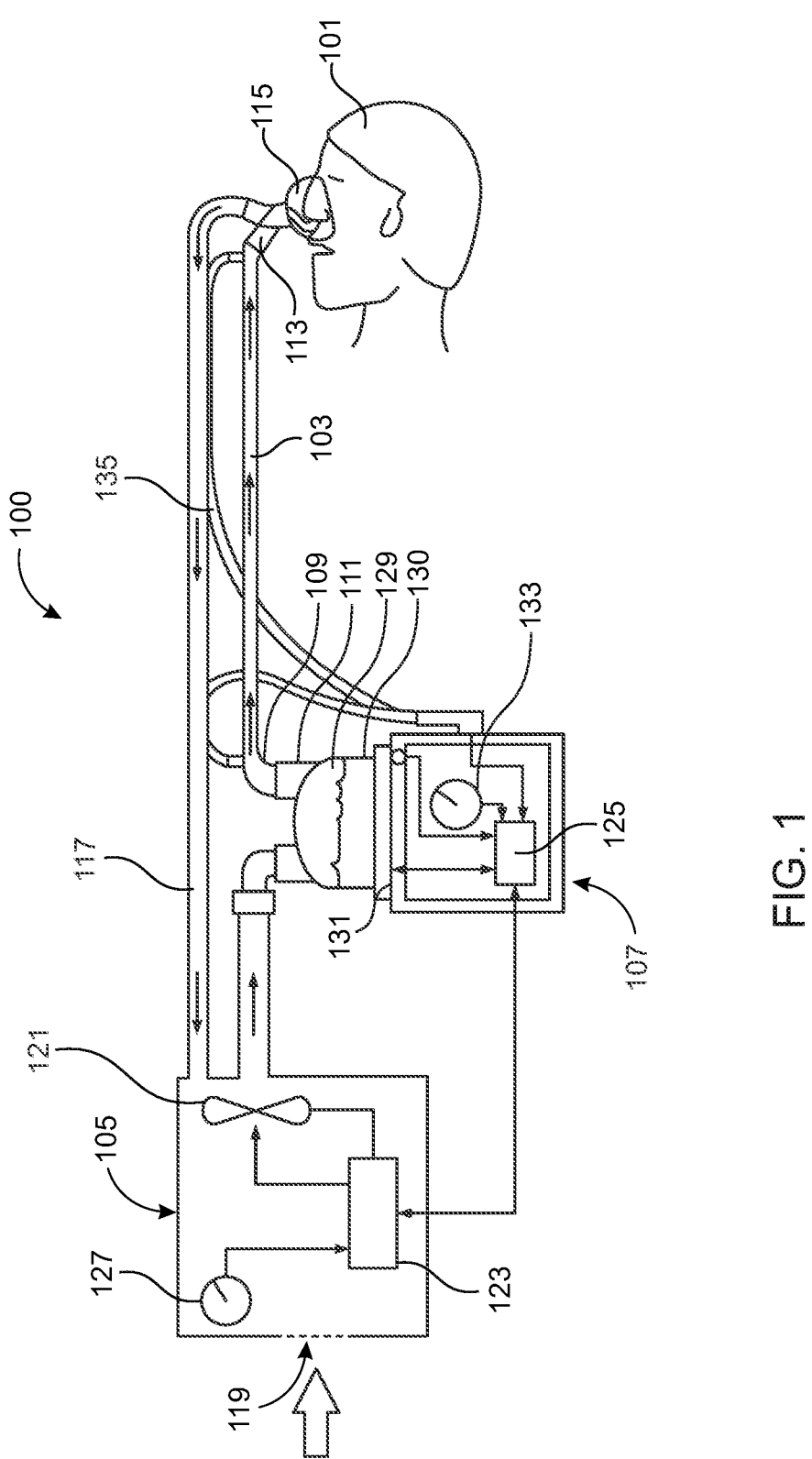
FIG. 1 is a schematic illustration of a breathing circuit incorporating one or more medical tubes.

For a more detailed understanding of the disclosure, reference is first made to FIG. 1, which shows a breathing circuit 100. Such a breathing circuit 100 can be a respiratory humidification circuit. The breathing circuit 100 includes one or more medical tubes. The breathing circuit 100 can include an inspiratory tube 103 and an expiratory tube 117.

As used herein, medical tube is a broad term and is to be given its ordinary and customary meaning to a person of ordinary skill in the art (that is, it is not to be limited to a special or customized meaning) and includes, without limitation, cylindrical and non-cylindrical elongate shapes defining a lumen or comprising a passageway, such as a hollow, elongate body that are configured for use in medical procedures and that otherwise meet applicable standards for such uses. An inspiratory tube is a medical tube that is configured to deliver breathing gases to a patient. An expiratory tube is a medical tube that is configured to move exhaled gases away from a patient.

Gases can be transported in the circuit 100 of FIG. 1. Ambient gases flow from a gases source 105 to a humidifier 107. The humidifier 107 can humidify the gases. The gases source 105 can be a ventilator, a blower or fan, a tank containing compressed gases, a wall supply in a medical facility, or any other suitable source of breathing gases.

The humidifier 107 connects to an inlet 109 (the end for receiving humidified gases) of the inspiratory tube 103 via a port 111, thereby supplying humidified gases to the inspiratory tube 103. The gases flow through the inspiratory tube 103 to an outlet 113 (the end for expelling humidified gases) of the inspiratory tube 103, and then to a patient 101 through a patient interface 115 connected to the outlet 113. The expiratory tube 117 connects to the patient interface 115. The expiratory tube 117 returns exhaled humidified gases from the patient interface 115 to the gases source 105 or to the ambient atmosphere. As used herein, patient interface has a broad meaning and is to be given its ordinary and customary meaning to one of skill in the art, and patient interface also includes, without any limitation, any one or more of a full face mask, a nasal mask, an oral mask, an oral-nasal mask, a nasal pillows mask, nasal cannulas, nasal prongs, a laryngeal mask, or any other suitable coupling between the medical circuit and the airways of the patient.

Gases can enter the gases source 105 through a vent 119. The blower or the fan 121 can cause gases to flow into the gases source 105 by drawing air or other gases through the vent 119. The blower or the fan 121 can be a variable speed blower or fan. An electronic controller 123 can control the blower or fan speed. In particular, the function of the electronic controller 123 can be controlled by an electronic master controller 125. The function can be controlled in response to inputs from the master controller 125 and a user-set predetermined required value (preset value) of pressure or blower or fan speed via a dial or other suitable input device 127.

The humidifier 107 comprises a humidification chamber 129. The humidifier chamber 129 can be configured to contain a volume of water 130 or other suitable humidifying liquid. The humidification chamber 129 can be removable from the humidifier 107. Removability allows the humidification chamber 129 to be more readily sterilized or disposed of after use. The humidification chamber 129 portion of the humidifier 107 can be a unitary construction or can be formed of multiple components that are joined together to define the humidifier chamber 129. The body of the humidification chamber 129 can be formed from a non-conductive glass or plastics material. The humidification chamber 129 can also include conductive components. For instance, the humidification chamber 129 can include a highly heat conductive base (an aluminum base) configured to contact or be associated with a heater plate 131 on the humidifier 107 when the humidification chamber 129 is installed on the humidifier 107.

The humidifier 107 can include electronic controls. The humidifier 107 can include the electronic, analog or digital master controller 125. The master controller 125 can be a microprocessor-based controller executing computer software commands stored in associated memory. In response to the user-set humidity or temperature value input via a user input device 133 and other inputs, the master controller 125 determines when (or to what level) to energize the heater plate 131 to heat the volume of water 130 within the humidification chamber 129.

A temperature probe 135 can connect to the inspiratory tube 103 near the patient interface 115 or the temperature probe 135 can connect to the patient interface 115. The temperature probe 135 can be integrated into the inspiratory tube 103. The temperature probe 135 detects the temperature near or at the patient interface 115. A signal reflecting the temperature can be provided by the temperature probe 135 to the electronic, analog or digital master controller 125. A heating element (not shown) can be used to adjust the temperature of the patient interface 115 and/or the inspiratory tube 103 to raise the temperature of the inspiratory tube 103 and/or the patient interface 115 above the saturation temperature, thereby reducing the opportunity for unwanted condensation.

In FIG. 1, exhaled humidified gases are returned from the patient interface 115 to the gases source 105 via the expiratory tube 117. The expiratory tube 117 can include a vapor permeable material, as described in greater detail below. The vapor permeable expiratory tube can be corrugated.

The expiratory tube 117 can have a temperature probe and/or heating element, as described above with respect to the inspiratory tube 103, to reduce the opportunity for condensation to reach the gases source 105. The expiratory tube 117 need not return exhaled gases to the gases source 105. The exhaled humidified gases can flow directly to ambient surroundings or to other ancillary equipment, such as an air scrubber/filter (not shown).

In FIG. 1, the inspiratory tube 103 includes or comprises a conduit with a smooth bore. The term smooth bore is to be given its ordinary and customary meaning in the art and includes, without limitation, non-corrugated bores, lumens, or passageways. The term "smooth bore" may be used to describe tubes that have an inner surface that does not include significant inner corrugations, annular ribs, bumps, or cavities that significantly influence the flow of gases within the tube. The term "smooth bore" may also be used to describe tubes that do not have repeating inner surface features that disturb a generally laminar flow through the passageway or lumen defined by the smooth bore. The term corrugated is to be given its ordinary and customary meaning in the art and includes, without limitation, having a ridged or grooved surface. Advantageously, the smooth bore causes the conduit to have a lower RTF than a conduit with comparable dimensions having a corrugated bore. A smooth bore reduces the resistance to flow such that the bore (i.e. diameter or cross-sectional area) can be reduced, which results in a lower compressible volume when compared to a corrugated tube having a similar resistance to flow. The inspiratory conduit can be a composite conduit. The composite conduit generally may be defined as a conduit comprising two or more distinct portions, or, more specifically, two or more components that are joined together to define the conduit. The composite conduit can be spirally wound. The composite conduit can be spirally wound in such a way that the two or more components are spirally intertwined or coupled side by side in a spiraling configuration.

The expiratory tube 117 includes or comprises a conduit having at least a portion that is vapor permeable. Vapor permeability facilitates humidity removal. At least the vapor permeable portion of the expiratory tube 117 can be corrugated. The corrugation can be on the inside of the tube. Corrugation increases the inner surface area of the tube. The amount of vapor that can be diffused through a vapor permeable material correlates to the surface area of the material in direct contact with the vapor. Corrugation also increases turbulent flow of gases within the expiratory tube. More turbulent flow means better mixing of the gases, thereby causing the water vapor to travel to the outer walls of the expiratory tube 117. More turbulent flow can increase localized residence in the corrugations in the expiratory tube, which, when coupled with vapor permeability attributes, further improves humidity removal. Increased localized residence time also decreases the temperature of the gases swirling in the "pocket" of each corrugation relative to that of a comparably sized smooth bore tube, which increases the relative humidity of those gases relative to that of a comparably sized smooth bore tube. The increased relative humidity increases the vapor pressure gradient across the wall of the expiratory tube 117 relative to that of a comparably sized smooth bore tube, which in turn increases vapor diffusion through the wall of the corrugated expiratory tube relative to that of a comparably sized smooth bore tube.

A vapor permeable, corrugated conduit can be formed, at least in part, from a foamed or unfoamed polymer that is permeable to water vapor and substantially impermeable to liquid water and bulk flow of gases. The expiratory tube 117 can comprise a wall defining a space within the expiratory tube 117. At least a part of the wall can be formed of a foamed material configured to be permeable to water vapor and substantially impermeable to liquid water and bulk flow of gases. At least a part of the wall can be formed of an non-foamed extruded solid material that is permeable to water vapory and substantially impermeable to liquid water and bulk flow of gases.

A vapor permeable expiratory tube 117 can be formed from non-foam based materials. The non-foam based materials can include a helically-wrapped vapor permeable tape, or the non-foam based materials may be extruded in a continuous tube. Corrugation of the expiratory tube 117 can be accomplished using non-foam based materials. The non-foam based materials can include beads of varying diameters arranged in an alternating pattern to form a corrugated inner surface. Alternatively, the corrugations may be created in the tube by methods which are known in the art, such as moulding or stamping.

The inspiratory tube 103 includes a smooth bore conduit. The smooth bore conduit can be heated and insulated to minimize condensate creation and maximize humidity delivery. Decreased condensate formation within the inspiratory tube permits more vapor in humidified gases to be delivered to a patient. Several factors affect condensate creation within the inspiratory tube 103 including the inner bore diameter, the degree of inner bore smoothness, the level of tube insulation, the presence of heating elements (such as wires and elements) associated with the tube 103, and the position of heating elements within the tube 103 (whether heating elements are located within the inner bore of the tube 103 or within the wall of the tube 103). Specifically, decreasing the inner bore diameter of the inspiratory tube 103 increases gases velocity as gases travel through the inspiratory tube 103. Increasing the smoothness of the bore decreases turbulence and creates a more parabolic wavefront across the inner wall of the lumen. Therefore, decreasing the inner bore diameter and making the inner bore smooth causes the faster gases located near the center of the tube to transfer less heat to the slower gases located near the tube wall. A smooth bore tube also provides no pockets in which vapor could be trapped or condensate might pool, as a corrugated tube would have. The vapor carried by the gases is therefore encouraged to exit the tube and thus be delivered to the patient.

Increasing the degree of tube insulation reduces heat loss across the wall of the inspiratory tube 103, which maximizes humidity delivery by minimizing condensation formation. Adding increased insulation to the inspiratory tube 103 also makes the breathing circuit 100 more efficient by decreasing how hard a heating element must work to maintain a target temperature and humidity because the insulated tube will better maintain the temperature and absolute humidity of the gases as they travel through the tube.

Adding heating elements to the inspiratory tube 103 also maximizes humidification delivery and decreases condensation. Positioning one or more heating elements within the wall of the inspiratory tube 103 maximizes humidification, minimizes condensate formation, and contributes to the efficiency of the inspiratory tube 103, the breathing circuit 100, or the humidification system. When located within the wall of the inspiratory tube 103, the heating element heats the wall while not directly heating the gases. Heating the wall reduces the relative humidity (heating gases increases the temperature, which reduces the relative humidity) of gases near the wall. Positioning the heating element on the lumen side of an inner wall of insulating "bubbles" (defined below) of an inspiratory tube 103 (described in greater detail below) can further reduce heat loss outward through the wall of the inspiratory tube 103, which in turn maximizes humidification while minimizing condensate creation. As used herein, the term "bubble" refers to the cross-sectional shape of the hollow body formed from an elongated wind or turn of the first elongate member 203, taken in transverse cross-section through the wind or turn, for example as shown in FIG. 2B. As used herein, any reference to "bubble" means an elongate hollow body that, in cross-section, has a shape defined by a wall with a hollow space within. Such shapes could include an oval or "D" shape, with reference to FIG. 2B. Such shapes could include, without limitation, "O" shapes, and other regular and irregular shapes, symmetric and asymmetric.

The expiratory tube 117 can include a corrugated conduit to maximize vapor removal while minimizing condensate formation and increasing localized residence time in the corrugations. The expiratory tube 117 can include a vapor permeable conduit to maximize vapor removal. The expiratory tube 117 can include a heated conduit to maximize vapor removal while minimizing condensate formation. The expiratory tube 117 can include a corrugated, vapor permeable, and/or heated conduit to maximize vapor removal while minimizing condensate formation and increasing localized residence time in the corrugations. Decreased condensate formation within the expiratory tube 117 permits more vapor to diffuse across the wall of the expiratory tube 117. The presence of a heating element can maintain the relative humidity of the gases below 100% (that is, maintain the gases temperature above the dewpoint saturation temperature). Positioning the heating element near or within the wall of the expiratory tube 117 causes heating of the gases near the wall of the expiratory tube 117. Keeping the gases temperature near the wall of the expiratory tube 117 above dewpoint avoids or limits condensate formation. The inspiratory tube 103 and the expiratory tube 117 are described in even greater detail elsewhere in this specification.

Referring back to FIG. 1, the gases source 105 typically intends to deliver a set volume of gas to the patient 101 for each breath. This set volume can be referred to as a tidal volume or delivered volume. It is desired that the patient 101 receives the correct gas volume in order to reduce the likelihood of risk of lung injury and to increase the likelihood of sufficient ventilation. When a gases source 105, such as a ventilator, creates a breath for a patient, the gases source 105 must fill both the patient lung and the breathing circuit 100, which can include the filter, the supply tube from the ventilator to the humidifier, the humidifier chamber, the inspiratory tube, the expiratory tube, and any other components shown or described with respect to FIG. 1. Therefore, the gases source 105 must estimate or otherwise account for the gas used to fill the breathing circuit 100 and compensate for this to increase the likelihood of accurate delivery of gas volume to the patient.

The gases source 105 can conduct a test for pneumatic compliance of the breathing circuit 100. In this test, the gases source 105 is attempting to determine the volume required to create a specific pressure. Pneumatic compliance is dependent on at least compressible volume. The lower the compressible volume of the breathing circuit 100, the lower the pneumatic compliance of the breathing circuit 100 for a fixed extensibility. The lower the pneumatic compliance of a breathing circuit relative to the patient lung compliance, the less potential there is for error in delivered tidal volume. If a measurement of pneumatic compliance of the breathing circuit is incorrect by a small amount and the pneumatic compliance of the breathing circuit is large in comparison to the patient's lung compliance, then the percentage error in delivered tidal volume to the patient will become very large. For example, if a measurement of pneumatic compliance of the breathing circuit is incorrect by 5%, and the pneumatic compliance of the breathing circuit is large in comparison to the patient's lung compliance, then the percentage error in delivered tidal volume to the patient is potentially much larger than 5%.

Figure 1A:
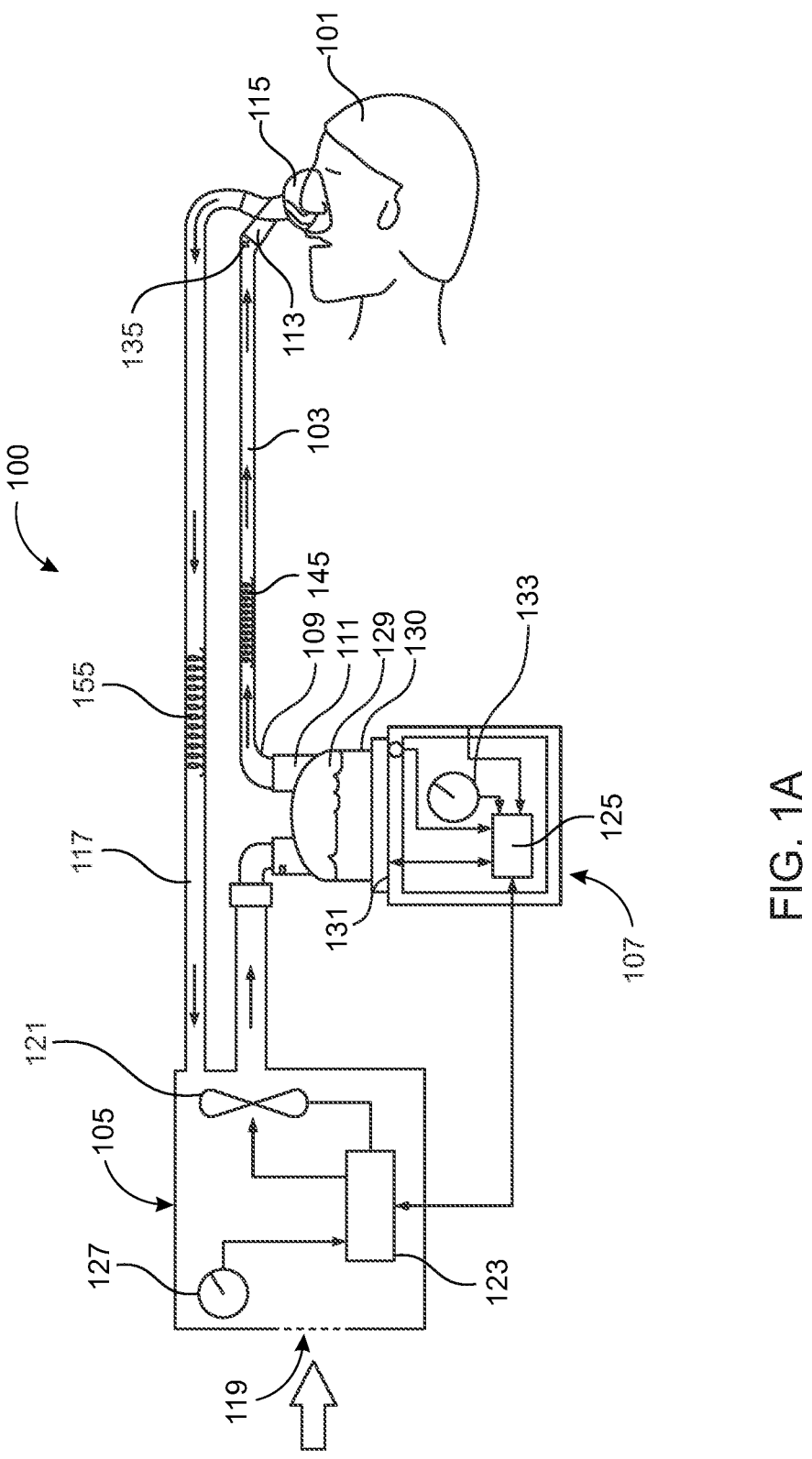
FIG. 1A is a schematic illustration of a breathing circuit incorporating one or more medical tubes.
Figure 1B:
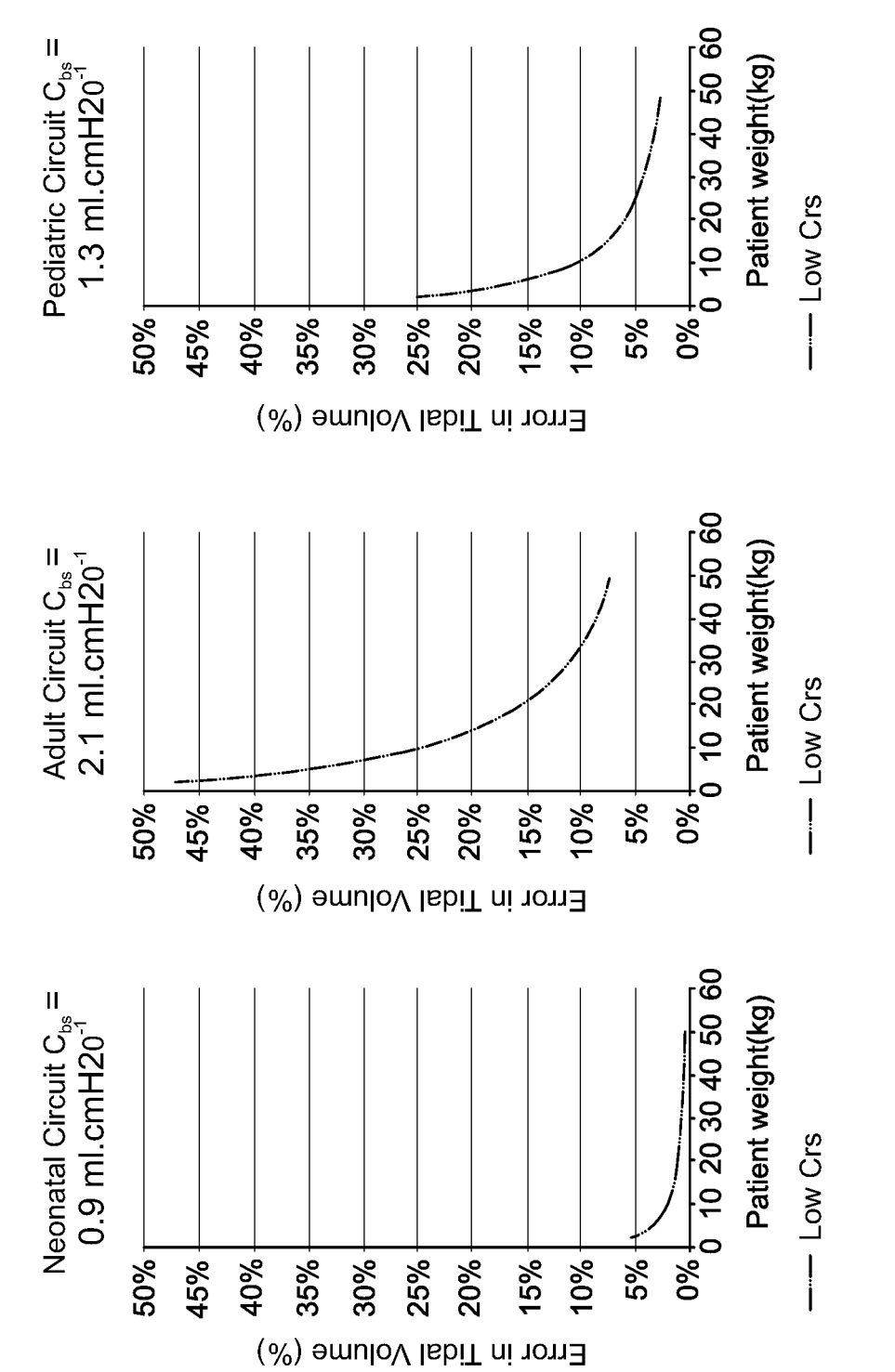
FIG. 1B shows three graphs demonstrating an impact of breathing circuit compliance on tidal volume error.

FIG. 1B illustrates three graphs. The graphs of FIG. 1B demonstrate the error in delivered tidal volume with a theoretical 10% error introduced in the gases source measurement of breathing circuit pneumatic compliance. The three graphs are for three different circuit compliance specifications (e.g., neonatal, adult and pediatric). For the neonatal circuit, the breathing circuit compliance ($C_{bs}$) equals 0.9 ml·cmH20$^{-1}$. For the adult circuit, the breathing circuit compliance ($C_{bs}$) equals 2.1 ml·cmH20$^{-1}$. For the pediatric circuit, the breathing circuit compliance ($C_{bs}$) equals 1.3 ml·cmH20$^{-1}$. Each graph shows the error in delivered tidal volume for a patient with low respiratory system compliance.

It has been discovered that the error dramatically increases as the patient's weight decreases. The patient's weight is correlated to the intended tidal volume. As the patient's weight decreases, the intended tidal volume decreases. Comparing the graphs of FIG. 1B illustrates that, for a given tidal volume, the error is larger if the breathing circuit compliance is larger. It has been discovered that it is desirable to keep the overall compressible volume and compliance of the breathing circuit as low as possible in relation to the lung characteristics of the patients intended to be receiving treatment.

Due to practical reasons, such as minimizing resistance to gas flow of the tubing and enabling the tubes to be long enough to manage the patient in the bed space, the breathing circuit tubing compressible volume and therefore compliance is usually much larger than the patient's lungs. This difference is made greater by some lung disease states leading to patients with very stiff, low compliance lungs. A low compressible volume, which can result from short tubes, can be disadvantageous from a usability perspective. Longer tubes, and breathable expiratory limbs, which benefit from higher surface area, can be disadvantageous from a compressible volume perspective.

The relevance of compressible volume is that there can be a tradeoff between components of the breathing circuit in maintaining a sufficiently low compressible volume. The smooth bore of the inspiratory tube 103 lowers the resistance to flow, which allows the reduction in the diameter of the inspiratory tube 103 and therefore a reduction in the compressible volume. This lowering of the compressible volume of the inspiratory tube 103 allows for an increase the compressible volume of the expiratory tube 117 by increasing the diameter. Increasing the diameter of expiratory tube 117 creates a greater surface area of the expiratory tube 117, which increases the vapor permeability of the tube 117.

It was realized that incorporating the inspiratory tube 103 with a smaller diameter, smooth bore conduit in conjunction with the expiratory tube 117 with a corrugated conduit allows the expiratory tube 117 to be larger in diameter and/or longer than otherwise would be possible while maintaining the overall system compressible volume. Additionally or alternatively, the combination of the smaller diameter, smooth bore inspiratory tube 103 and the larger diameter, corrugated expiratory tube 117 can maintain the overall pressure drop. Additionally or alternatively, the combination of the smaller diameter, smooth bore inspiratory tube 103 and the larger diameter, corrugated expiratory tube 117 can maintain the resistance to flow (RTF) of the breathing circuit 100 at a desirable level. Ordinarily, increasing the length of a conduit undesirably increases the compressible volume of the conduit, and therefore, the compressible volume of the overall breathing circuit. Ordinarily, increasing the length of a conduit undesirably increases the RTF of the conduit, and therefore, increases the RTF of the overall breathing circuit. On the other hand, when the conduit is vapor permeable, the increased length advantageously improves the conduit's ability to remove vapor from exhaled gases. It was discovered that the combination of the inspiratory tube 103 with a smaller diameter, smooth bore and the expiratory tube 117 with a corrugated, vapor-permeable, larger diameter conduit increases the ability of the expiratory tube 117 to remove water vapor from the breathing circuit without increasing the overall system compressible volume, pressure drop, and/or RTF.

It was further realized that incorporating the inspiratory tube 103 with a smooth bore conduit in conjunction with the expiratory tube 117 with a corrugated conduit allows the humidifier 107 to increase humidity performance providing a therapeutic benefit to patients, while driving closer to fully saturated gases, without adding the risk of liquid damage to the gases source 105 or condensate draining back to patient.

The inspiratory tube 103 with a smooth bore, spiral wound conduit can be paired with the expiratory tube 117 with a corrugated, vapor permeable conduit. As discussed above, the smooth bore of the inspiratory tube 103 has lower RTF than a similarly sized corrugated bore. It can also have a smaller internal diameter than a corrugated conduit. Ordinarily, decreasing internal diameter reduces compressible volume and undesirably increases the inspiratory tube's RTF. Nevertheless, the smooth bore characteristics can be selected such that the reduction in RTF associated with the smooth bore of the inspiratory tube 103 outweighs the RTF increase resulting from the smaller internal diameter of the inspiratory tube 103. This selection of a smaller diameter inspiratory tube 103 also reduces the compressible volume of the inspiratory tube 103. This selection then allows the corrugated expiratory tube 117 paired with the smooth bore inspiratory tube 103 to be longer and/or have a greater diameter or cross-sectional area without increasing the overall system pressure drop or compressible volume. The increased length and/or diameter of the expiratory tube 117 ordinarily undesirably increases the RTF and compressible volume of the tube. However, the increased length and/or diameter also improves the ability of the vapor permeable tube to remove vapor from expiratory gases. In this arrangement, pairing the smooth bore inspiratory tube 103 with the corrugated expiratory tube 117 enhances the performance of the expiratory tube 117. The system pressure drop of a breathing circuit as might exist from ventilator outlet to ventilator inlet can be affected by the pressure characteristics (RTF) of each element in the circuit. Referring back to FIG. 1, assuming the pressure characteristics of the supply tube from ventilator to humidifier, humidifier chamber, interface tube, and interface body are fixed, the primary factors contributing to system pressure drop are the resistance to flow and dimensions (length and diameter) of the inspiratory tube 103 and the expiratory tube 117. Any change to one of these factors should advantageously be balanced by other factor(s) to avoid increasing the system pressure drop, RTF and/or compressible volume. As described herein, the primary factors contributing to compressible volume are the tube profile, extensibility, and dimensions (length and diameter or cross-sectional area) of the inspiratory tube 103 and the expiratory tube 117. There can be a tradeoff between decreasing the compressible volume of the inspiratory tube 103 and increasing the compressible volume of the expiratory tube 117 while maintaining the compressible volume of the breathing circuit. As described herein, increasing the compressible volume of the expiratory tube 117 has advantages in in vapor permeability in the expiratory limb.

The smooth bore of the inspiratory tube 103 can reduce resistance to flow (as compared to a corrugated inspiratory tube), decreasing the overall system pressure drop. This

117 increases the surface area of the tube wall of the expiratory tube 117. The amount of vapor that can be diffused through a vapor permeable material is correlated to the surface area of the material. Increasing the length and//or the diameter of the expiratory tube 117 increases the surface area of the wall of the expiratory tube 117 and also increases the residence time of gases in the expiratory tube 117. The amount of vapor that can be diffused through a permeable material is also correlated to the length of time the vapor-carrying gases are in contact with the material.

The compressible volume of the breathing circuit (the cumulative volume of the entire gases flow path) can also be balanced in the same way. For instance, a change in dimensions (cross-sectional area or diameter, length) of the inspiratory tube 103 can offset a change in dimensions (cross-sectional area or diameter, length) of the corrugated expiratory tube 117. As described herein, the decrease in diameter of the inspiratory tube 103 can decrease compressible volume. This decrease in compressible volume can improve accuracy of the delivered tidal volume. As described herein, the decrease in diameter of the inspiratory tube 103 can offset an increased diameter and/or an increased length of the expiratory tube 117. As described herein, the change in dimensions of the expiratory tube 117 can facilitate the function of the expiratory tube 117, such as by increasing vapor permeability of the expiratory tube 117. Altering tube dimensions affects both the system pressure drop and the system compressible volume, so both equations should advantageously be balanced or selected simultaneously when making changes. Reducing the diameter of the inspiratory tube 103 can both increase resistance to flow and decrease compressible volume, while increasing the average gases velocity through the tube. Adding to the length of the corrugated expiratory tube 117 both increases resistance to flow and increases compressible volume. Table 1 summarizes the impacts of various features on these two system metrics:

TABLE 1

| Feature | Effect | Pressure drop | Compressible volume |
|---|---|---|---|
| Inspiratory length | Shorter: decreases residence time, decreasing condensation (but too short impacts usability) | Decreases | Decreases |
| Inspiratory diameter | Narrower: decreases residence time, decreasing condensation | Increases | Decreases |
| Expiratory length | Longer: increases surface area and residence time, both increasing vapor diffusion | Increases | Increases |
| Expiratory diameter | Wider: increases surface area and residence time, both increasing vapor diffusion | Decreases | Increases |
| Inspiratory bore surface | Smooth: decreases turbulence, decreasing condensation | Decreases | No change |
| Expiratory bore surface | Corrugated: increases turbulence, increasing vapor diffusion | Increases | No change | allows any or all of the other three factors (resistance to flow of the corrugated expiratory tube 117 or dimensions of either tube) to be altered in a way that increases the system pressure drop. The internal diameter of the inspiratory tube 103 can be smaller than the comparable corrugated inspiratory tube, which desirably increases the velocity of the gases flowing through the inspiratory tube 103. However, the smaller diameter also adds back some resistance to flow. So long as the RTF increase caused by the smaller diameter is sufficiently smaller than the RTF decrease caused by the use of the smooth bore, the length of the corrugated expiratory tube 117 can be increased without increasing the system pressure drop. Increasing the length of the expiratory tube Pairing the corrugated expiratory tube 117 with the smooth bore inspiratory tube 103 enables higher performance of the inspiratory tube 103. Pairing the larger diameter expiratory tube 117 with the smaller bore inspiratory tube 103 can be net neutral for compressible volume, but increase functionality of the breathing circuit (e.g., increase vapor diffusion in the expiratory tube 117). In this arrangement, the smooth bore inspiratory tube 103 minimizes condensate creation, and therefore maximizes humidity delivery. The overall compressible volume can be decreased by changes in the dimensions, such as diameter and length of the inspiratory tube 103 and expiratory tube 117. In some arrangements, the inspiratory tube 103 is insulated, which helps to make the humidifier 107 and/or a heating element, such as the heater plate 131, more efficient in producing humidity that is delivered to the patient 101. The heater plate 131 does not have to work as much because it does not have to produce such a high target temperature at the humidification chamber port 111, and this is because the heated and insulated inspiratory tube 103 will better maintain the absolute humidity of the gases flowing from the humidification chamber port 111 and through the inspiratory tube 103.

The location of a heater wire in the wall of the inspiratory tube 103 also increases the efficiency of the inspiratory tube 103 in maintaining the relative humidity of the gas. The heater wire can heat the wall of the inspiratory tube 103, not the gases flowing through the lumen of the inspiratory tube 103, which reduces the relative humidity of the gases near the wall of the inspiratory tube 103. When the inspiratory tube 103 includes a composite conduit with a spiral wound hollow body or "bubble" tube (described in greater detail below), the heater wire is under (on the lumen side of an inner wall) the insulating bubble, which reduces heat loss outward through the wall of the inspiratory tube 103.

The smooth bore inspiratory tube 103 promotes laminar gases flow, which creates a more parabolic wavefront across the lumen of the inspiratory tube 103, with the gases closer to the center of the lumen having a higher velocity relative to gases closer to the wall of the inspiratory tube 103. In this arrangement, the higher velocity gases have less time during transit from the inlet 109 to the outlet 113 to transfer heat to neighboring lower velocity gases. Combined with the inward direction of the heat generated by the heater wire, this arrangement helps to further increase the heat retained by the gases flow.

The smooth bore inspiratory tube 103 also provides no pockets in which vapor could be trapped or condensate might pool, as a corrugated tube would have. The vapor carried by the gases is therefore encouraged to remain in vapor phase and exit the inspiratory tube 103 and thus be delivered to the patient 101.

The corrugated expiratory tube 117 maximizes vapor removal and minimizes condensate formation. The expiratory tube 117 can be vapor permeable which promotes diffusion of vapor through the wall of the expiratory tube 117 to the outside atmosphere. In some arrangements, the expiratory tube 117 is vapor permeable and heated; the control of the heating along the tube promotes diffusion of vapor through the wall of the expiratory tube 117 to the outside atmosphere. Vapor transferred to the outside atmosphere will not be delivered to the gases source 105. The corrugated expiratory tube 117 creates turbulence in the portion of the gases flow adjacent the wall of the expiratory tube 117, which increases the residence time of gases adjacent the wall in the corrugations. Increased residence time increases the opportunity for vapor diffusion through the wall of the expiratory tube 117. Increased residence time also decreases the temperature of the gases swirling in the "pocket" of each corrugation, which increases the relative humidity of those gases. The increased relative humidity increases the vapor pressure gradient across the wall of the expiratory tube 117, which in turn increases vapor diffusion through the wall.

As discussed below, the expiratory tube 117 can include a heater wire coiled near the center of the lumen of the expiratory tube 117. The heater wire, so positioned, adds to the turbulence of the gases flow and while minimizing condensate formation. More turbulence means better mixing of the gases, thereby causing the water vapor to travel to the outer walls of the expiratory tube 117. The corrugated expiratory tube 117 also provides corrugation "pockets" that have the advantage of collecting any liquid that condenses from vapor. Liquid pooled in the corrugations is liquid not delivered to the gases source 105. In some arrangements, the heater wire can be positioned in the wall of the expiratory tube 117. The presence of a heater wire in the expiratory tube 117 also minimizes condensate formation within the expiratory tube.

The combination of the smooth bore inspiratory tube 103 with the corrugated expiratory tube 117 allows the humidifier 107 to increase humidity performance. There is a contribution from the patient and bias flow in both invasive and non-invasive ventilation. In both, the expiratory tube 117 can function to decrease the amount of humidity returned to the gases source 105. The function of the expiratory tube 117 can be to sufficiently reduce the amount of humidity returned to the gases source 105.

The function of the expiratory tube can enable the humidifier 107 and the inspiratory tube 103 to deliver higher levels of humidity to the patient 101. If the expiratory tube 117 could not sufficiently reduce the amount of humidity returned to the gases source 105, the ability of the humidifier 107 and the inspiratory tube 103 to deliver higher levels of humidity to the patient 101 would have to be reduced or dialed back, because some of that extra humidity would be carried through the expiratory tube 117 to the gases source 105.

Applicant has made the surprising discovery related to breathing circuits that, with respect to compressible volume within the overall system, there can be a tradeoff between components of the breathing circuit 100, specifically between the inspiratory tube 103 and the expiratory tube 117. It was realized that there can be a reduction in diameter of the inspiratory tube 103 by switching from a corrugated tube to a smooth bore tube while maintaining the same resistance to flow (RTF). Applicant has surprisingly found that, while maintaining the overall compressible volume of the breathing circuit, the diameter of the expiratory tube 117 can be increased to a theoretical maximum nominal diameter. With corrugated tubes, the nominal diameter equals an average of the maximum and minimum diameter of the corrugated tube.

The typical industry standard corrugated tube diameters for breathing circuits include 10 mm, 15 mm, and 22 mm. In some instances in industry, these tube sizes are merely names, or merely refer to the size of the connectors on the ends of the tubes, rather than referring to the actual tube inner, outer, and/or nominal diameters. While not limited in practice, smaller diameter tubing such as 10 mm tubing or 12 mm tubing can be useful for neonatal patients, 15 mm tubing can be useful for pediatric patients, and 22 mm tubing can be useful for adult patients. Other inner diameters or nominal diameters of tubing such as 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, and ranges comprising two or more diameters disclosed herein, are contemplated. It was discovered that the diameter of the inspiratory tube 103 can be reduced if the bore is smooth instead of corrugated, assuming a constant RTF for the inspiratory limb.

Given three standard corrugated tube diameters of 10 mm, 15 mm, and 22 mm, it was surprisingly discovered that the resistance to flow could be matched between smooth bore tubes of various inner diameters and corrugated tubes of various nominal diameters. Each corrugated tube has a RTF which can be measured through testing apparatuses. Each corrugated tube has a RTF which can be theoretically calculated using dimensions of the tubing. Similarly, each smooth bore tube has a RTF which can be measured through testing apparatuses. In addition to, or alternatively to, testing, the RTF can be theoretically calculated. It was discovered that for each of the corrugated tubes having a nominal diameter, the RTF can be matched to a corresponding smooth bore tube of a smaller diameter. As one non-limiting example discovered by Applicant, a corrugated tube having a nominal diameter of 10 mm may be substantially equivalent to a 6.9 mm smooth bore tube based on the two tubes having the same RTF. As another example discovered by Applicant, a corrugated tube having a nominal diameter of 15 mm may be substantially equivalent to an 8 mm smooth bore tube based on substantially similar RTF. As yet another example discovered by Applicant, a corrugated tube having a nominal diameter of 22 mm may be substantially equivalent to a 13.5 mm smooth bore tube based on substantially similar RTF. The smooth bore inspiratory tube 103 thus can be reduced in diameter compared to a corrugated inspiratory tube without increasing the RTF in the inspiratory limb of a breathing circuit.

The overall compressible volume of the breathing circuit is taken to be the sum of the compressible volume of the inspiratory limb and the compressible volume of the expiratory limb. Given three industry standard corrugated tube diameters of 10 mm, 15 mm, and 22 mm, the compressible volume of the breathing circuit can be determined. Each corrugated tube has a compressible volume that can be measured through testing apparatuses. Each corrugated tube has a compressible volume that can be theoretically calculated based on the dimensions of the corrugated tube. For the corrugated tubes, the compressible volume can be calculated based on an assumption that the nominal diameter of the corrugated tube equals an average of the maximum and minimum diameter of the corrugated tube. It was discovered that the overall compressible volume of a breathing circuit with corrugated inspiratory and expiratory tubes can be maintained in the breathing circuit 100 in which the inspiratory tube 103 has a smooth bore and the expiratory tube is corrugated.

It was discovered that changes in compressible volume of the inspiratory limb can be traded off with changes in compressible volume of the expiratory limb of the breathing circuit while maintaining the overall compressible volume of the breathing circuit created by standard corrugated tubes. It was discovered that the smooth bore inspiratory tube 103 can have a reduced diameter while maintaining the RTF of the inspiratory limb. By decreasing the diameter of the inspiratory tube in the inspiratory limb, achievable by changing from a corrugated tube to a smooth bore tube, there was decrease in the compressible volume of the inspiratory limb of the breathing circuit. It was discovered that this decrease in compressible volume from the smooth bore inspiratory tube 103 could be traded off with an increase in compressible volume of the corrugated expiratory tube 117 while maintaining the overall compressible volume of the breathing circuit. The reduction in compressible volume of the smooth bore inspiratory tube 103 can be determined and added to the compressible volume allowance of the expiratory tube 117.

It was discovered that the expiratory tube 117 can have a theoretical maximum nominal diameter based on the decrease in compressible volume from the inspiratory tube 103. As one non-limiting example discovered by Applicant, a 6.9 mm smooth bore inspiratory tube 103 can offset a 14.7 mm corrugated expiratory tube 117 without a change in overall compressible volume of the breathing circuit. As another example discovered by Applicant, an 8 mm smooth bore inspiratory tube 103 can offset a 19.3 mm corrugated expiratory tube 117 without a change in overall compressible volume of the breathing circuit. As yet another example discovered by Applicant, a 13.5 mm smooth bore inspiratory tube 103 can offset a 27.4 mm corrugated expiratory tube 117 without a change in overall compressible volume of the breathing circuit. The theoretical maximum nominal diameter of the corrugated expiratory tube 117 maintains the total breathing circuit compressible volume. The compressible volume remains unchanged because the reduction in compressible volume from the changes in design of the inspiratory tube 103 allows for an increase in compressible volume for the design of the expiratory tube 117.

It was discovered that the heater wire inside the inspiratory tube 103 has an adverse impact on the RTF (i.e. it increases RTF when all other factors are held constant) and therefore the presence of a heater wire can limit the reduction of diameter of smooth bore inspiratory tube 103. As one non-limiting example discovered by Applicant, a corrugated tube having a nominal diameter of 10 mm may be substantially equivalent to a 9.3 mm smooth bore tube based on RTF, excluding the RTF of the heater wire. It was discovered that a 9.3 mm smooth bore inspiratory tube 103 can offset a 13.4 mm corrugated expiratory tube 117 without a change in overall compressible volume of the breathing circuit, as compared to a nominal 10 mm corrugated inspiratory and expiratory circuit. As another example discovered by Applicant, a corrugated tube having a nominal diameter of 15 mm may be substantially equivalent to a 12.7 mm smooth bore tube based on RTF, excluding the RTF of the heater wire. It was discovered that a 12.7 mm smooth bore inspiratory tube 103 can offset a 16.6 mm corrugated expiratory tube 117 without a change in overall compressible volume of the breathing circuit, as compared to a nominal 15 mm corrugated inspiratory and expiratory circuit. As yet another example discovered by Applicant, a corrugated tube having a nominal diameter of 22 mm may be substantially equivalent to a 20.3 mm smooth bore tube based on RTF, excluding the RTF of the heater wire. It was discovered that a 20.3 mm smooth bore inspiratory tube 103 can offset a 22.9 mm corrugated expiratory tube 117 without a change in overall compressible volume of the breathing circuit, as compared to a nominal 22 mm corrugated inspiratory and expiratory circuit.

As another non-limiting example discovered by Applicant, a corrugated tube having a nominal diameter of 10 mm may be substantially equivalent to a 5.9 mm smooth bore tube based on RTF, taking into account the RTF of the heater wire. It was discovered that a 5.9 mm smooth bore inspiratory tube 103 can offset a 12.8 mm corrugated expiratory tube 117 without a change in overall compressible volume of the breathing circuit, as compared to a nominal 10 mm corrugated inspiratory and expiratory circuit. The corrugated tube having a nominal diameter of 10 mm may have, for example, a nominal compressible volume of 78,539.8 mm³/ m. The RTF of the corrugated tube having a nominal diameter of 10 mm can be calculated using a trend line. The smooth bore inspiratory tube 103 can have a nominal diameter of 5.9 mm, which is the comparable smoothbore inner diameter for the same pressure using the trend line. The RTF can be the same or approximately the same for the standard tubing and the smooth bore inspiratory tube 103, e.g., 75.93 cmH20/l/min. The smooth bore inspiratory tube may have, for example, a compressible volume of 27,631.9 mm³/m. In such a case, the compressible volume difference can be, for example, 50,907.9 mm³/m. The corrugated expiratory tube 117 can have the total compressible volume which is the sum of the compressible volume of the corrugated tube having a nominal diameter of 10 mm and the compressible volume difference, e.g., 129,447.7 mm³/m. The corrugated expiratory tube 117 can therefore have a maximum nominal diameter of 12.8 mm to maintain the overall compressible volume of the circuit (inspiratory and expiratory limbs). In addition or in the alternative, the corrugated expiratory limb may have a nominal diameter less than the maximum, and the inspiratory and/or expiratory limb may be lengthened over the prior art lengths. For example, the inspiratory and expiratory limbs may be provided at lengths such as 1.75 m, or at other lengths disclosed herein. One of skill in the art would appreciate that this option—increasing the length of the inspiratory and/or expiratory limb rather than using the maximum possible expiratory diameter or increasing the length (of the inspiratory and/or expiratory limb) and increasing the diameter to less than the maximum possible diameter—is available with respect to each embodiment disclosed herein, and may be utilized to achieve the herein described beneficial technical effects.

As another example discovered by Applicant, a corrugated tube having a nominal diameter of 15 mm may be substantially equivalent to a 6.7 mm smooth bore tube based on RTF, taking into account the RTF of the heater wire, as determined using the trend lines. It was discovered that a 6.7 mm smooth bore inspiratory tube 103 can offset a 20.1 mm corrugated expiratory tube 117 without a change in overall compressible volume of the breathing circuit, as compared to a nominal 15 mm corrugated inspiratory and expiratory circuit. The compressible volume of the 15 mm corrugated tubing using the trend line may be, for example, 176,714.6 mm³/m. Similarly, the smooth bore inspiratory tube 103 may have a compressible volume of 34,820.4 mm³/m It follows that the compressible volume difference can be 141,894.2 mm³/m between the standard tubing and the new smooth bore inspiratory tube 103. The corrugated expiratory tube 117 can have the total compressible volume which is the sum of the compressible volume of the corrugated tube having a nominal diameter of 15 mm and the compressible volume difference, e.g., 318,608.8 mm³/m. Additionally, as these are per meter values, it should be appreciated by one of skill that the length of the inspiratory and/or expiratory limb could additionally be increased relative to prior art limb lengths without increasing the overall compressible volume of the circuit, as described further herein.

As yet another example discovered by Applicant, a corrugated tube having a nominal diameter of 22 mm may be substantially equivalent to a 10.9 mm smooth bore tube based on RTF, taking into account the RTF of the heater wire, as determined by using the trend lines. It was discovered that a 10.9 mm smooth bore inspiratory tube 103 can offset a 29.1 mm corrugated expiratory tube 117 without a change in overall compressible volume of the breathing circuit, as compared to a nominal 22 mm corrugated inspiratory and expiratory circuit. The compressible volume of the 22 mm corrugated tubing using the trend line can be 380,132.7 mm³/m. The smooth bore inspiratory tube 103 can have a compressible volume of 93,664.1 mm³/m The compressible volume difference can be 286,468.6 mm³ between the standard tubing and the new smooth bore inspiratory tube 103. The corrugated expiratory tube 117 can have the total compressible volume which is the sum of the compressible volume of the corrugated tube having a nominal diameter of 22 mm and the compressible volume difference, e.g., 666,601.3 mm³/m. Additionally, as these are per meter values, it should be appreciated by one of skill that the length of the inspiratory and/or expiratory limb could additionally be increased relative to prior art limb lengths without increasing the overall compressible volume of the circuit, as described further herein.

As yet another non-limiting example discovered by Applicant, a corrugated tube having a nominal diameter of 10 mm may be substantially equivalent to a 7.8 mm smooth bore tube based on RTF, excluding the RTF of the heater wire, as determined using trend lines. It was discovered that a 7.8 mm smooth bore inspiratory tube 103 can offset an 11.8 mm corrugated expiratory tube 117 without a change in overall compressible volume of the breathing circuit, as compared to a nominal 10 mm corrugated inspiratory and expiratory circuit. The compressible volume of the 10 mm corrugated tubing using the trend line can be 78,539.8 mm³/m. The smooth bore inspiratory tube 103 can have a compressible volume of 47,523.4 mm³/m. The compressible volume difference can be 31,016.5 mm³/m between the standard tubing and the new smooth bore inspiratory tube 103. The corrugated expiratory tube 117 can have the total compressible volume which is the sum of the compressible volume of the corrugated tube having a nominal diameter of 10 mm and the compressible volume difference, e.g., 109,556.3 mm³/m. Additionally, as these are per meter values, it should be appreciated by one of skill that the length of the inspiratory and/or expiratory limb could additionally be increased relative to prior art limb lengths without increasing the overall compressible volume of the circuit, as described further herein.

As another example discovered by Applicant, a corrugated tube having a nominal diameter of 15 mm may be substantially equivalent to a 10.5 mm smooth bore tube based on RTF, excluding the RTF of the heater wire. It was discovered that a 10.5 mm smooth bore inspiratory tube 103 can offset an 18.5 mm corrugated expiratory tube 117 without a change in overall compressible volume of the breathing circuit, as compared to a nominal 15 mm corrugated inspiratory and expiratory circuit. The compressible volume of the 15 mm corrugated tubing using the trend line can be 176,714.6 mm³. The smooth bore inspiratory tube 103 can have a compressible volume of 85,910.6 mm³. The compressible volume difference can be 90,804.0 mm³ between the standard tubing and the new smooth bore inspiratory tube 103. The corrugated expiratory tube 117 can have the total compressible volume which is the sum of the compressible volume of the corrugated tube having a nominal diameter of 15 mm and the compressible volume difference, e.g., 267,518.6 mm³. Additionally, as these are per meter values, it should be appreciated by one of skill that the length of the inspiratory and/or expiratory limb could additionally be increased relative to prior art limb lengths without increasing the overall compressible volume of the circuit, as described further herein.

As yet another example discovered by Applicant, a corrugated tube having a nominal diameter of 22 mm may be substantially equivalent to a 16.9 mm smooth bore tube based on RTF, excluding the RTF of the heater wire. It was discovered that a 16.9 mm smooth bore inspiratory tube 103 can offset a 26.1 mm corrugated expiratory tube 117 without a change in overall compressible volume of the breathing circuit, as compared to a nominal 22 mm corrugated inspiratory and expiratory circuit. The compressible volume of the 22 mm corrugated tubing using the trend line can be 380,132.7 mm³/m. The smooth bore inspiratory tube 103 can have a compressible volume of 224,424.7 mm³/m. The compressible volume difference can be 155,708.0 mm³/m between the standard tubing and the new smooth bore inspiratory tube 103. The corrugated expiratory tube 117 can have the total compressible volume which is the sum of the compressible volume of the corrugated tube having a nominal diameter of 22 mm and the compressible volume difference, e.g., 535,840.7 mm³/m. Additionally, as these are per meter values, it should be appreciated by one of skill that the length of the inspiratory and/or expiratory limb could additionally be increased relative to prior art limb lengths without increasing the overall compressible volume of the circuit, as described further herein.

As another example discovered by Applicant, a corrugated tube having a nominal diameter of 15 mm may be substantially equivalent to a 6.7 mm smooth bore tube based on RTF, taking account of the RTF of the heater wire. It was discovered that a 6.7 mm smooth bore inspiratory tube 103 can offset a 20.1 mm corrugated expiratory tube 117 without a change in overall compressible volume of the breathing circuit, as compared to a nominal 15 mm corrugated inspiratory and expiratory circuit. Another example discovered by Applicant, a corrugated tube having a nominal diameter of 15 mm may be substantially equivalent to a 10.0 mm smooth bore tube based on RTF, taking account of the RTF of the heater wire. It was discovered that a 10.0 mm smooth bore inspiratory tube 103 can offset an 18.7 mm corrugated expiratory tube 117 without a change in overall compressible volume of the breathing circuit, as compared to a nominal 15 mm corrugated inspiratory and expiratory circuit. Another example discovered by Applicant, a corrugated tube having a nominal diameter of 15 mm may be substantially equivalent to an 11.7 mm smooth bore tube based on RTF, taking account of the RTF of the heater wire. It was discovered that an 11.7 mm smooth bore inspiratory tube 103 can offset a 17.7 mm corrugated expiratory tube 117 without a change in overall compressible volume of the breathing circuit, as compared to a nominal 15 mm corrugated inspiratory and expiratory circuit. Another example discovered by Applicant, a corrugated tube having a nominal diameter of 15 mm may be substantially equivalent to a 13.5 mm smooth bore tube based on RTF, taking account of the RTF of the heater wire. It was discovered that a 13.5 mm smooth bore inspiratory tube 103 can offset a 16.4 mm corrugated expiratory tube 117 without a change in overall compressible volume of the breathing circuit, as compared to a nominal 15 mm corrugated inspiratory and expiratory circuit. Additionally, as these are per meter values, it should be appreciated by one of skill that the length of the inspiratory and/or expiratory limb could additionally be increased relative to prior art limb lengths without increasing the overall compressible volume of the circuit, as described further herein.

The compressible volume of the 15 mm corrugated tubing using the trend line can be 176,714.6 mm³/m. The smooth bore inspiratory tube 103 can have a compressible volume of 34,820 mm³/m for a 6.7 mm inspiratory tube, 78,539.8 mm³ for a 10.0 mm inspiratory tube, 107,513.2 mm³/m for an 11.7 mm inspiratory tube, and 143,138.8 mm³/m for a 13.5 mm inspiratory tube. The compressible volume difference between the standard tubing and the new smooth bore inspiratory tube 103 can be 141,894.2 mm³/m for a 6.7 mm inspiratory tube, 98,174.8 mm³/m for a 10.0 mm inspiratory tube, 69,201.4 mm³/m for an 11.7 mm inspiratory tube, and 33,575 mm³/m for a 13.5 mm inspiratory tube. The corrugated expiratory tube 117 can have the total compressible volume which is the sum of the compressible volume of the corrugated tube having a nominal diameter of 15 mm and the compressible volume difference, e.g., 318,608.8 mm³/m for a 6.7 mm inspiratory tube, 274,889.4 mm³/m for a 10.0 mm inspiratory tube, 245,916.0 mm³/m for a 11.7 mm inspiratory tube, and 210,290.4 mm³/m for a 13.5 mm inspiratory tube. Additionally, as these are per meter values, it should be appreciated by one of skill that the length of the inspiratory and/or expiratory limb could additionally be increased relative to prior art limb lengths without increasing the overall compressible volume of the circuit, as described further herein.

As another example discovered by Applicant, a corrugated tube having a nominal diameter of 15 mm may be substantially equivalent to a 10.5 mm smooth bore tube based on RTF, excluding of the RTF of the heater wire. It was discovered that a 10.5 mm smooth bore inspiratory tube 103 can offset an 18.5 mm corrugated expiratory tube 117 without a change in overall compressible volume of the breathing circuit, as compared to a nominal 15 mm corrugated inspiratory and expiratory circuit, without a change in overall compressible volume of the breathing circuit, as compared to a nominal 15 mm corrugated inspiratory and expiratory circuit. Additionally, as these are per meter values, it should be appreciated by one of skill that the length of the inspiratory and/or expiratory limb could additionally be increased relative to prior art limb lengths without increasing the overall compressible volume of the circuit, as described further herein.

The compressible volume of the 15 mm corrugated tubing using the trend line can be 176,714.6 mm³/m. The smooth bore inspiratory tube 103 can have a compressible volume of 85,910.6 mm³/m for a 10.5 mm inspiratory tube. The compressible volume difference between the standard tubing and the new smooth bore inspiratory tube 103 can be 90,804.0 mm³/m for a 10.5 mm inspiratory tube. The corrugated expiratory tube 117 can have the total compressible volume which is the sum of the compressible volume of the corrugated tube having a nominal diameter of 15 mm and the compressible volume difference, e.g., 267,518.6 mm³/m for a 10.5 mm inspiratory tube. Additionally, as these are per meter values, it should be appreciated by one of skill that the length of the inspiratory and/or expiratory limb could additionally be increased relative to prior art limb lengths without increasing the overall compressible volume of the circuit, as described further herein.

As an example discovered by Applicant, there can be a RTF pressure versus inner diameter trend line for corrugated tubing at 5 L/min. Taking into account the heater wire, one possible equation representing this trend line as calculated by Applicant can be approximately, $y=2149322.2385x^{-4.4519}$, $R^2=0.9727$. Excluding the heater wire, one possible equation representing this trend line as calculated by Applicant can be approximately, $y=603928.0681x^{-4.4380}$, $R^2=0.9964$. As an example discovered by Applicant, there can be a nominal diameter versus RTF pressure of corrugated tubing at 5 L/min. Taking into account the heater wire, one possible equation representing this trend line as calculated by Applicant can be approximately, $y=26.0327x^{-0.2185}$, $R^2=0.9727$. Excluding the heater wire, one possible equation representing this trend line as calculated by Applicant can be approximately, $y=20.0518x^{-0.2245}$, $R^2=0.9964$. The ISO RTF limit for this flow rate is 0.9 cmH2O (88.25 Pa), and two thresholds are 9.78 mm with the heater wire, and 7.33 mm excluding the heater wire. As an example discovered by Applicant, there can be a RTF pressure versus inner diameter trend line for smooth bore tubing at 5 L/min, one possible equation representing this trend line as calculated by Applicant can be approximately, $y=15.3164x^{-0.2191}$, $R^2=0.9933$.

As another example discovered by Applicant, there can be a RTF pressure versus inner diameter trend line for corrugated tubing at 15 L/min. Taking into account the heater wire, one possible equation representing this trend line as calculated by Applicant can be approximately, $y=22141877.6970x^{-4.5927}$, $R^2=0.9780$. Excluding the heater wire, one possible equation representing this trend line as calculated by Applicant can be approximately, $y=64442935.7622x^{-5.5152}$, $R^2=0.9907$. As an example discovered by Applicant, there can be a nominal diameter versus RTF pressure of corrugated tubing at 15 L/min. Taking into account the heater wire, one possible equation representing this trend line as calculated by Applicant can be approximately, $y=38.8945x^{-0.2129}$, $R^2=0.9780$. Excluding the heater wire, one possible equation representing this trend line as calculated by Applicant can be approximately, $y=25.9216x^{-0.1796}$, $R^2=0.9907$. The ISO RTF limit is 0.9 cmH2O (88.25 Pa), and two thresholds are 14.98 mm with the heater wire, and 11.59 mm excluding the heater wire. As an example discovered by Applicant, there can be a RTF pressure versus inner diameter trend line for smoothbore tubing at 15 L/min, one possible equation representing this trend line as calculated by Applicant can be approximately, $y=27.3664x^{-0.3158}$, $R^2=0.9421$.

As yet another example discovered by Applicant, there can be a RTF pressure versus inner diameter trend line for corrugated tubing at 30 L/min. Taking into account the heater wire, one possible equation representing this trend line as calculated by Applicant can be approximately, $y=79343411.8635x^{-4.5906}$, $R^2=0.9657$. Excluding the heater wire, one possible equation representing this trend line as calculated by Applicant can be approximately, $y=528987202.1853x^{-5.8298}$, $R^2=0.9828$. As an example discovered by Applicant, there can be a nominal diameter versus RTF pressure of corrugated tubing at 30 L/min. Taking into account the heater wire, one possible equation representing this trend line as calculated by Applicant can be approximately, $y=50.3401x^{-0.2104}$, $R^2=0.9657$. Excluding the heater wire, one possible equation representing this trend line as calculated by Applicant can be approximately, $y=30.9550x^{-0.1686}$, $R^2=0.9828$. The ISO RTF limit is 0.9 cmH2O (88.25 Pa), and two thresholds are 19.61 mm with the heater wire, and 14.54 mm excluding the heater wire. As an example discovered by Applicant, there can be a RTF pressure versus inner diameter trend line for smoothbore tubing at 30 L/min, one possible equation representing this trend line as calculated by Applicant can be approximately, $y=26.9650x^{-0.2260}$, $R^2=0.8419$.

It was discovered that there were numerous advantages with the breathing circuit 100. As described herein, a larger nominal diameter corrugated expiratory tube 117 increases surface area and residence time, both increasing vapor diffusion when the expiratory tube is constructed of a material allowing for the migration of water molecules through the wall of the expiratory tube. When used in conjunction with a smooth wall inspiratory tube, the theoretical maximum nominal diameter of the corrugated expiratory tube 117 maintains the overall compressible volume of the total breathing circuit while having the advantage of increasing vapor diffusion during dwell time of the gases within the expiratory tube.

The breathing circuit is designed to match the RTF of the inspiratory tube 103 from a corrugated tube of a first nominal diameter to a smooth bore tube of a second diameter, the second diameter being smaller than the first diameter. The smooth bore tube of the second diameter has a smaller compressible volume than the corrugated tube of the first diameter, thereby creating a compressible volume allowance for the breathing circuit comprising the smooth bore tube of the smaller second diameter as the inspiratory limb. This allowance in compressible volume can be offset by a corrugated tube of a third nominal diameter as the expiratory limb, the third nominal diameter can be larger than the first nominal diameter. In comparison to a breathing circuit having an inspiratory limb with a corrugated tube of the first nominal diameter and an expiratory limb with a corrugated tube of the first nominal diameter, the modified breathing circuit has an inspiratory limb with a smooth bore tube of the second diameter and an expiratory limb with a corrugated tube of the third nominal diameter; the overall compressible volume between the breathing circuits is the same or lower and the RTF of the inspiratory limb is the same or lower. In some embodiments discovered by Applicant, the advantages are achievable through the expiratory limb having the corrugated tube of the third nominal diameter, the third nominal diameter being greater than the first nominal diameter.

In another example surprisingly discovered by Applicant, a nominal 13 mm corrugated inspiratory tube and a nominal 13 mm corrugated expiratory tube have a compressible volume when used together to form a breathing circuit. Taking the inspiratory limb, the corrugated inspiratory tube has a RTF which can be measured to provide an actual RTF or calculated to provide a theoretical RTF. The RTF of the 13 mm corrugated inspiratory tube can be substantially equivalent to a smooth bore inspiratory tube 103. The smooth bore inspiratory tube 103 has a smaller diameter than the corresponding 13 mm corrugated inspiratory tube. This reduction in diameter between the corrugated inspiratory tube and the smooth bore inspiratory tube 103 corresponds to a reduction in compressible volume of the inspiratory limb.

The inspiratory limb and the expiratory limb together form a breathing circuit. The nominal 13 mm corrugated inspiratory tube and the nominal 13 mm corrugated expiratory tube define a first total compressible volume for the breathing circuit. This first total compressible volume can be maintained or decreased in the modified breathing circuit with the smooth bore inspiratory tube 103. In the modified breathing circuit with the smooth bore inspiratory tube 103, the inspiratory limb has a reduction in compressible volume due to a reduction in the diameter of the tube. In the modified breathing circuit with the smooth bore inspiratory tube 103, the expiratory limb can be designed to have a larger nominal diameter. The larger nominal diameter of the expiratory limb has a larger compressible volume which offsets the reduction in compressible volume of the inspiratory limb in considering the total compressible volume for the breathing circuit. The reduction in compressible volume resulting from the use of the smooth bore inspiratory tube 103, thus, can accommodate the increase in compressible volume from the corrugated expiratory tube 117. The breathing circuit with the nominal 13 mm corrugated inspiratory tube and the nominal 13 mm corrugated expiratory tube has the same or lower overall compressible volume as the smooth bore inspiratory tube 103 and the corrugated expiratory tube 117. However, the inspiratory tube 103 has a smaller diameter than the corresponding inspiratory limb of the breathing circuit with the nominal 13 mm corrugated inspiratory tube and the corrugated expiratory tube 117 has a larger nominal diameter than the corresponding expiratory limb of the breathing circuit with the nominal 13 mm corrugated expiratory tube.

Different diameter tubing can be used with different patient populations. Further, the intended delivered or tidal volume can be varied even among the same or different diameter tubing, as well as within the same or different breathing circuits. In some embodiments, smaller diameter tubes can be used with neonatal and pediatric patients while larger diameter tubes can be used with adult patient. The modified breathing circuit can be suitable for treatment of patients having tidal volumes in the range of 50 ml to 300 ml. The modified breathing circuit can be suitable for treatment of patients having tidal volumes greater than or equal to 300 ml. The modified breathing circuit can be suitable for treatment of patients having tidal volumes less than or equal to 50 ml. The modified breathing circuit can be suitable for treatment of pediatric or adolescent patients. The modified breathing circuit can be suitable for treatment of adult patients. The modified breathing circuit can be suitable for treatment of neonatal patients.

The modified breathing circuit can be tested according to the standard ISO 5367:2014 (E) which is incorporated by reference in its entirety. For the adult patient category, the intended delivered volume is greater than or equal to 300 ml. For the pediatric category, the intended delivered volume is between 50 ml and 300 ml. For the neonatal category, the intended delivered volume is less than or equal to 50 ml. For the adult patient category, the flow resistance limit is 0.03 hPa/l/min/m (cmH20/l/min/m). For the pediatric patient category, the flow resistance limit is 0.06 hPa/l/min/m (cmH20/l/min/m). For the neonatal patient category, the flow resistance limit is 0.37 hPa/l/min/m (cmH20/l/min/m). For the adult patient category, the At flow is 30 l/min. For the pediatric patient category, the At flow is 15 l/min. For the neonatal patient category, the At flow is 2.5 l/min. Table 1 is reproduced below. The table below can describe the flow resistance limit per metre by patient category for breathing tubes supplied to be cut to length.

| Patient category | Intended delivered volume | Flow resistance limit hPa/l/min/m (cmH$_2$O/l/min/m) | At flow l/min |
|---|---|---|---|
| Adult | ≥300 ml | 0.03 | 30 |
| Paediatric | 50 ml < 300 ml | 0.06 | 15 |
| Neonatal | ≤50 ml | 0.37 | 2.5 |

NOTE:
See Annex E

In some advantageous configurations of the modified breathing circuit, the inspiratory tube 103 can have an inner diameter between 5 mm and 14.5 mm while the expiratory tube 117 can have a nominal inner diameter between 15 mm and 22 mm. In some advantageous configurations of the modified breathing circuit, the inspiratory tube 103 can have an inner diameter between 10 mm and 21 mm while the expiratory tube 117 can have a nominal inner diameter between 22 mm and 30 mm. In some advantageous configurations, the inspiratory tube 103 can have an inner diameter between 4 mm and 12 mm while the expiratory tube 117 can have a nominal inner diameter between 13 mm and 18 mm. In some advantageous configurations of the modified breathing circuit, the inspiratory tube 103 can have an inner diameter between 4 mm and 17 mm while the expiratory tube 117 can have a nominal inner diameter between 10.5 mm and 20.5 mm. In some advantageous configurations of the modified breathing circuit, the inspiratory tube 103 can have an inner diameter between 9.5 mm and 24 mm while the expiratory tube 117 can have a nominal inner diameter between 19 mm and 31.5 mm. In some advantageous configurations of the modified breathing circuit, the inspiratory tube 103 can have an inner diameter between 3 mm and 13 mm while the expiratory tube 117 can have a nominal inner diameter between 9.5 mm and 19 mm.

In some advantageous configurations of the modified breathing circuit, the inspiratory tube 103 can have an inner diameter between 4 mm and 8 mm while the expiratory tube 117 can have a nominal inner diameter between 11 mm and 15 mm. In some advantageous configurations of the modified breathing circuit, the inspiratory tube 103 can have an inner diameter between 5 mm and 9 mm while the expiratory tube 117 can have a nominal inner diameter between 18 mm and 22 mm. In some advantageous configurations, the inspiratory tube 103 can have an inner diameter between 9 mm and 13 mm while the expiratory tube 117 can have a nominal inner diameter between 27 mm and 31 mm. In some advantageous configurations of the modified breathing circuit, the inspiratory tube 103 can have an inner diameter between 6 mm and 10 mm while the expiratory tube 117 can have a nominal inner diameter between 10 mm and 14 mm. In some advantageous configurations of the modified breathing circuit, the inspiratory tube 103 can have an inner diameter between 8.5 mm and 12.5 mm while the expiratory tube 117 can have a nominal inner diameter between 16.5 mm and 20.5 mm. In some advantageous configurations of the modified breathing circuit, the inspiratory tube 103 can have an inner diameter between 15 mm and 19 mm while the expiratory tube 117 can have a nominal inner diameter between 24 mm and 28 mm.

The inspiratory tube 103 can have an inner diameter of between 1 mm and 30 mm, such as 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, or ranges incorporating any of the foregoing values such as 6 mm to 14 mm, 6 mm to 13 mm, 6 mm to 12 mm, 6 mm to 11 mm, 7 mm to 10 mm, 8 mm to 9 mm, 10 mm to 20 mm, 11 mm to 20 mm, 11 mm to 19 mm, 11 mm to 18 mm, 11 mm to 17 mm, 11 mm to 16 mm, 11 mm to 15 mm, 12 mm to 15 mm, 13 mm to 14 mm, 5 mm to 11 mm, 6 mm to 10 mm, 6 mm to 8 mm, 9 mm to 10 mm, etc. It also is possible for the inspiratory tube 103 to have an inner diameter of any value in between any of these values.

The inspiratory tube 103 can have an inner diameter in the range of 0 mm to 2 mm, 1 mm to 3 mm, 2 mm to 4 mm, 3 mm to 5 mm, 4 mm to 6 mm, 5 mm to 7 mm, 6 mm to 8 mm, 7 mm to 9 mm, 8 mm to 10 mm, 9 mm to 11 mm, 10 mm to 12 mm, 11 mm to 13 mm, 12 mm to 14 mm, 13 mm to 15 mm, 14 mm to 16 mm, 15 mm to 17 mm, 16 mm to 18 mm, 17 mm to 19 mm, 18 mm to 20 mm, 19 mm to 21 mm, 20 mm to 22 mm, 21 mm to 23 mm, 22 mm to 24 mm, 23 mm to 25 mm, 24 mm to 26 mm, 25 mm to 27 mm, 26 mm to 28 mm, 27 mm to 29 mm, 28 mm to 30 mm, etc. The inspiratory tube 103 can have an inner diameter in the range of 0 mm to 4 mm, 1 mm to 5 mm, 2 mm to 6 mm, 3 mm to 7 mm, 4 mm to 8 mm, 5 mm to 9 mm, 6 mm to 10 mm, 7 mm to 11 mm, 8 mm to 12 mm, 9 mm to 13 mm, 10 mm to 14 mm, 11 mm to 15 mm, 12 mm to 16 mm, 13 mm to 17 mm, 14 mm to 18 mm, 15 mm to 19 mm, 16 mm to 20 mm, 17 mm to 21 mm, 18 mm to 22 mm, 19 mm to 23 mm, 20 mm to 24 mm, 21 mm to 25 mm, 22 mm to 26 mm, 23 mm to 27 mm, 24 mm to 28 mm, 25 mm to 29 mm, 26 mm to 30 mm, etc. The inspiratory tube 103 can have an inner diameter in the range of 0 mm to 6 mm, 1 mm to 7 mm, 2 mm to 8 mm, 3 mm to 9 mm, 4 mm to 10 mm, 5 mm to 11 mm, 6 mm to 12 mm, 7 mm to 13 mm, 8 mm to 14 mm, 9 mm to 15 mm, 10 mm to 16 mm, 11 mm to 17 mm, 12 mm to 18 mm, 13 mm to 19 mm, 14 mm to 20 mm, 15 mm to 21 mm, 16 mm to 22 mm, 17 mm to 23 mm, 18 mm to 24 mm, 19 mm to 25 mm, 20 mm to 26 mm, 21 mm to 27 mm, 22 mm to 28 mm, 23 mm to 29 mm, 24 mm to 30 mm, etc. The inspiratory tube 103 can have an inner diameter in the range of 0 mm to 8 mm, 1 mm to 9 mm, 2 mm to 10 mm, 3 mm to 11 mm, 4 mm to 12 mm, 5 mm to 13 mm, 6 mm to 14 mm, 7 mm to 15 mm, 8 mm to 16 mm, 9 mm to 17 mm, 10 mm to 18 mm, 11 mm to 19 mm, 12 mm to 20 mm, 13 mm to 21 mm, 14 mm to 22 mm, 15 mm to 23 mm, 16 mm to 24 mm, 17 mm to 25 mm, 18 mm to 26 mm, 19 mm to 27 mm, 20 mm to 28 mm, 21 mm to 29 mm, 22 mm to 30 mm, etc. It also is possible for the inspiratory tube 103 to have an inner diameter of any value in between any of these values.

The expiratory tube 117 can have a nominal inner diameter of between 1 mm and 40 mm, such as 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or ranges incorporating any of the foregoing values such as 15.5 mm to 21 mm, 16 mm to 20 mm, 16 mm to 19 mm, 18 mm to 20 mm, 19 mm to 20 mm, 22 mm to 29 mm, 23 mm to 30 mm, 24 mm to 30 mm, 24 mm to 29 mm, 25 mm to 28 mm, 25.5 mm to 27 mm, 13 mm to 17 mm, 14 mm to 17 mm, 15 mm to 16.5 mm, 14 mm to 15 mm, etc. It also is possible for the expiratory tube 117 to have an inner diameter of any value in between any of these values.

The expiratory tube 117 can have an inner nominal diameter in the range of 0 mm to 2 mm, 1 mm to 3 mm, 2 mm to 4 mm, 3 mm to 5 mm, 4 mm to 6 mm, 5 mm to 7 mm, 6 mm to 8 mm, 7 mm to 9 mm, 8 mm to 10 mm, 9 mm to 11 mm, 10 mm to 12 mm, 11 mm to 13 mm, 12 mm to 14 mm, 13 mm to 15 mm, 14 mm to 16 mm, 15 mm to 17 mm, 16 mm to 18 mm, 17 mm to 19 mm, 18 mm to 20 mm, 19 mm to 21 mm, 20 mm to 22 mm, 21 mm to 23 mm, 22 mm to 24 mm, 23 mm to 25 mm, 24 mm to 26 mm, 25 mm to 27 mm, 26 mm to 28 mm, 27 mm to 29 mm, 28 mm to 30 mm, 29 mm to 31 mm, 30 mm to 32 mm, 31 mm to 33 mm, 32 mm to 34 mm, 33 mm to 35 mm, 34 mm to 36 mm, 35 mm to 37 mm, 36 mm to 38 mm, 37 mm to 39 mm, 38 mm to 40 mm, etc. The expiratory tube 117 can have an inner nominal diameter in the range of 0 mm to 4 mm, 1 mm to 5 mm, 2 mm to 6 mm, 3 mm to 7 mm, 4 mm to 8 mm, 5 mm to 9 mm, 6 mm to 10 mm, 7 mm to 11 mm, 8 mm to 12 mm, 9 mm to 13 mm, 10 mm to 14 mm, 11 mm to 15 mm, 12 mm to 16 mm, 13 mm to 17 mm, 14 mm to 18 mm, 15 mm to 19 mm, 16 mm to 20 mm, 17 mm to 21 mm, 18 mm to 22 mm, 19 mm to 23 mm, 20 mm to 24 mm, 21 mm to 25 mm, 22 mm to 26 mm, 23 mm to 27 mm, 24 mm to 28 mm, 25 mm to 29 mm, 26 mm to 30 mm, 27 mm to 31 mm, 28 mm to 32 mm, 29 mm to 33 mm, 30 mm to 34 mm, 31 mm to 35 mm, 32 mm to 36 mm, 33 mm to 37 mm, 34 mm to 38 mm, 35 mm to 39 mm, 36 mm to 40 mm, etc. The expiratory tube 117 can have an inner nominal diameter in the range of 0 mm to 6 mm, 1 mm to 7 mm, 2 mm to 8 mm, 3 mm to 9 mm, 4 mm to 10 mm, 5 mm to 11 mm, 6 mm to 12 mm, 7 mm to 13 mm, 8 mm to 14 mm, 9 mm to 15 mm, 10 mm to 16 mm, 11 mm to 17 mm, 12 mm to 18 mm, 13 mm to 19 mm, 14 mm to 20 mm, 15 mm to 21 mm, 16 mm to 22 mm, 17 mm to 23 mm, 18 mm to 24 mm, 19 mm to 25 mm, 20 mm to 26 mm, 21 mm to 27 mm, 22 mm to 28 mm, 23 mm to 29 mm, 24 mm to 30 mm, 25 mm to 31 mm, 26 mm to 32 mm, 27 mm to 33 mm, 28 mm to 34 mm, 29 mm to 35 mm, 30 mm to 36 mm, 31 mm to 37 mm, 32 mm to 38 mm, 33 mm to 39 mm, 34 mm to 40 mm, etc. The expiratory tube 117 can have an inner nominal diameter in the range of 0 mm to 8 mm, 1 mm to 9 mm, 2 mm to 10 mm, 3 mm to 11 mm, 4 mm to 12 mm, 5 mm to 13 mm, 6 mm to 14 mm, 7 mm to 15 mm, 8 mm to 16 mm, 9 mm to 17 mm, 10 mm to 18 mm, 11 mm to 19 mm, 12 mm to 20 mm, 13 mm to 21 mm, 14 mm to 22 mm, 15 mm to 23 mm, 16 mm to 24 mm, 17 mm to 25 mm, 18 mm to 26 mm, 19 mm to 27 mm, 20 mm to 28 mm, 21 mm to 29 mm, 22 mm to 30 mm, 23 mm to 31 mm, 24 mm to 32 mm, 25 mm to 33 mm, 26 mm to 34 mm, 27 mm to 35 mm, 28 mm to 36 mm, 29 mm to 37 mm, 30 mm to 38 mm, 31 mm to 39 mm, 32 mm to 40 mm, etc. It also is possible for the expiratory tube 117 to have an inner nominal diameter of any value in between any of these values.

The difference in diameter between the inspiratory tube 103 and the expiratory tube 117 can be between 0 mm and 20 mm, such as 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 11 mm, 12 mm, 13 mm, 14 mm, 15 mm, 16 mm, 17 mm, 18 mm, 19 mm, 20 mm, or ranges incorporating any of the foregoing values such as 0 mm to 2 mm, 1 mm to 3 mm, 2 mm to 4 mm, 3 mm to 5 mm, 4 mm to 6 mm, 5 mm to 7 mm, 6 mm to 8 mm, 7 mm to 9 mm, 8 mm to 10 mm, 9 mm to 11 mm, 10 mm to 12 mm, 11 mm to 13 mm, 12 mm to 14 mm, 13 mm to 15 mm, 14 mm to 16 mm, 15 mm to 17 mm, 16 mm to 18 mm, 17 mm to 19 mm, 18 mm to 20 mm, 0 mm to 4 mm, 1 mm to 5 mm, 2 mm to 6 mm, 3 mm to 7 mm, 4 mm to 8 mm, 5 mm to 9 mm, 6 mm to 10 mm, 7 mm to 11 mm, 8 mm to 12 mm, 9 mm to 13 mm, 10 mm to 14 mm, 11 mm to 15 mm, 12 mm to 16 mm, 13 mm to 17 mm, 14 mm to 18 mm, 15 mm to 19 mm, 16 mm to 20 mm, 0 mm to 6 mm, 1 mm to 7 mm, 2 mm to 8 mm, 3 mm to 9 mm, 4 mm to 10 mm, 5 mm to 11 mm, 6 mm to 12 mm, 7 mm to 13 mm, 8 mm to 14 mm, 9 mm to 15 mm, 10 mm to 16 mm, 11 mm to 17 mm, 12 mm to 18 mm, 13 mm to 19 mm, 14 mm to 20 mm, 0 mm to 8 mm, 1 mm to 9 mm, 2 mm to 10 mm, 3 mm to 11 mm, 4 mm to 12 mm, 5 mm to 13 mm, 6 mm to 14 mm, 7 mm to 15 mm, 8 mm to 16 mm, 9 mm to 17 mm, 10 mm to 18 mm, 11 mm to 19 mm, 12 mm to 20 mm, etc. The inner diameter of the inspiratory tube 103 can be less than the nominal inner diameter of the expiratory tube 117. It also is possible for the difference to be any value in between any of these values.

As another non-limiting but preferred example discovered by Applicant, a corrugated tube having a nominal diameter of 15 mm may be substantially equivalent to an 11.7 mm smooth bore tube based on RTF. It was discovered that an 11.7 mm smooth bore inspiratory tube 103 can offset a maximum 18.5 mm or 20.1 mm expiratory limb (with heater wire, or without, respectively). However, the Applicant has surprisingly discovery that a lower than maximum diameter of 14.5 mm used in a corrugated expiratory tube 117 still allows for the desired technical effect of no increase in the overall compressible volume of the breathing circuit, as compared to a nominal 15 mm corrugated inspiratory and expiratory circuit.

Moreover, in this preferred example, the length of the inspiratory and/or expiratory limb could additionally be increased relative to prior art or typical limb lengths without increasing the overall compressible volume of the circuit, as described further herein. Such increased length provides an additional technical benefit in that such a limb would have improved usability and improved patient mobility, particularly with respect to neonatal and pediatric patients that require kangaroo care or other care wherein the patient is held. In some embodiments, the inspiratory or expiratory conduit can be approximately 1.75 m as discussed below. The smooth bore inspiratory tube 103 accordingly to an embodiment of the invention can have a tube diameter of about 11.7 mm. The smooth bore inspiratory tube 103 can have a tube length of about 1.75 m. The smooth bore inspiratory tube 103 can have limb compressible volume of about 188,148 $mm^3$/m. The corrugated expiratory tube 117 can have a tube diameter of 14.5 mm. The corrugated expiratory tube 117 can have a tube length of about 1.75 m. The corrugated expiratory tube 117 can have limb compressible volume of about 288,977 $mm^3$/m. The total compressible volume for the smooth bore inspiratory tube 103 and the corrugated expiratory tube 117 is about 477,125 $mm^3$/m. The comparable standard tube would be 15 mm in diameter and 1.5 m in length. The standard tube is a dual corrugated circuit, typically designed for pediatric patients. For the standard tube, the inspiratory tube can have tube diameter of 15 mm and a tube length of 1.5 m. The standard inspiratory tube can have limb compressible volume of 265,072 $mm^3$. For the standard tube, the expiratory tube can have tube diameter of 15 mm and a tube length of 1.5 m. The standard expiratory tube can have limb compressible volume of 265,072 $mm^3$. The total compressible volume for the inspiratory tube and the expiratory tube of the standard circuit is 530,144 $mm^3$/m. As would be appreciated by one of skill in the art, as compared to the standard circuit, the improved circuit of this embodiment (i.e. 11.7 mm smooth-bore inspiratory and 14.5 corrugated expiratory) allows greater flow before hitting the ISO standardized resistance limit (increasing the upper size of patients able to be treated) of the 15 mm corrugated inspiratory limb and the overall circuit compressible volume is less than the 15 mm corrugated pair (allowing it to treat smaller tidal volume patients). Even further, the increased length over a 1.5 m limb increases usability for the patient and the carers, and improves mobility. The larger expiratory limb diameter, particularly for a breathable limb as disclosed herein, allows for increased residence time and therefore more breathing of humidity to ambient air (and away from the sensitive ventilator components which humidity may damage).

In some embodiments, the smooth bore inspiratory tube 103 can allow greater flow before hitting the resistance limit. In some embodiments, this result can increase the upper size of patients able to be treated. In some embodiments, the smooth bore inspiratory tube 103 can allow greater flow compared to the 15 mm corrugated standard tube. In some embodiments, the overall circuit compressible volume is less than the standard corrugated tube pair. In some embodiments, this result can allow the smooth bore inspiratory tube 103 and corrugated expiratory tube 117 to treat smaller tidal volume patients. In some embodiments, the smooth bore inspiratory tube 103 and corrugated expiratory tube 117 can advantageously allow greater flow before hitting the resistance limit compared to corresponding standard circuits. In some embodiments, the smooth bore inspiratory tube 103 and corrugated expiratory tube 117 can advantageously treat a greater range of patients by increasing the upper size of the patient able to be treated compared with the corresponding standard circuit. In some embodiments, the smooth bore inspiratory tube 103 and corrugated expiratory tube 117 can advantageously have a lower overall circuit compressible volume compared with the corresponding standard circuit. In some embodiments, the smooth bore inspiratory tube 103 and corrugated expiratory tube 117 can advantageously treat smaller tidal volume patients compared with the corresponding standard circuit.

The inspiratory tube 103 can have a length between 1 m and 4 m, such as 1.0 m, 1.05 m, 1.1 m, 1.15 m, 1.2 m, 1.25 m, 1.3 m, 1.35 m, 1.4 m, 1.45 m, 1.5 m, 1.55 m, 1.6 m, 1.65 m, 1.7 m, 1.75 m, 1.8 m, 1.85 m, 1.9 m, 1.95 m, 2.0 m, 2.05 m, 2.1 m, 2.15 m, 2.2 m, 2.25 m, 2.3 m, 2.35 m, 2.4 m, 2.45 m, 2.5 m, 2.55, 2.6 m, 2.65 m, 2.7 m, 2.75 m, 2.8 m, 2.85 m, 2.9 m, 2.95 m, 3.0 m, 3.1 m, 3.15 m, 3.2 m. 3.25 m, 3.3 m, 3.35 m, 3.4 m, 3.45 m, 3.5 m, 3.55 m, 3.6 m, 3.65 m, 3.7 m, 3.75 m, 3.8 m, 3.85 m, 3.9 m, 3.95 m, 4.0 m, or ranges incorporating any of the foregoing values. The expiratory tube 117 can have a length between 1 m and 4 m, such as 1.0 m, 1.05 m, 1.1 m, 1.15 m, 1.2 m. 1.25 m, 1.3 m, 1.35 m, 1.4 m, 1.45 m, 1.5 m, 1.55 m, 1.6 m, 1.65 m, 1.7 m, 1.75 m, 1.8 m, 1.85 m, 1.9 m, 1.95 m, 2.0 m, 2.05 m, 2.1 m, 2.15 m, 2.2 m, 2.25 m, 2.3 m, 2.35 m, 2.4 m, 2.45 m, 2.5 m, 2.55 m, 2.6 m, 2.65 m, 2.7 m, 2.75 m, 2.8 m, 2.85 m, 2.9 m, 2.95 m, 3.0 m, 3.1 m, 3.15 m, 3.2 m. 3.25 m, 3.3 m, 3.35 m, 3.4 m, 3.45 m, 3.5 m, 3.55 m, 3.6 m, 3.65 m, 3.7 m, 3.75 m, 3.8 m, 3.85 m, 3.9 m, 3.95 m, 4.0 m, or ranges incorporating any of the foregoing values. One of skill in the art would recognize that the total length of the inspiratory or expiratory conduit may be broken up into multiple sections to accommodate other equipment such as a water trap and/or an intermediate connector with one or more sensors, and/or a PCB, and/or a controller. It also is possible for the lengths to be any value in between any of these values.

In some embodiments, a lower compliance can allow for expanding the patient size range. In some embodiments, a lower compliance can allow the circuit to be longer, while still in an acceptable patient size range. In some embodiments, instead of a length of 1.1 to 1.5 m, the inspiratory and/or expiratory conduit can be longer, e.g., 1.55 m, 1.6 m, 1.65 m, 1.7 m, 1.75 m, 1.8 m, 1.85 m, 1.9 m, 1.95 m, 2.0 m, 2.05 m, 2.1 m, 2.15 m, 2.2 m, 2.25 m, 2.3 m, 2.35 m, 2.4 m, 2.45 m, 2.5 m, 2.55 m, 2.6 m, 2.65 m, 2.7 m, 2.75 m, 2.8 m, 2.85 m, 2.9 m, 2.95 m, 3.0 m, 1.6 m or longer, between 1.5 and 2.0 mm, preferably 1.75 m, preferably 2.0 m, or ranges incorporating any of the foregoing values. In some embodiments, a longer inspiratory and/or expiratory conduit can be a great benefit for patient mobility, particularly with respect to neonatal and pediatric patients that require kangaroo care or other care wherein the child is held. In some embodiments, the inspiratory or expiratory conduit can be less than 4 m.

As described herein, the testing investigated the difference in pneumatic properties of corrugated and smooth bore tubing used in breathing circuits to transport humidified gases to and from a patient. The testing investigated the pneumatic benefits of a combination of a smooth bore inspiratory limb and a corrugated expiratory limb over the conventional corrugated inspiratory and corrugated expiratory limbs for the three standard tubing sizes of 10 mm, 15 mm and 22 mm. In some embodiments, the breathing sets are non-water trapped, corrugated dual limb breathing sets that are for the purpose of delivering humidified gas, which can be heated.

The resistance to flow testing results demonstrated that for a given nominal diameter corrugated tube (10 mm, 15 mm and 22 mm), a smaller nominal diameter smooth bore inspiratory tube can be used to maintain the same resistance to flow (RTF) value. In some embodiments, a heater wire is used in the breathing circuit to maintain the temperature of the humidified gas to and from the patient, typically a spiral wound heater wire design is used in a corrugated inspiratory limb. The heater wire in the air path will increase the circuit's RTF. In some embodiments, the smooth bore inspiratory tubes can have the heater wire built into the wall of the tube which is outside of the air path, such that the heater wire has no effect of RTF. With this being taken consideration with respect to the RTF measurements, the size of a comparable smooth bore tube is further reduced.

As described herein, a smaller nominal diameter smooth bore inspiratory tube directly relates to a reduced compressible volume (compliance) of the inspiratory limb. This reduction in compressible volume can allow for a larger nominal diameter corrugated expiratory tube to be used while maintaining the equivalent overall breathing set compliance value. In some embodiments, a benefit of a greater expiratory limb surface area includes that there is more area in which vapour transfer (breathability) can occur. For a given standard breathing tubing size of 10 mm, 15 mm and 22 mm with corrugated inspiratory and exploratory tubes, the comparable smooth bore inspiratory and corrugated exploratory tube combinations are described herein. The testing investigated the three common standard sizes of breathing circuits, e.g., 10 mm, 15 mm and 22 mm breathing sets.

To deliver effective respiratory support to a patient there are some key pneumatic properties of a breathing set as described herein. Pneumatic compliance of the breathing set comprises the sum of the pneumatic compliance of all the components within the kit. Pneumatic compliance can be considered a measurement of the volume required to increase the pressure to a desired level in the breathing set. A low pneumatic compliance breathing set can require a smaller volume added than a high pneumatic compliance breathing set for a given change in pressure. Pneumatic compliance can directly impact the ventilator waveform delivery to the patient. In some methods of use, pneumatic compliance can be important to be maintained or reduced when treating a given patient population. Pneumatic compliance of a breathing tube can be broken into two main components—the compressible volume and the tube rigidity. The larger the internal volume of a circuit, then the greater the compressible volume will be. With a larger internal volume, there is a greater amount of air that needs to be compressed to raise the pressure. For example, for two steel tubes of the same length, one with an internal diameter of 10 mm and the other with an internal diameter of 20 mm, then the compressible volume of the 20 mm tube will be larger than the compressible volume of the 10 mm tube as the internal volume greater. The stiffer the tube wall, then the lower the compliance will be. With a stiffer tube, there will be less stretching, thus less air volume required to reach a given pressure. For example, for two tubes of the same length and same inner diameter, one is steel and the other rubber of the same wall thickness, the compressible volume of both the tubes is the same. However, the rubber tube can expand and increase its volume when the pressure is raised, leading to a higher change in volume and a higher compliance.

Resistance to flow (RTF) can be considered a measurement of how much pressure is required to allow a given flow rate of air through a tube. Resistance to flow is typically expressed as cmH2O/l/min. The main properties of the tube that impact the RTF include the tube diameter and surface roughness. In some embodiments, a larger, smooth tube is beneficial to reduce RTF. Resistance to flow can be an important pneumatic property for breathing circuits as it limits the size of the waveform/breath that is able to be delivered to a patient in a specified inspiratory time.

Nominal Diameter can be considered a characteristic of the tubes. Nominal diameter is a way of incorporating the difference in internal diameters of a corrugated tube. The nominal diameter can be calculated as: Nominal $\emptyset$=(Min $\emptyset$+max$\emptyset$)/2. For a smoothbore tube, Nominal Diameter is the internal diameter. For a corrugated tube, Nominal Diameter accounts for the corrugation height and size.

One purpose of the testing was to investigate the effect of smooth bore tubing on the pneumatic properties for a breathing circuit, in view of corrugated tubing over the range of tube sizes typically utilized in respiratory support therapies. Applicant discovered that compliance and resistance to flow were important properties to consider. RTF data was collected on a range of corrugated and smooth bore tubes. This resistance to flow testing provided various trend lines as described herein. At a given flow rate for a corrugated tube, an equivalent smooth bore tube that provides the same RTF value was identified using the trend lines created by plotting diameter (or nominal diameter) against pressure. This resistance to flow evaluation provided equivalent RTF between corrugated standard tubes and smooth bore inspiratory tubes. The compliance was calculated for comparable corrugated and smooth bore tubes. The difference between the compliance was calculated. This compliance comparison testing allowed the gains in compliance from the smooth bore tube to be investigated. The new expiratory limb compliance is the original corrugated compliance value plus the compliance variance found from the above calculation. A new maximum expiratory tube diameter can then be calculated form this new value. The expiratory limb compliance and tube sizing allows the difference in compliance from using a smooth bore inspiratory tube to be added to the compliance of the corrugated expiratory tube, thereby increasing the maximum size of the expiratory corrugated tube over the standard corrugated tube. Additionally, as the testing was all performed one tubes cut to 1 m lengths, one of skill in the art would appreciate that a larger expiratory diameter can be used up to the maximum values as calculated herein (that value being larger over the prior art expiratory diameters for that type of breathing circuit), and/or the inspiratory and/or expiratory tube can be made longer than the prior art breathing circuit lengths.

During the resistance to flow testing, a flow sweep was performed on each tube and the resistance to flow was determined over a flow rate between 1.2 and 70 l/min. The testing provided an understanding of the variance of RTF with several different commercially available and prototype individual tubes of both smooth bore and corrugated internal profiles of varied diameters (or nominal diameters). In some instances, the tests were conducted with a heater wire present in the bore, and in other cases, the tests were conducted without a heater wire present in the bore. The tubes were cut to a nominal length of 1 m. Accordingly, RTF values expressed herein are in units of $mm^3/m$. The results show that the resistance to flow curves for both the corrugated and smooth bore tube samples are similar. However comparing the similar sized nominal diameter corrugated and smooth bores tubes, it can be seen that the smooth bore tube has a lower RTF value for a given flow rate.

A relationship between resistance to flow values of the corrugated and smooth bore tubes was analyzed to determine, at a defined flow rate, the nominal diameter smooth bore tube that would produce an equivalent RTF value as the corrugated tube. For the testing, the flow rate was 5 l/min for a 10 mm tube. The flow rate was 15 l/min for a 15 mm tube. The flow rate was 30 l/min for a 22 mm tube.

The compliance values for the equivalent corrugated and smooth bore tubes can be compared to understand the pneumatic benefits of changing to a smooth bore tube. The breathing limbs compliance is made up of the compressible volume as well as the rigidity of the material. Many different materials can be considered. As described herein, the compressible volume aspect of the compliance was compared in the testing. The compressible volume can be determined in part by the internal area of the tubing. For a corrugated tube, the nominal diameter can be used. The compressible volume can be calculated for the corrugated, standard tube, as well as the smooth bore inspiratory tube. The difference in these values can also be calculated.

For a given breathing circuit kit including an inspiratory limb and expiratory limb, the benefits of a lower compliant smooth bore inspiratory limb means the expiratory limb can use a greater proportion of total kit compliance. The new maximum expiratory limb compliance can be the sum of the compressible volume difference and the standard corrugated expiratory limb's compliance. From this calculation, a new maximum nominal diameter can be determined for the expiratory limb.

The purpose of a heated humidified breathing circuit is to maintain the humidity in the gas from the chamber to the patient. A heater wire can be installed in the breathing tube to maintain the temperature and to reduce any humidity from condensing out along the tube. In some embodiments, the heater wire is a helically wound filament stretched down the length of the limb. The heater wire can have an impact of the RTF as it is a restriction to the flow. In some embodiments, smooth bore tubes can have an integrated heater wire in the wall. The integrated heater wire can be removed from the gas path, thus not impeding of the RTF.

For a given nominal diameter corrugated tube, a smaller nominal diameter inspiratory smooth bore tube can be used to maintain the same resistance to flow value. Additionally, if a spiral heater wire is considered in the resistance to flow measurements of the corrugated tube, the nominal diameter of a comparable smooth bore inspiratory tube can be even smaller to maintain the same resistance to flow value. As a direct result of having a smaller nominal diameter, the smooth bore inspiratory tube has a lower compressible volume compared to the counterpart standard corrugated tube. The smooth bore inspiratory tube can allow a greater proportion of the total breathing set compliance to be allocated to the expiratory limb, thereby enabling a larger surface area.

The circuit kit for use in respiratory therapy for a patient can include various features. The circuit kit includes a breathing circuit. The breathing circuit includes an inspiratory tube to receive the inspiratory gases flow from a gas source. The inspiratory tube includes an inspiratory inlet, an inspiratory outlet, and an inner wall enclosing an inspiratory central bore. The inner wall of the inspiratory tube is smooth. The breathing circuit includes an expiratory tube to receive an expiratory gases flow from a patient. The expiratory tube includes an expiratory inlet, an expiratory outlet, and an inner wall enclosing an expiratory central bore. The inner wall of the expiratory tube is corrugated. The circuit kit can include a y piece for coupling the inspiratory tube and the expiratory tube. The circuit kit can include a chamber for holding a quantity of water and locating on a humidifier. The circuit kit can include a dry line for conveying flow from a ventilator to other gas source to a humidifier inlet. The circuit kit may be used in a respiratory apparatus system which includes a gas source, such as a respiratory ventilator, and/or a humidifier. A system can include the circuit kit and a humidifier.

The circuit kit can have dimensions based, in part, on the patient population. The inspiratory tube can have an inner diameter between 5 and 14.5 mm and the expiratory tube can have a nominal inner diameter between 15 and 22 mm. The circuit kit can have dimensions based, in part, on the patient population. The inspiratory tube can have an inner diameter between 4 and 17 mm and the expiratory tube can have a nominal inner diameter between 10.5 and 20.5 mm. The inspiratory tube can have an inner diameter between 6 mm and 14 mm. The inspiratory tube can have an inner diameter between 6 mm and 13 mm. The inspiratory tube can have an inner diameter between 6 mm and 12 mm. The inspiratory tube can have an inner diameter between 6 mm and 11 mm. The inspiratory tube can have an inner diameter between 7 mm and 10 mm. The inspiratory tube can have an inner diameter between 8 mm and 9 mm. The expiratory tube can have a nominal inner diameter between 15.5 mm and 21 mm. The expiratory tube can have having a nominal inner diameter between 16 mm and 20 mm. The expiratory tube can have having a nominal inner diameter between 16 mm and 19 mm. The expiratory tube can have having a nominal inner diameter between 18 mm and 20 mm. The expiratory tube can have having a nominal inner diameter between 19 mm and 20 mm. The inspiratory tube can have an inner diameter between 6 mm and 10 mm. The inspiratory tube can have an inner diameter between 11 mm and 15 mm. The inspiratory tube can have an inner diameter between 9 mm and 13 mm. The inspiratory tube can have an inner diameter between 10 mm and 14 mm. The inspiratory tube can have an inner diameter between 7 mm and 13 mm. The inspiratory tube can have an inner diameter between 8 mm and 14 mm. The expiratory tube can have a nominal inner diameter between 11 mm and 15 mm. The expiratory tube can have a nominal inner diameter a nominal inner diameter between 12 mm and 16 mm. The expiratory tube can have a nominal inner diameter a nominal inner diameter between 14 mm and 18 mm. The expiratory tube can have a nominal inner diameter a nominal inner diameter between 16 mm and 20 mm. The expiratory tube can have a nominal inner diameter a nominal inner diameter between 13 mm and 19 mm. The expiratory tube can have a nominal inner diameter a nominal inner diameter between 14 mm and 20 mm The difference between the inner diameter of the inspiratory tube and the nominal diameter of the expiratory tube can be between 1 mm and 14 mm. The inner diameter of the inspiratory tube may be smaller than the nominal diameter of the expiratory tube by a value between 1 mm and 14 mm. The circuit kit can be suitable for treatment of patients having tidal volumes in the range of 50 ml to 300 ml. The circuit kit can be suitable for treatment of pediatric and adolescent patients.

The circuit kit can have dimensions based, in part, on the patient population. The inspiratory tube can have an inner diameter from between 10 and 21 mm and the expiratory tube can have a nominal inner diameter from between 22 and 30 mm. The inspiratory tube can have an inner diameter from between 9.5 and 24 mm and the expiratory tube can have a nominal inner diameter from between 19 and 31.5 mm. The inspiratory tube can have an inner diameter between 10 mm and 20 mm. The inspiratory tube can have an inner diameter between 11 mm and 20 mm. The inspiratory tube can have an inner diameter between 11 mm and 19 mm. The inspiratory tube can have an inner diameter between 11 mm and 18 mm. The inspiratory tube can have an inner diameter between 11 mm and 17 mm. The inspiratory tube can have an inner diameter between 11 mm and 16 mm. The inspiratory tube can have an inner diameter between 11 mm and 15 mm. The inspiratory tube can have an inner diameter between 12 mm and 15 mm. The inspiratory tube can have an inner diameter between 13 mm and 14 mm. The expiratory tube can have a nominal inner diameter between 22 mm and 29 mm. The expiratory tube can have a nominal inner diameter between 23 mm and 30 mm. The expiratory tube can have a nominal inner diameter between 24 mm and 30 mm. The expiratory tube can have a nominal inner diameter between 24 mm and 29 mm. The expiratory tube can have a nominal inner diameter between 25 mm and 28 mm. The expiratory tube can have a nominal inner diameter between 25.5 mm and 27 mm. The inspiratory tube can have an inner diameter between 11 mm and 15 mm. The inspiratory tube can have an inner diameter between 12 mm and 16 mm. The inspiratory tube can have an inner diameter between 18 mm and 22 mm. The inspiratory tube can have an inner diameter between 19 mm and 23 mm. The inspiratory tube can have an inner diameter between 10 mm and 16 mm. The inspiratory tube can have an inner diameter between 17 mm and 23 mm. The expiratory tube can have a nominal inner diameter between 25 mm and 29 mm. The expiratory tube can have a nominal inner diameter between 26 mm and 30 mm. The expiratory tube can have a nominal inner diameter between 20 mm and 24 mm. The expiratory tube can have a nominal inner diameter between 21 mm and 25 mm. The expiratory tube can have a nominal inner diameter between 24 mm and 30 mm. The expiratory tube can have a nominal inner diameter between 20 mm and 26 mm. The difference between the inner diameter of the inspiratory tube and the nominal diameter of the expiratory tube can be between 1 mm and 20 mm. The inner diameter of the inspiratory tube may be smaller than the nominal diameter of the expiratory tube by a value between 1 mm and 20 mm. The circuit kit can be suitable for treatment of patients having tidal volumes greater than 300 ml. The circuit kit can be suitable for treatment of adult patients.

The circuit kit can have dimensions based, in part, on the patient population. The inspiratory tube can have an inner diameter from between 4 and 12 mm and the expiratory tube can have a nominal inner diameter from between 13 and 18 mm. The inspiratory tube can have an inner diameter from between 3 and 13 mm and the expiratory tube can have a nominal inner diameter from between 9.5 and 19 mm. The inspiratory tube can have an inner diameter between 5 mm and 11 mm. The inspiratory tube can have an inner diameter between 6 mm and 10 mm. The inspiratory tube can have an inner diameter between 6 mm and 8 mm. The inspiratory tube can have an inner diameter between 9 mm and 10 mm. The expiratory tube can have a nominal inner diameter between 13 mm and 17 mm. The expiratory tube can have a nominal inner diameter between 14 mm and 17 mm. The expiratory tube can have a nominal inner diameter between 15 mm and 16.5 mm. The expiratory tube can have a nominal inner diameter between 14 mm and 15 mm. The inspiratory tube can have an inner diameter between 5 mm and 9 mm. The inspiratory tube can have an inner diameter between 6 mm and 10 mm. The inspiratory tube can have an inner diameter between 7 mm and 11 mm. The inspiratory tube can have an inner diameter between 8 mm and 12 mm. The inspiratory tube can have an inner diameter between 4 mm and 11 mm. The inspiratory tube can have an inner diameter between 6 mm and 12 mm. The expiratory tube can have a nominal inner diameter between 13 mm and 17 mm. The expiratory tube can have a nominal inner diameter between 12 mm and 16 mm. The expiratory tube can have a nominal inner diameter between 11 mm and 15 mm. The expiratory tube can have a nominal inner diameter between 14 mm and 18 mm. The expiratory tube can have a nominal inner diameter between 12 mm and 18 mm. The expiratory tube can have a nominal inner diameter between 10 mm and 16 mm. The difference between the inner diameter of the inspiratory tube and the nominal diameter of the expiratory tube can be between 1 mm and 14 mm. The inner diameter of the inspiratory tube may be smaller than the nominal diameter of the expiratory tube by a value between 1 mm and 14 mm. The circuit kit can be suitable for treatment of patients having tidal volumes less than or equal to 50 ml. The circuit kit can be suitable for treatment of neonatal patients.

The inspiratory tube or expiratory tube can have additional features. The inspiratory tube or expiratory tube can have a length between 1.5 m and 2.5 m. The inspiratory tube or expiratory tube can have having a length between 1.6 m and 2.5 m. That the total length of the inspiratory or expiratory tube may be broken up into multiple sections to accommodate other equipment such as a water trap and/or an intermediate connector with one or more sensors, and/or a PCB, and/or a controller. The inspiratory tube can enclose a heating element within the inspiratory central bore, or encapsulated within the inner wall. The expiratory tube can include a heating element. The expiratory tube can be breathable. The inner wall of the expiratory tube can be permeable to water vapor and substantially impermeable to liquid and bulk flow of the exhaled gases flowing there through. The inspiratory tube can include in longitudinal cross-section a plurality of bubbles each with a flattened surface forming at least part of the wall of the inspiratory central bore. A system can include the circuit kit and a humidifier.

FIG. 1A shows a breathing circuit 100, which can be similar to FIG. 1 described herein. Such a breathing circuit 100 can be a respiratory humidification circuit. The breathing circuit 100 includes one or more medical tubes. The breathing circuit 100 can include an inspiratory tube 103 and an expiratory tube 117.

Gases can be transported in the circuit 100 of FIG. 1A. Ambient gases flow from a gases source 105 to a humidifier 107. The humidifier 107 can humidify the gases. The gases source 105 can be a ventilator, a blower or fan, a tank containing compressed gases, a wall supply in a medical facility, or any other suitable source of breathing gases.

The humidifier 107 connects to an inlet 109 (the end for receiving humidified gases) of the inspiratory tube 103 via a port 111, thereby supplying humidified gases to the inspiratory tube 103. The gases flow through the inspiratory tube 103 to an outlet 113 (the end for expelling humidified gases) of the inspiratory tube 103, and then to a patient 101 through a patient interface 115 connected to the outlet 113. The expiratory tube 117 connects to the patient interface 115. The expiratory tube 117 returns exhaled humidified gases from the patient interface 115 to the gases source 105 or to the ambient atmosphere.

Gases can enter the gases source 105 through a vent 119. The blower of the fan 121 can cause gases to flow into the gases source 105 by drawing air or other gases through the vent 119. The blower or the fan 121 can be a variable speed blower or fan. An electronic controller 123 can control the blower or fan speed. In particular, the function of the electronic controller 123 can be controlled by an electronic master controller 125. The function can be controlled in response to inputs from the master controller 125 and a user-set predetermined required value (preset value) of pressure or blower or fan speed via a dial or other suitable input device 127.

The humidifier 107 comprises a humidification chamber 129. The humidifier chamber 129 can be configured to contain a volume of water 130 or other suitable humidifying liquid. The humidification chamber 129 can be removable from the humidifier 107. Removability allows the humidification chamber 129 to be more readily sterilized or disposed of after use. The humidification chamber 129 portion of the humidifier 107 can be a unitary construction or can be formed of multiple components that are joined together to define the humidification chamber. The body of the humidification chamber 129 can be formed from a non-conductive glass or plastics material. The humidification chamber 129 can also include conductive components. For instance, the humidification chamber 129 can include a highly heat conductive base (an aluminum base) configured to contact or be associated with a heater plate 131 on the humidifier 107 when the humidification chamber 129 is installed on the humidifier 107.

The humidifier 107 can include electronic controls. The humidifier 107 can include the electronic, analog or digital master controller 125. The master controller 125 can be a microprocessor-based controller executing computer software commands stored in associated memory. In response to the user-set humidity or temperature value input via a user input device 133 and other inputs, the master controller 125 determines when (or to what level) to energize the heater plate 131 to heat the volume of water 130 within the humidification chamber 129.

As discussed above, any suitable patient interface can be used for the patient interface 115. A temperature probe 135 can connect to the inspiratory tube 103 near the patient interface 115 or the temperature probe 135 can connect to the patient interface 115. The temperature probe 135 can be integrated into the inspiratory tube 103. The temperature probe 135 detects the temperature near or at the patient interface 115. A signal reflecting the temperature can be provided by the temperature probe 135 to the electronic, analog, or digital master controller 125. A heating element (not shown) can be used to adjust the temperature of the patient interface 115 to raise the temperature of the patient interface 115 above the saturation temperature, thereby reducing the opportunity for unwanted condensation. A heating element 145 can also be used to adjust the temperature of the inspiratory tube 103 to raise the temperature of the inspiratory tube 103 above the saturation temperature, thereby reducing the opportunity for unwanted condensation.

In FIG. 1A, exhaled humidified gases are returned from the patient interface 115 to the gases source 105 via the expiratory tube 117. The expiratory tube 117 can include a vapor permeable material, as described in greater detail below. The vapor permeable expiratory tube can be corrugated.

The expiratory tube 117 can have a temperature probe and/or heating element, as described above with respect to the inspiratory tube 103, to reduce the opportunity for condensation to reach the gases source 105. The expiratory tube 117 need not return exhaled gases to the gases source 105. The exhaled humidified gases can flow directly to ambient surroundings or to other ancillary equipment, such as an air scrubber/filter (not shown).

In FIG. 1A, the inspiratory tube 103 includes or comprises a conduit with a smooth bore. The smooth bore causes the inspiratory tube 103 to have a lower RTF than a conduit with comparable dimensions having a corrugated bore. A smooth bore reduces the resistance to flow such that the bore (i.e. diameter or cross-sectional area) can be reduced, which results in a lower compressible volume when compared to a corrugated tube having a similar resistance to flow. The inspiratory conduit can be a composite conduit. The composite conduit generally may be defined as a conduit comprising two or more distinct portions, or, more specifically, two or more components that are joined together to define the conduit. The composite conduit can be spirally wound. The composite conduit can be spirally wound in such a way that the two or more components are spirally intertwined or coupled side by side in a spiraling configuration.

The expiratory tube 117 includes or comprises a conduit having at least a portion that is vapor permeable. Vapor permeability facilitates humidity removal. At least the vapor permeable portion of the expiratory tube 117 can be corrugated. The corrugation can be on the inside of the tube. Corrugation increases the inner surface area of the tube. The amount of vapor that can be diffused through a vapor permeable material correlates to the surface area of the material in direct contact with the vapor. Corrugation also increases turbulent flow of gases within the expiratory tube. More turbulent flow means better mixing of the gases, thereby causing the water vapor to travel to the outer walls of the expiratory tube 117. More turbulent flow can increase localized residence time in the corrugations in the expiratory tube, which, when coupled with vapor permeability attributes, further improves humidity removal. Increased residence time in the corrugation also decreases the temperature of the gases swirling in the "pocket" of each corrugation relative to that of a comparably sized smooth bore tube, which increases the relative humidity of those gases relative to that of a comparably sized smooth bore tube. The increased relative humidity increases the vapor pressure gradient across the wall of the expiratory tube 117 relative to that of a comparably sized smooth bore tube, which in turn increases vapor diffusion through the wall of the corrugated expiratory tube relative to that of a comparably sized smooth bore tube.

A vapor permeable, corrugated conduit can be formed, at least in part, from a foamed or unfoamed polymer that is permeable to water vapor and substantially impermeable to liquid water and bulk flow of gases. The expiratory tube 117 can comprise a wall defining a space within the expiratory tube 117. At least a part of the wall can be formed of a vapor permeable foamed material configured to allow the transmission of water vapor but to substantially prevent the transmission of liquid water and bulk flow of gases. At least a part of the wall can be formed of an non-foamed extruded solid material that is permeable to water vapor and substantially impermeable to liquid water and bulk flow of gases.

A vapor permeable expiratory tube 117 can be formed from non-foam based materials. The non-foam based materials can include a helically-wrapped vapor permeable tape, or the non-foam based materials may be extruded in a continuous tube. Corrugation of the expiratory tube 117 can be accomplished using non-foam based materials. The non-foam based materials can include beads of varying diameters arranged in an alternating pattern to form a corrugated inner surface. Alternatively, the corrugations may be created in the tube by methods which are known in the art, such as moulding or stamping.

The inspiratory tube 103 includes a smooth bore conduit. The smooth bore conduit can be heated and insulated to minimize condensate creation and maximize humidity delivery. Decreased condensate formation within the inspiratory tube permits more vapor in humidified gases to be delivered to a patient. Several factors affect condensate creation within the inspiratory tube 103 including the inner bore diameter, the degree of inner bore smoothness, the level of tube insulation, the presence of heating elements 145 (such as wires and elements) associated with the tube 103, and the position of heating elements within the tube 103, whether heating elements are located within the inner bore of the tube 103 or within the wall of the tube 103. Specifically, decreasing the inner bore diameter of the inspiratory tube 103 increases gases velocity as gases travel through the inspiratory tube 103. Increasing the smoothness of the bore decreases turbulence and creates a more parabolic wavefront across the lumen. Therefore, decreasing the inner bore diameter and making the inner bore smooth causes the faster gases located near the center of the tube to transfer less heat to the slower gases located near the tube wall. A smooth bore tube also provides no pockets in which vapor could be trapped or condensate might pool, as a corrugated tube would have. The vapor carried by the gases is therefore encouraged to exit the tube and thus be delivered to the patient.

Increasing the degree of tube insulation reduces heat loss across the wall of the inspiratory tube 103, which maximizes humidity delivery and minimizes condensate formation. Adding increased insulation to the inspiratory tube 103 also makes the breathing circuit 100 more efficient by decreasing how hard a heating element must work to maintain a target temperature and humidity because the insulated tube will better maintain the temperature and absolute humidity of the gases as they travel through the tube.

Adding heating elements to the inspiratory tube 103 also maximizes humidification and decreases condensation. Positioning one or more heating elements within the wall of the inspiratory tube 103 maximizes humidification, minimizes condensate formation, and contributes to the efficiency of the inspiratory tube 103, the breathing circuit 100, or the humidification system. When located within the wall of the inspiratory tube 103, the heating element heats the wall while not directly heating the gases. Heating the wall reduces the relative humidity (heating gases increases the temperature, which reduces the relative humidity) of gases near the wall. Positioning the heating element 145 on the lumen side of an inner wall of the insulating "bubbles" (defined elsewhere) of an inspiratory tube 103 (described in greater detail below) can further reduce heat loss outward through the wall of the inspiratory tube 103, which in turn maximizes humidification while minimizing condensate creation.

The expiratory tube 117 can include a corrugated conduit to maximize vapor removal while minimizing condensate formation and increasing localized residence time in the corrugation. The expiratory tube 117 can include a vapor permeable conduit to maximize vapor removal while minimizing condensation formation. The expiratory tube 117 can include a corrugated, vapor permeable, and/or heated conduit to maximize vapor removal while minimizing condensate formation and increasing localized residence time in the corrugation. Decreased condensate formation within the expiratory tube 117 permits more vapor to diffuse across the wall of the expiratory tube 117. The presence of a heating element 155 can maintain the relative humidity of the gases below 100% (that is, maintain the gases temperature above the dewpoint saturation temperature). Positioning the heating element 155 near or within the wall of the expiratory tube 117 causes the heating element 155 to primarily heat the gases near the wall of the expiratory tube 117. Keeping the gases temperature near the wall of the expiratory tube 117 above dewpoint avoids or limits condensate formation. The inspiratory tube 103 and the expiratory tube 117 are described in even greater detail elsewhere in this specification.

It was realized that incorporating the inspiratory tube 103 with a smaller diameter, smooth bore conduit in conjunction with the expiratory tube 117 with a corrugated conduit allows the expiratory tube 117 to be larger in diameter and/or longer than otherwise would be possible while maintaining the overall system compressible volume. Additionally or alternatively, the combination of the smaller diameter, smooth bore inspiratory tube 103 and the larger diameter, corrugated expiratory tube 117 can maintain the overall pressure drop. Additionally or alternatively, the combination of the smaller diameter, smooth bore inspiratory tube 103 and the larger diameter, corrugated expiratory tube 117 can maintain the resistance to flow (RTF), of the breathing circuit 100 at a desirable level. Ordinarily, increasing the length of a conduit undesirably increases the compressible volume of the conduit, and therefore, the compressible volume of the overall breathing circuit. Ordinarily, increasing the length of a conduit undesirably increases the RTF of the conduit, and therefore, increases the RTF of the overall breathing circuit. On the other hand, when the conduit is vapor permeable, the increased length advantageously improves the conduit's ability to remove vapor from exhaled gases. It was discovered that the combination of the inspiratory tube 103 with a smaller diameter, smooth bore and the expiratory tube 117 with a corrugated, vapor-permeable, larger bore conduit increases the ability of the expiratory tube 117 to remove water vapor from the breathing circuit without increasing the overall system compressible volume, pressure drop, and/or RTF.

It was further realized that incorporating the inspiratory tube 103 with a smooth bore conduit in conjunction with the expiratory tube 117 with a corrugated conduit allows the humidifier 107 to increase humidity performance providing a therapeutic benefit to patients, while driving closer to fully saturated gases, without adding the risk of liquid damage to the gases source 105 or condensate draining back to patient.

The inspiratory tube 103 with a smooth bore, spiral wound conduit can be paired with the expiratory tube 117 with a corrugated, vapor permeable conduit. As discussed above, the smooth bore of the inspiratory tube 103 has lower RTF than a similarly sized corrugated bore. It can also have a smaller internal diameter than a corrugated conduit. Ordinarily, decreasing internal diameter reduces compressible volume and undesirably increases the inspiratory tube's RTF. Nevertheless, the smooth bore characteristics can be selected such that the reduction in RTF associated with the smooth bore of the inspiratory tube 103 outweighs the RTF increase resulting from the smaller internal diameter of the inspiratory tube 103. This selection of a smaller diameter inspiratory tube 103 also reduces the compressible volume of the inspiratory tube 103. This selection then allows the corrugated expiratory tube 117 paired with the smooth bore inspiratory tube 103 to be longer without increasing the overall system pressure drop and/or compressible volume. The increased length of the expiratory tube 117 ordinarily undesirably increases the RTF and compressible volume of the tube. However, the increased length also improves the ability of the vapor permeable tube to remove vapor from expiratory gases. In this arrangement, pairing the smooth bore inspiratory tube 103 with the corrugated expiratory tube 117 enhances the performance of the expiratory tube 117. The system pressure drop of a breathing circuit as may exist from ventilator outlet to ventilator inlet can be affected by the pressure characteristics (RTF) of each element in the circuit. Referring back to FIG. 1A, assuming the pressure characteristics of the supply tube from ventilator to humidifier, humidifier chamber, interface tube, and interface body are fixed, the primary factors contributing to system pressure drop are the resistance to flow and dimensions (length and diameter) of the inspiratory tube 103 and the expiratory tube 117. Any change to one of these factors should advantageously be balanced by other factor(s) to avoid increasing the system pressure drop, RTF and/or compressible volume. As described herein, the primary factors contributing to compressible volume are the tube profile, extensibility, and dimensions (length and diameter or cross-sectional area) of the inspiratory tube 103 and the expiratory tube 117. There can be a tradeoff between decreasing the compressible volume of the inspiratory tube 103 and increasing the compressible volume of the expiratory tube 117 while maintaining the compressible volume of the breathing circuit. As described herein, increasing the compressible volume of the expiratory tube 117 has advantages in in vapor permeability in the expiratory limb.

The smooth bore of the inspiratory tube 103 can reduce resistance to flow (as compared to a corrugated inspiratory tube), decreasing the overall system pressure drop. This allows any or all of the other three factors (resistance to flow of the corrugated expiratory tube 117 or dimensions of either tube) to be altered in a way that increases the system pressure drop. The internal diameter of the inspiratory tube 103 can be smaller than the comparable corrugated inspiratory tube, which desirably increases the velocity of the gases flowing through the inspiratory tube 103. However, the smaller diameter also adds back some resistance to flow. So long as the RTF increase caused by the smaller diameter is sufficiently smaller than the RTF decrease caused by the use of the smooth bore, the length of the corrugated expiratory tube 117 can be increased without increasing the system pressure drop. Increasing the length of the expiratory tube 117 increases the surface area of the tube wall of the expiratory tube 117. The amount of vapor that can be diffused through a vapor permeable material is correlated to the surface area of the material. Increasing the length of the expiratory tube 117 increases the surface area of the wall of the expiratory tube 117 and also increases the residence time of gases in the expiratory tube 117. The amount of vapor that can be diffused through a permeable material is also correlated to the length of time the vapor-carrying gases are in contact with the material.

The compressible volume of the breathing circuit (the cumulative volume of the entire gases flow path) can also be balanced in the same way. For instance, a change in dimensions (cross-sectional area or diameter, length) of the inspiratory tube 103 can offset a change in dimensions (cross-sectional area or diameter, length) of the corrugated expiratory tube 117. As described herein, the decrease in diameter of the inspiratory tube 103 can decrease compressible volume. This decrease in compressible volume can improve accuracy of the delivered tidal volume. As described herein, the decrease in diameter of the inspiratory tube 103 can offset an increased diameter and/or an increased length of the expiratory tube 117. As described herein, the change in dimensions of the expiratory tube 117 can facilitate the function of the expiratory tube 117, such as by increasing vapor permeability of the expiratory tube 117. Altering tube dimensions affects both the system pressure drop and the system compressible volume, so both equations should advantageously be balanced or selected simultaneously when making changes. Reducing the diameter of the inspiratory tube 103 can both increase resistance to flow and decrease compressible volume, while increasing the average gases velocity through the tube. Adding to the length of the corrugated expiratory tube 117 both increases resistance to flow and increases compressible volume. Table 1 (above) summarizes the impacts of various features on these two system metrics:

Pairing the corrugated expiratory tube 117 with the smooth bore inspiratory tube 103 enables higher performance of the inspiratory tube 103. Pairing the larger diameter expiratory tube 117 with the smaller bore inspiratory tube 103 can be net neutral for compressible volume, but increase functionality of the breathing circuit (e.g., increase vapor diffusion in the expiratory tube 117). In this arrangement, the smooth bore inspiratory tube 103 minimizes condensate creation, and therefore maximizes humidity delivery. The overall compressible volume can be decreased by changes in dimensions, such as diameter and length of the inspiratory tube 103 and the expiratory tube 117. In some arrangements, the inspiratory tube 103 is insulated, which helps to make the humidifier 107 and/or a heating element, such as heater plate 131, more efficient in producing humidity that is delivered to the patient 101. The heater plate 131 does not have to work as much because it does not have to produce a high target temperature at the humidification chamber port 111, and this is because the heated and insulated inspiratory tube 103 will better maintain the absolute humidity of the gases flowing from the humidification chamber port 111 and through the inspiratory tube 103.

The location of a heater wire 145 in the wall of the inspiratory tube 103 also increases the efficiency of the inspiratory tube 103 in maintaining the relative humidity of the gas. The heater wire can heat the wall of the inspiratory tube 103, not the gases flowing through the lumen of the inspiratory tube 103, which reduces the relative humidity of the gases near the wall of the inspiratory tube 103. When the inspiratory tube 103 includes a composite conduit with a spiral wound hollow body or "bubble" tube (described in greater detail below), the heater wire 145 is under (on the lumen side of an inner wall) the insulating bubble, which reduces heat loss outward through the wall of the inspiratory tube 103.

The smooth bore inspiratory tube 103 promotes laminar gases flow, which creates a more parabolic wavefront across the lumen of the inspiratory tube 103, with the gases closer to the center of the lumen having a higher velocity relative to gases closer to the wall of the inspiratory tube 103. In this arrangement, the higher velocity gases have less time during transit from the inlet 109 to the outlet 113 to transfer heat to neighboring lower velocity gases. Combined with the inward direction of the heat generated by the heater wire, this arrangement helps to further increase the heat retained by the gases flow.

The smooth bore inspiratory tube 103 also provides no pockets in which vapor could be trapped or condensate might pool, as a corrugated tube would have. The vapor carried by the gases is therefore encouraged to remain in vapor phase and exit the inspiratory tube 103 and thus be delivered to the patient 101.

The corrugated expiratory tube 117 maximizes vapor removal and minimizes condensate formation. The expiratory tube 117 can be vapor permeable which promotes diffusion of vapor through the wall of the expiratory tube 117 to the outside atmosphere. In some arrangements, the expiratory tube 117 is vapor permeable and heated, the control of the heating along the tube promotes diffusion of vapor through the wall of the expiratory tube 117 to the outside atmosphere. Vapor transferred to the outside atmosphere will not be delivered to the gases source 105. The corrugated expiratory tube 117 creates turbulence in the portion of the gases flow adjacent the wall of the expiratory tube 117, which increases the residence time of gases adjacent the wall in the corrugations. Increased residence time increases the opportunity for vapor diffusion through the wall of the expiratory tube 117. Increased residence time also decreases the temperature of the gases swirling in the "pocket" of each corrugation, which increases the relative humidity of those gases. The increased relative humidity increases the vapor pressure gradient across the wall of the expiratory tube 117, which in turn increases vapor diffusion through the wall.

As discussed below, the expiratory tube 117 can include a heater wire 155 coiled near the center of the lumen of the expiratory tube 117. The heater wire, so positioned, adds to the turbulence of the gases flow while minimizing condensate formation. More turbulence means better mixing of the gases, thereby causing the water vapor to travel to the outer walls of the expiratory tube 117. The corrugated expiratory tube 117 also provides corrugation "pockets" that have the advantage of collecting any liquid that condenses from vapor. Liquid pooled in the corrugations is liquid not delivered to the gases source 105. In other arrangements, the heater wire can be positioned in the wall of an expiratory tube. The presence of a heater wire 155 in the expiratory tube 117 also minimizes condensate formation within the expiratory tube.

The combination of the smooth bore inspiratory tube 103 with the corrugated expiratory tube 117 allows the humidifier 107 to increase humidity performance. There is a contribution from the patient and bias flow in both invasive and non-invasive ventilation. In both, the expiratory tube 117 can function to decrease the amount of humidity returned to the gases source 105. The function of the expiratory tube 117 can be to sufficiently reduce the amount of humidity returned to the gases source 105.

The function of the expiratory tube can enable the humidifier 107 and the inspiratory tube 103 to deliver higher levels of humidity to the patient 101. If the expiratory tube 117 could not sufficiently reduce the amount of humidity returned to the gases source 105, the ability of the humidifier 107 and the inspiratory tube 103 to deliver higher levels of humidity to the patient 101 would have to be reduced or dialed back, because some of that extra humidity would be carried through the expiratory tube 117 to the gases source 105.

The inspiratory tube 103 and the expiratory tube 117 are discussed in further detail below.

Inspiratory Tubes

Figure 2A:
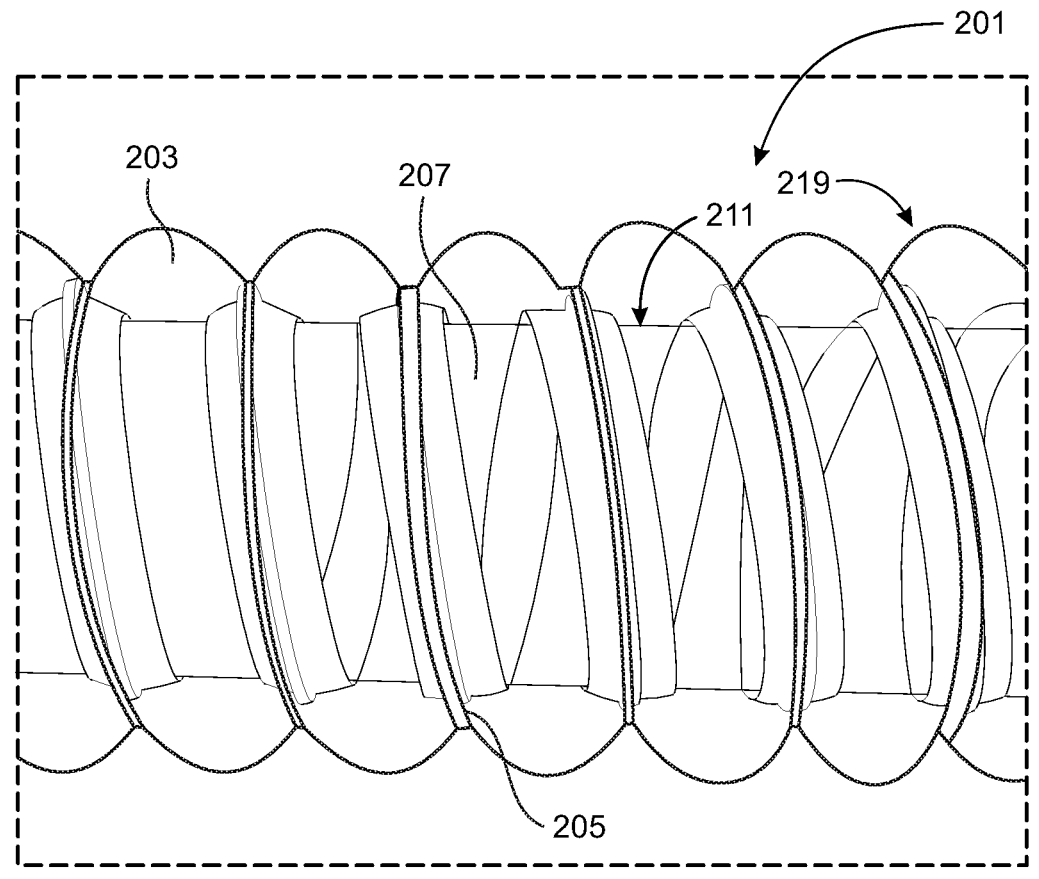
FIG. 2A is a side view of a portion of a composite tube.
Figure 2B:
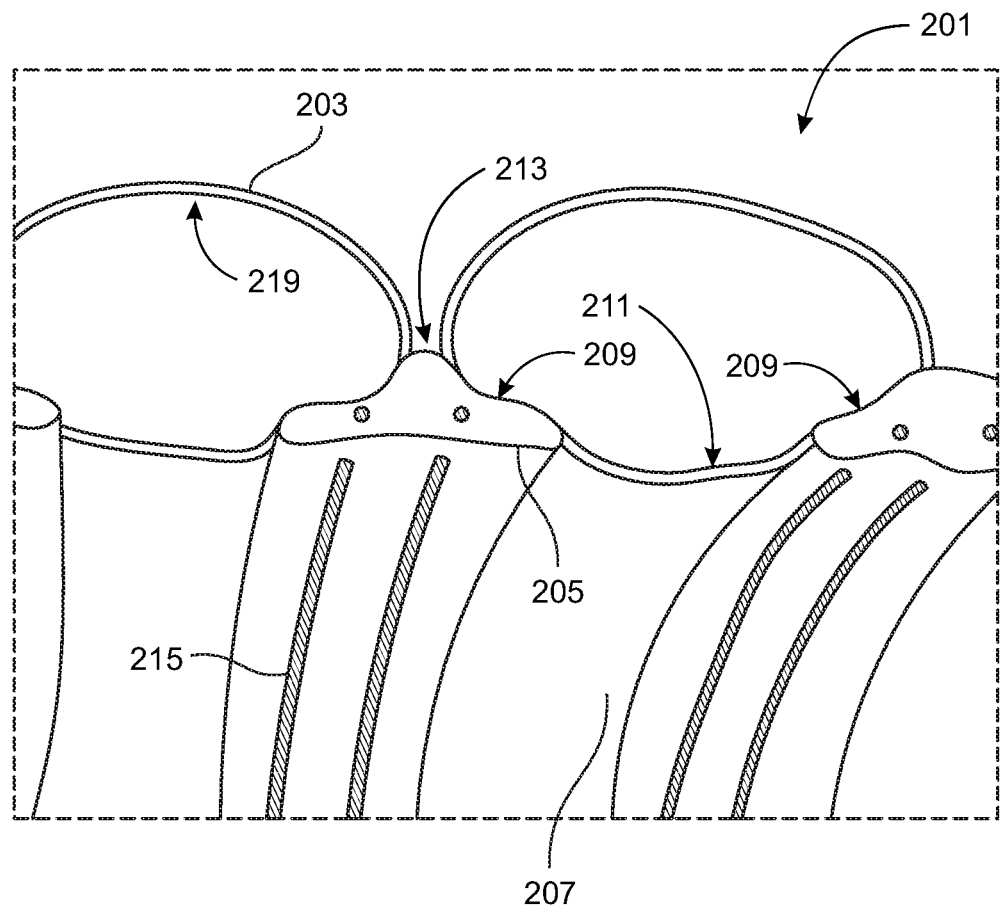
FIG. 2B is a longitudinal cross-section of the composite tube of FIG. 2A.

FIG. 2A shows a side plan view of a section of a conduit 201 of an inspiratory tube. In general, the conduit 201 comprises a first elongate member 203 and a second elongate member 205. Member is a broad term and is to be given its ordinary and customary meaning to a person of ordinary skill in the art (i.e., it is not to be limited to a special or customized meaning) and includes, without limitation, integral portions, integral components, and distinct components. The first elongate member 203 has a "bubble" profile, while the second elongate member 205 is a structural supporting or reinforcement member which adds structural support to the hollow body. As used herein, any reference to "bubble" means a an elongate hollow body that, in cross-section, has a shape defined by a wall with a hollow space within. Such shapes could include an oval or "D" shape, with reference to FIG. 2B. Such shapes could include, without limitation, "O" shapes, and other regular and irregular shapes, symmetric and asymmetric. In this description, the term "bubble" can refer to the cross-sectional shape of an elongated wind or turn of the first elongate member 203, taken in transverse cross-section through the wind or turn, for example as shown in FIG. 2B. The hollow body and the structural supporting member can have a spiral configuration, as described herein. The conduit 201 may be used to form the inspiratory tube 103 as described above, a coaxial tube as described below, or any other tubes as described elsewhere in this disclosure.

The first elongate member 203 can comprise a hollow body spirally wound to form, at least in part, an elongate tube having a longitudinal axis LA-LA and a lumen 207 extending along the longitudinal axis LA-LA. A portion 211 of the first elongate member 203 forms at least part of the inner wall of the lumen 207. The first elongate member 203 can be a tube. Preferably, the first elongate member 203 is flexible. Flexible refers to the ability to bend. Furthermore, the first elongate member 203 is preferably transparent or, at least, semi-transparent or semi-opaque. A degree of optical transparency allows a caregiver or user to inspect the lumen 207 for blockage or contaminants or to confirm the presence of moisture (i.e., condensation). A variety of plastics, including medical grade plastics, are suitable for the body of the first elongate member 203. Suitable materials include Polyolefin elastomers, Polyether block amides, Thermoplastic co-polyester elastomers, EPDM-Polypropylene mixtures, and Thermoplastic polyurethanes.

The hollow body structure of the first elongate member 203 contributes to the insulating properties of the conduit 201. An insulating conduit is desirable because, as explained above, it prevents heat loss. This can allow the conduit 201 to deliver gases from the humidifier 107 to the patient 101 while maintaining the conditioned state of the gases with minimal energy consumption.

The second elongate member 205 is also spirally wound and joined to the first elongate member 203 between adjacent turns of the first elongate member 203. The second elongate member 205 forms at least a portion of the lumen 207 of the elongate tube. The second elongate member 205 acts as structural support for the first elongate member 203. The second elongate member 205 can be wider at the base (proximal the lumen 207) and narrower at the top. The second elongate member can be generally triangular in shape, generally T-shaped, or generally Y-shaped. However, any shape that meets the contours of the corresponding first elongate member 203 is suitable.

Preferably, the second elongate member 205 is flexible, to facilitate bending of the tube. Desirably; the second elongate member 205 is less flexible than the first elongate member 203. This improves the ability of the second elongate member 205 to structurally support the first elongate member 203. The second elongate member 205 can be solid or mostly solid.

The second elongate member 205 can encapsulate or house conductive material, such as filaments, and specifically filaments used to generate heat or to carry information from sensors (not shown). Heating elements can comprise filaments, can minimize the cold surfaces onto which condensate from moisture-laden gases can form. Heating elements can also be used to alter the temperature profile of gases in the lumen 207 of the conduit 201. A variety of polymers and plastics, including medical grade plastics, are suitable for the body of the second elongate member 205. Suitable materials include Polyolefin elastomers, Polyether block amides, Thermoplastic co-polyester elastomers, EPDM-Polypropylene mixtures and Thermoplastic polyurethanes. The first elongate member 203 and the second elongate member 205 may be made from the same material.

FIG. 2B shows a longitudinal cross-section of a top portion of the conduit 201 of FIG. 2A. FIG. 2B has the same orientation as FIG. 2A. The first elongate member 203 can have a hollow-body shape. The first elongate member 203 can form in longitudinal cross-section a plurality of hollow bubbles. Portions 209 of the first elongate member 203 overlap adjacent wraps of the second elongate member 205. A portion 211 of the first elongate member 203 forms at least part of the wall of the lumen 207 (tube bore). Adjacent bubbles can be separated by a gap 213. A T-shaped second elongate member 205, as shown in FIG. 2B, can help maintain a gap 213 between adjacent bubbles.

The first elongate member 203 forms in longitudinal cross-section a plurality of hollow bubbles.

One or more conductive materials can be disposed in the second elongate member 205 for heating or sensing the gases flow. Two heating elements 215 can be encapsulated in the second elongate member 205, one on either side of the vertical portion of the "T." The heating element 215 comprise conductive material, such as alloys of Aluminum (Al) and/or Copper (Cu), or conductive polymer. Preferably, the material forming the second elongate member 205 is selected to be non-reactive with the metal in the heating element 215 when the heating elements 215 reach their operating temperature. The heating elements 215 may be spaced away from the lumen 207 so that the elements are not exposed to the lumen 207. At one end of the composite tube, pairs of elements can be formed into a connecting loop. A plurality of filaments can be disposed in the second elongate member 205.

Table 2 shows some non-limiting sample dimensions of two different composite conduits described herein, one for use with infants and the other for use with adults, as well as some non-limiting sample ranges for these dimensions. The dimensions refer to a transverse cross-section of a tube. In these tables, lumen diameter represents the inner diameter of a tube. Pitch represents the distance between two repeating points measured axially along the tube, namely, the distance between the tip of the vertical portions of adjacent "T"s of the second elongate member 205. Bubble width represents the width (maximum outer diameter) of a bubble. Bubble height represents the height of a bubble from the tube lumen. Bead height represents the maximum height of the second elongate member 205 from the tube lumen (e.g., the height of the vertical portion of the "T"). Bead width represents the maximum width of the second elongate member 205 (e.g., the width of the horizontal portion of the "T"). Bubble thickness represents the thickness of the bubble wall.

TABLE 2

| Feature | Infant | | Adult | |
|---|---|---|---|---|
| | Dimension (mm) | Range (±) | Dimension (mm) | Range (±) |
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 2.4 | 1 |
| Bubble height | 2.8 | 1 | 3.5 | 0.5 |
| Bead width | 0.9 | 0.5 | 1.5 | 0.5 |
| Bubble thickness | 0.4 | 0.35 | 0.2 | 0.15 |

Tables 3 and 4 show properties of a composite tube as described herein (labeled "A") having a heating element integrated inside the second elongate member 205. For comparison, properties of a Fisher & Paykel model RT100 disposable corrugated tube (labeled "B") having a heating element helically wound inside the bore of the tube are also presented.

Measurement of resistance to flow (RTF) was carried out according to Annex A of ISO 5367:2000(E). This publication prescribes a normative list of apparatus, procedure steps, and units in which to express the results of testing resistance to flow by measurement of pressure increase at a rated flow through a breathing tube. It includes variances for testing a breathing tube supplied ready for use or a 1 m length breathing tubing supplied to be cut to length, as well as a variance for testing each limb individually of a dual limb circuit that includes a pair of breathing tubes integrally connected to a Y-piece. The result of the test is the difference between the pressure measured in a reservoir with and without the breathing tube attached to the opening of the reservoir.

The results are summarized in Table 3. As seen below, the RTF for the composite tube is lower than the RTF for the comparably sized model RT100 tube.

TABLE 3

| | RTF (cm H₂O) | | | |
|---|---|---|---|---|
| Flow rate (L/min) | 3 | 20 | 40 | 60 |
| A | 0 | 0.05 | 0.18 | 0.38 |
| B | 0 | 0.28 | 0.93 | 1.99 |

Condensate or "rainout" within the tube refers to the weight of condensate collected per day at 20 L/min gases flow rate and room temperature of 18° C. Humidified air flows through the tube continuously from a chamber. The tube weights are recorded before and after each day of testing. Three consecutive tests are carried out with the tube being dried in between each test. The results are shown below in Table 4. The results showed that rainout is significantly lower in the composite tube than in the comparably sized model RT100 tube.

TABLE 4

| Tube | A (Day 1) | A (Day 2) | A (Day 3) | B (Day 1) | B (Day 2) | B (day 3) |
|---|---|---|---|---|---|---|
| Weight before (g) | 136.20 | 136.70 | 136.70 | 111.00 | 111.10 | 111.10 |
| Weight after (g) | 139.90 | 140.00 | 139.20 | 190.20 | 178.80 | 167.10 |
| Condensate weight (g) | 3.7 | 3.3 | 2.5 | 79.20 | 67.70 | 56.00 |

A composite tube 201 can comprise one or more heating filaments 215 placed within the gas path. Heating filaments can be emplaced on the lumen wall (tube bore) in a spiral configuration. One or more heating filaments 215 can be disposed on the lumen wall through bonding, embedding, or otherwise forming a heating filament on a surface of the second elongate member 205 that, when assembled, forms the lumen wall. Thus, the method can comprise disposing one or more heating filaments 215 on the lumen wall.

Additional details regarding composite conduits suitable the inspiratory tube 103 are disclosed in the specification and drawings of U.S. patent application Ser. No. 14/123,485, published as U.S. Patent Application Publication No. 2014/

0202462 A1 and U.S. patent application Ser. No. 14/649,801, published as U.S. Patent Application Publication No. 2015/0306333 A1, which have been incorporated herein by reference in their entirety for all that they contain.

Expiratory Tubes

As explained above with respect to FIG. 1, breathing circuits can make use of vapor permeable (that is, breathable) expiratory tubes to handle expired gases having high levels of relative humidity. Breathability is desirable to increase vapor diffusion and thus prevent rain out (condensation) in these components. Accordingly, breathing circuits can include vapor permeable expiratory tubes. In general, an expiratory tube comprises an inlet (for receiving expiratory gases), an outlet (for expelling the received gases), and an enclosing wall defining at least one gases passageway between said inlet and said outlet, wherein at least a part of said enclosing wall is of a vapor permeable material allowing the transmission of water vapor but substantially preventing the transmission of liquid water and bulk flow of breathing gases. The expiratory tube can be terminated by a first connector at the inlet and a second connector at the outlet, and only one gases passageway is provided the length between said inlet connector and said outlet connector.

Because of its breathability or vapor permeability, the wall forms a water vapor pathway from the gases space within the tube to the region on the other side of the wall, which may be ambient air. Preferably, the vapor permeable part(s) of the enclosing wall are formed of a foamed material. The tube can comprise an extruded corrugated conduit.

Expiratory tubes including vapor permeable, foamed polymers advantageously have been found to be both breathable and strong. An expiratory tube can comprise a wall defining a space within and wherein at least a part of said wall is of a vapor permeable foamed material, which allows the transmission of water vapor from gases within the space, but prevents the transmission of liquid water. The entire enclosing wall can be formed of the foamed material. Preferably, the wall is also impermeable to bulk flow of gases within the space, including breathing gases. Because of its vapor permeability, the wall forms a water vapor pathway from the gases space to the region on the other side of the wall.

Figure 3A:
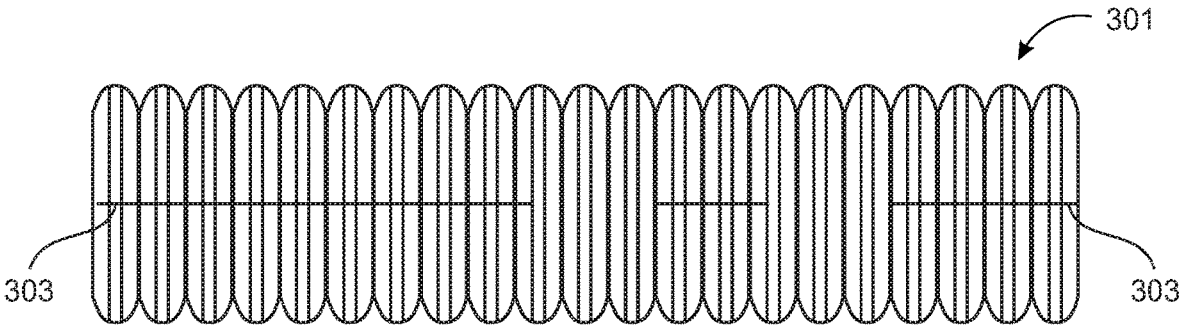
FIG. 3A is a side-plan view of a portion of a tube incorporating a vapor permeable foamed polymer material.
Figure 3B:
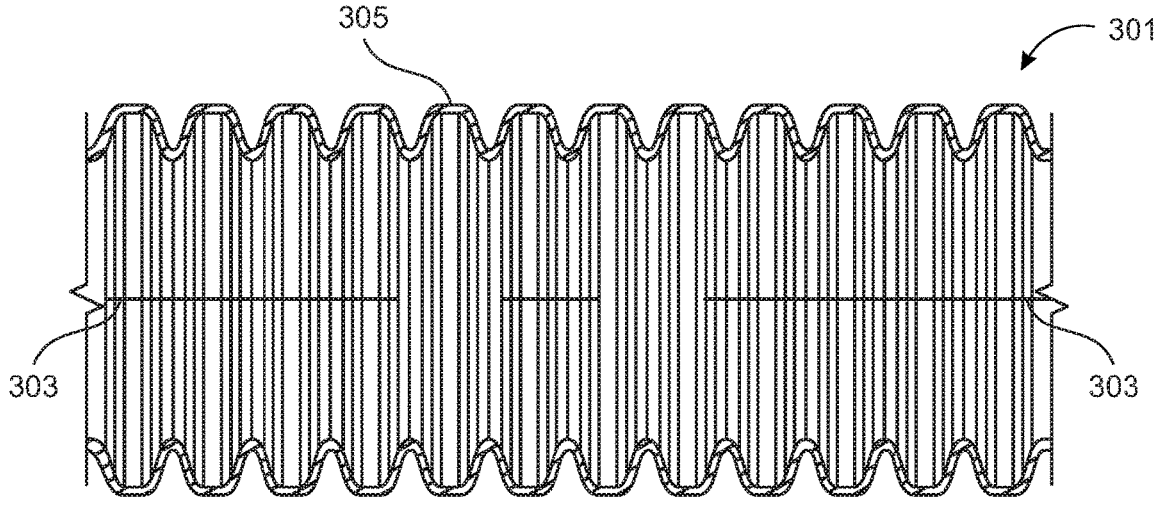
FIG. 3B is cross section view of the tube of FIG. 3A.

Reference is next made to FIGS. 3A and 3B, which show a conduit 301 of an expiratory tube. FIG. 3A shows a side view of the conduit 301, while FIG. 3B shows cross-section of the conduit 301 along the same side view as FIG. 3A. In both FIG. 3A and FIG. 3B, the horizontal axis is indicated as line 303-303. The conduit wall, shown as wall 305 in FIG. 3B is a vapor permeable foamed material. As shown in the figures, the conduit 301 is corrugated. The tube wall, shown as wall 305 in FIG. 3B is a breathable foamed material, as described above.

Because a tube is a type of component, the particulars of the component discussed above are applicable to the tube discussed here. At least a part of the enclosing wall can be comprise a breathable foamed material allowing the transmission of water vapor but substantially preventing the transmission of liquid water and bulk flow of breathing gases. The tube can be an extruded corrugated tube. The medical circuit tube can be used as a breathing tube or conduit or a tube or conduit for a limb of an insufflation system. For instance, the tube can be an expiratory breathing tube or an exhaust conduit, respectively. The tube can also be part of a patient interface. The conduit 301 may be used to form the expiratory tube 117 as described above, a coaxial tube as described below, or any other tubes as described elsewhere in this disclosure.

By incorporating highly breathable or vapor permeable foamed or unfoamed material, components can be manufactured having both a relatively high flexural stiffness and a high breathability. Because of their high vapor permeability (breathability), the foamed polymers allow water vapor to diffuse through them rapidly. This reduces the build-up of condensation within the expiratory tube by transmitting water vapor from the humidified gases within the expiratory tube to the surrounding ambient air or to other drier gases on the other side of the component. Yet, the components formed from these foamed polymers are also stiff, self-supporting, crush resistant, or semi-rigid, have relatively high resistance to crushing and resistance to buckling and even may not require additional reinforcement. The foamed polymers are useful for forming medical circuit components because the foamed polymer allow the transmission of water vapor from gases, but prevent the transmission of liquid water. They are also substantially impermeable to bulk flow of gas, such that they can be used to form components for delivering humidified gases. Foamed polymers can be selected such that the "bulk" properties (thickness, material, material blending, elastic modulus, breathability, and/or bulk stiffness) meet the requirements of the ISO 5367:2000(E) standard (namely, the test for increase in flow resistance) without extra reinforcement, and yet are vapor permeable. ISO 5367:2000(E) is hereby incorporated in its entirety by this reference.

Preferably, the foamed polymer is a vapor permeable foamed thermoplastic polymer. The vapor permeable thermoplastic polymer can be a foamed thermoplastic elastomer (or TPE as defined by ISO 18064:2003(E)), such as (1) a copolyester thermoplastic elastomer (e.g., ARNITEL®, which is a copolyester thermoplastic elastomer with a polyether soft segment, or other TPC or TPC-ET materials as defined by ISO 18064:2003(E)), or (2) a polyether block amide (e.g., PEBAX®, which is a polyamide thermoplastic elastomer with a polyether soft segment, or other TPA-ET materials as defined by ISO 18064:2003(E)), or (3) a thermoplastic polyurethane (TPU material as defined by ISO 18064:2003(E)), or (4) a foamed polymer blend, such as a TPE/polybutylene terephthalate (PBT, e.g., DURANEX® 500FP) blend. It has been found that the vapor permeable TPE ARNITEL® VT 3108 can be particularly suited to foaming and forming components. For this material, the breathability-to-strength relationship can be significantly improved by foaming the material as it is formed into a product or component. If the breathable thermoplastic polymer is a foamed TPE/PBT blend, the blend preferably comprises between 80% and 99% (or about 80% and 99%) TPE by weight and 20% and 1% (or about 20% and 1%) PBT by weight. The void fraction of the foamed material can be greater than 25% (or about 25%), such as between 25 and 60% (or about 25 and 60%), or between 30 and 50% (or about 30 and 50%). The foamed material can be structured such that no more than 5% (or about 5%) of the voids of the foamed material exceed a diameter of 500 μm.

It was discovered that the combined permeability and modulus for all the previously known materials did not exceed line 201, representing the formula: $\ln(P)=0.019(\ln(M))^2-0.7\ln(M))+6.5$ in which P represents permeability of the material in g·mm/m2/day, measured according to ASTM E96 Procedure A (desiccant method at a temperature of 23° C. and a relative humidity of 90%), and M represents the Young's modulus of the material in MPa.

The breathing circuit can comprise an expiratory tube comprising corrugated and/or vapor permeable materials that are not foam based. In some non-limiting arrangements, the inner wall of the expiratory tube can comprise a helically-wrapped vapor permeable tape, or the non-foam based materials may be extruded in a continuous tube. In some arrangements, the inner wall of the expiratory tube comprises a series of beads of varying diameters. Beads of different diameters can be arranged along the inner wall of the expiratory tube to create a corrugated pattern. Alternatively, the corrugations may be created in the tube by methods which are known in the art, such as moulding or stamping.

The wall can also include at least one reinforcing rib stiffening the wall or at least one region where the wall is locally thickened to stiffen the wall. The tube can include a plurality of reinforcing ribs arranged about the enclosing wall. These ribs can be co-extruded with the tube to be generally aligned with the longitudinal axis of the tube. Preferably, there are three to eight reinforcing ribs, and more particularly, three to five reinforcing ribs.

Figure 4A:
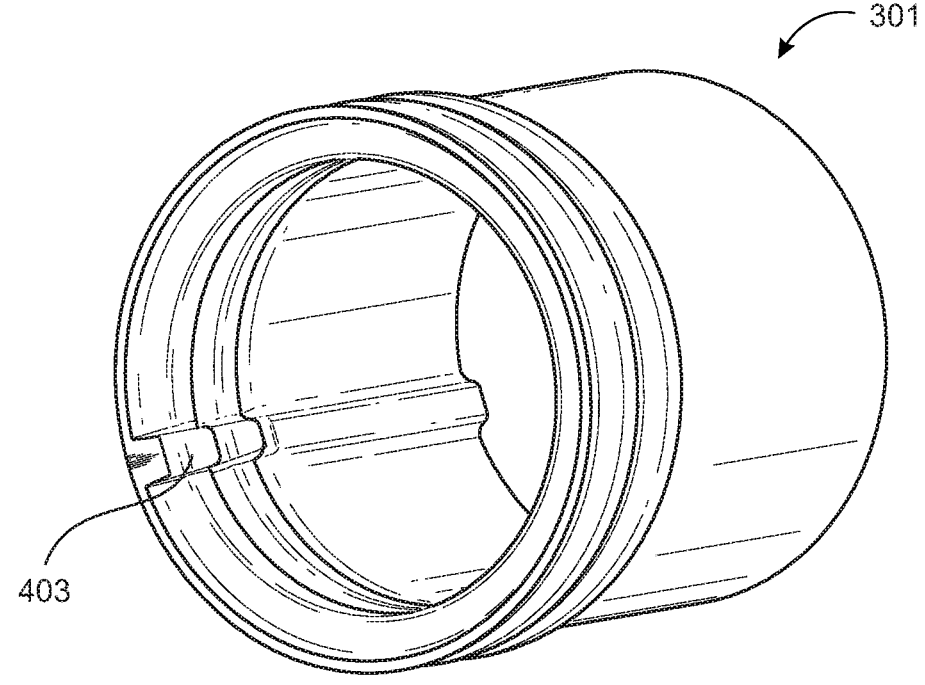
FIG. 4A is a front-perspective view of a portion of a tube incorporating integral, reinforcing ribs, wherein the tube is partially corrugated.
Figure 4B:
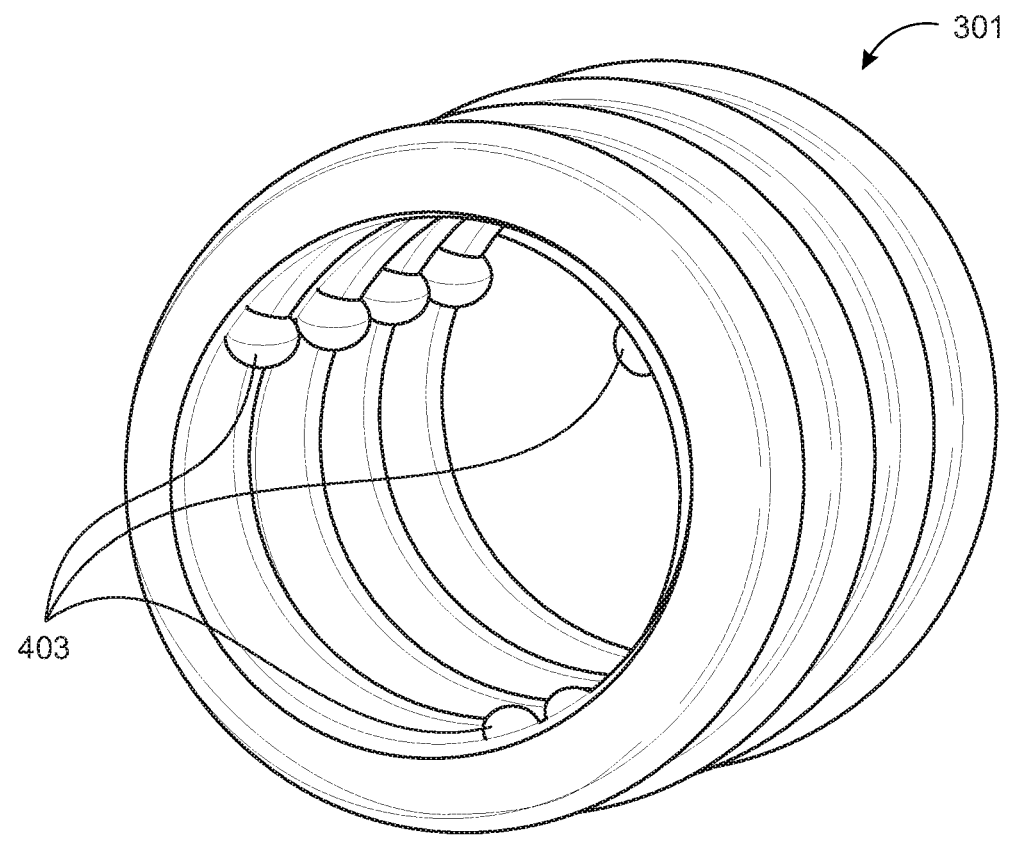
FIG. 4B is a front perspective view of a portion of the tube of FIG. 4A, wherein the tube is fully corrugated.

Reference is next made to FIGS. 4A and 4B, which show a portion of the conduit 301 that can be used to form the expiratory tube 117. The conduit 301 can be manufactured from a foamed vapor permeable material, as described herein. The conduit 301 further includes a plurality of reinforcing ribs 403 that can be co-extruded with the conduit 301. The ribs 403 can be formed from the same foamed polymer as the conduit 301. Alternatively, the ribs 403 can be made from a different material than the conduit 301. This can be achieved by co-extrusion. As shown in FIG. 4A, the conduit 301 can be extruded with the ribs 403 in place, and then corrugated to form the "dotted" structure shown in FIG. 4B. The conduit 301 can comprise between three and eight reinforcing ribs, such as between three and five reinforcing ribs In particular, the ribs can be arranged about the circumference of the tube shape. The ribs can be circumferentially arranged about the inner surface of the tube shape. The ribs can be generally longitudinally aligned along a length of the tube shape between the inlet and the outlet.

Figure 5A:
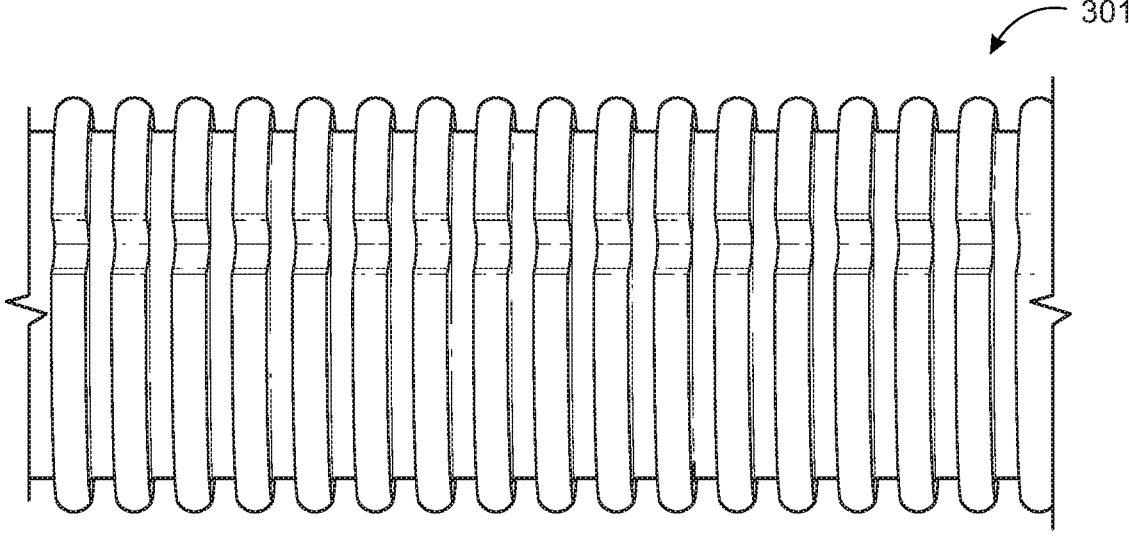
FIG. 5A is a front-perspective view of a portion of a tube incorporating ribs.
Figure 5B:
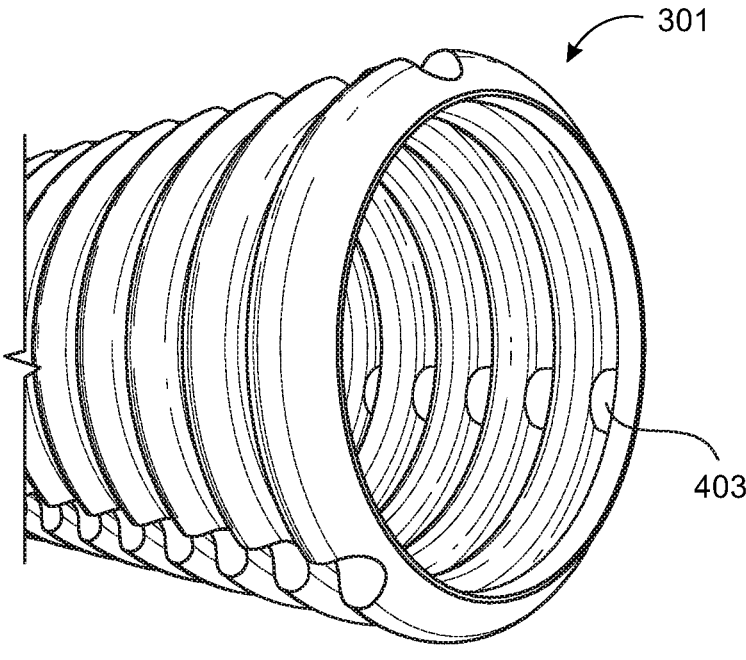
FIG. 5B is a front-perspective view of the tube of FIG. 5A.

Reference is next made to FIGS. 5A and 5B, which show a configuration for the corrugated, ribbed, vapor permeable conduit 301. In FIG. 5 the raised ribs 403 are visible in the space between the ridges in the inside of the conduit 301.

Figure 6:
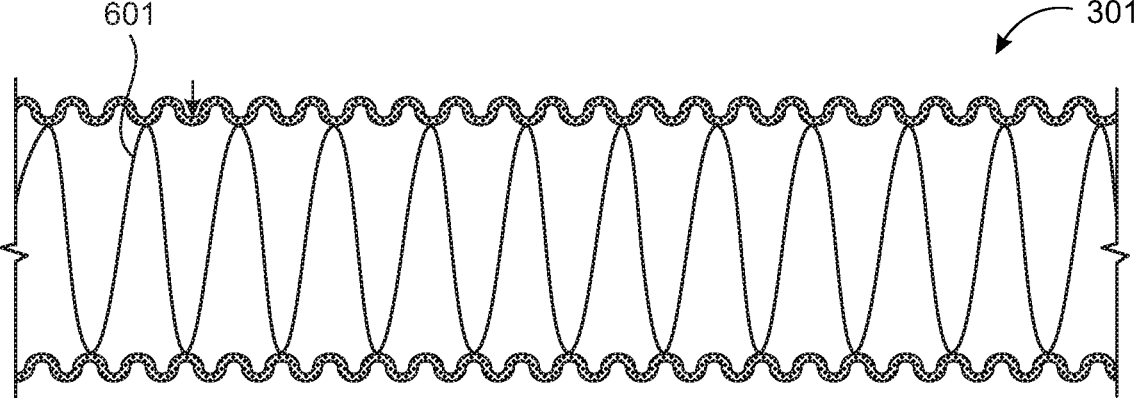
FIG. 6 is a schematic illustration of a portion of an expiratory tube.
Figure 7:
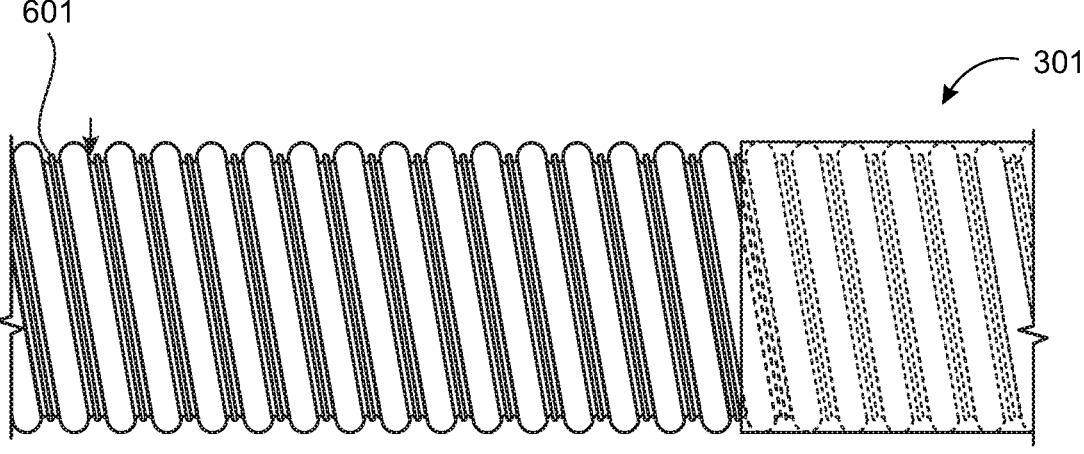
FIG. 7 is a schematic illustration of a portion of an expiratory tube.
Figure 8:
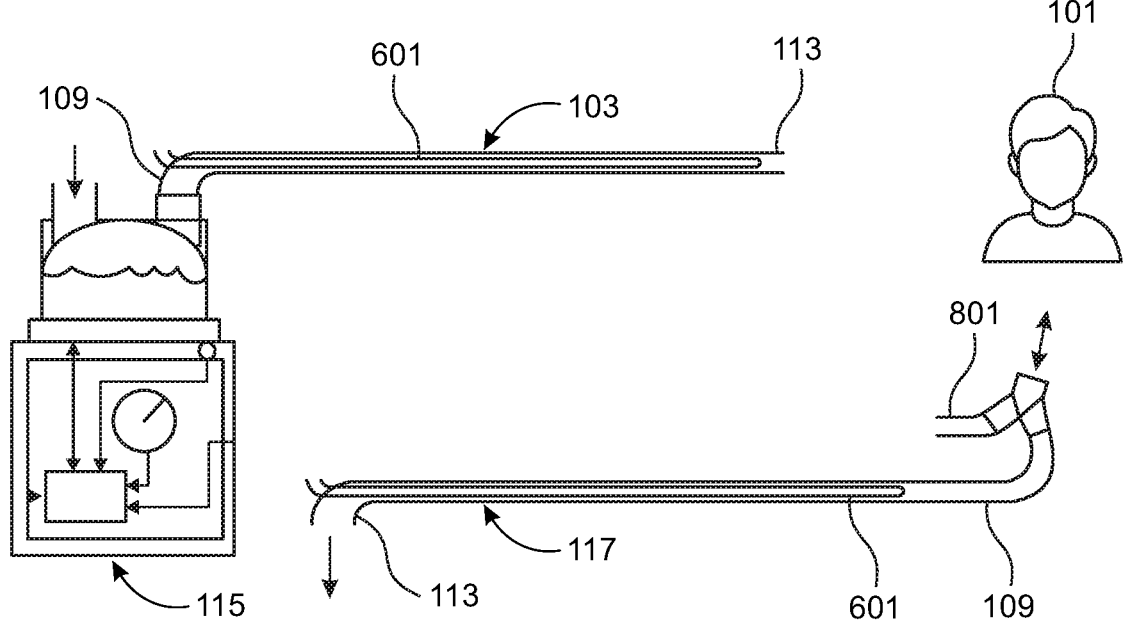
FIG. 8 is a schematic illustration of a breathing circuit including a humidifier, an inspiratory tube, and an expiratory tube.

In addition to the above, to reduce or eliminate the formation of condensation within the tube, a heater, such as a resistance heater wire, may be provided within the conduit 301 passageway, within the conduit 301 wall, or about the external surface of the outer wall surface of the conduit 301. FIG. 6 is a generalized view of the corrugated, foamed-polymer conduit 301 incorporating a heater wire 601 within the passageway of the conduit 301. FIG. 7 is a generalized view of the corrugated, foamed-polymer conduit 301 incorporating the heater wire 601 about the external surface of the outer wall surface of the conduit 301. FIG. 8 includes a schematic view of the expiratory tube 117 incorporating the heater wire 601 within the tube wall.

Additional details regarding expiratory tubes are disclosed in the specification and drawings of U.S. patent application Ser. No. 13/517,925, published as U.S. Patent Application Publication No. 2013/0098360 A1, which has been incorporated herein by reference in its entirety for all that it contains.

Reference is further made to FIG. 8, which shows a breathing circuit that comprises the inspiratory tube 103 and the expiratory tube 117. The properties of the inspiratory tube 103 and the expiratory tube 117 are similar to those described above with respect to FIG. 1 through FIG. 7. The inspiratory tube 103 has the inlet 109, communicating with the humidifier 107, and the outlet 113, through which humidified gases are provided to the patient 101. The expiratory tube 117 also has an inlet 109, which receives exhaled gases from the patient 101, and an outlet 113. As described above with respect to FIG. 1, the outlet 113 of the expiratory tube 117 can vent exhaled gases to the atmosphere, to the gases source 105, to an air scrubber/filter (not shown), or to any other suitable location.

As described above with respect to FIGS. 1, 6, and 7, the heating wires 215 can be included in the inspiratory tube 103 and/or the heating wire 601 can be included in the expiratory tube 117 to reduce the risk of condensate formation in the tubes by raising the temperature of the gases (primarily the gases near the tube wall) above the saturation temperature. It should be understood that the heating wires can desirably include coiled or helical configurations and are shown as straight lines for conceptual purposes. The breathing circuit can comprise a connector (a Y-connector or wye-piece 801) for connecting the inspiratory tube 103 and the expiratory tube 117 to a patient interface (not shown). Of course, it should be understood that other breathing circuit configurations are within the scope of the disclosure.

The foregoing description includes preferred forms of the invention. Modifications may be made thereto without departing from the scope of the invention. To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

What is claimed is:

1. A breathing circuit comprising a combination of an inspiratory tube and an expiratory tube, the breathing circuit configured for use in respiratory therapy for a patient, the breathing circuit comprising:

the inspiratory tube configured to receive an inspiratory gases flow from a gas source, the inspiratory tube comprising an inspiratory inlet, an inspiratory outlet, and a wall enclosing an inspiratory central bore, wherein the inspiratory central bore of the inspiratory tube is smooth;

the expiratory tube configured to receive an expiratory gases flow from a patient, the expiratory tube comprising an expiratory inlet, an expiratory outlet, and a wall enclosing an expiratory central bore, wherein the expiratory central bore of the expiratory tube is corrugated; and a connector that in use connects the inspiratory outlet and the expiratory inlet to a patient interface to transfer the inspiratory gases flow to the patient and the expiratory gases flow from the patient;

the inspiratory tube having an inner diameter between 9 mm and 13 mm and the expiratory tube having a nominal inner diameter between 13 mm and 19 mm.

2. The breathing circuit of claim 1, wherein the connector comprises a y piece configured for coupling the inspiratory tube and the expiratory tube.

3. The breathing circuit of claim 1, further comprising a chamber configured for holding a quantity of water and configured to be positioned on a humidifier.

4. The breathing circuit of claim 1, further comprising a dry line configured for conveying flow from the gas source to a humidifier inlet.

5. The breathing circuit of claim 1, the inspiratory tube having an inner diameter between 9 mm and 10 mm, or having an inner diameter between 11 mm and 13 mm, or having an inner diameter between 10 mm and 13 mm, or having an inner diameter between 8 mm and 13 mm.

6. The breathing circuit of claim 1, the expiratory tube having a nominal inner diameter between 13 mm and 15 mm, or having a nominal inner diameter between 13 mm and 16 mm, or having a nominal inner diameter between 14 mm and 18 mm, or having a nominal inner diameter between 16 mm and 19 mm, or having a nominal inner diameter between 14 mm and 19 mm.

7. The breathing circuit of claim 1, the inspiratory tube or expiratory tube having a length between 1.5 m and 2.5 m or having a length between 1.6 m and 2.5 m.

8. The breathing circuit of claim 1, wherein the inspiratory tube comprises a heating element within the inspiratory central bore or within the wall.

9. The breathing circuit of claim 1, wherein the expiratory tube comprises a heating element.

10. The breathing circuit of claim 1, wherein the expiratory tube is breathable.

11. The breathing circuit of claim 1, wherein the wall of the expiratory tube is permeable to water molecules and substantially impermeable to liquid and bulk flow of the expiratory gases flow flowing therethrough.

12. The breathing circuit of claim 1, wherein the inspiratory tube comprises in longitudinal cross-section a plurality of bubbles, each bubble comprising a flattened surface forming at least part of the wall of the inspiratory central bore.

13. The breathing circuit of claim 1, wherein the circuit kit breathing circuit is suitable for treatment of patients having tidal volumes in a range of 50 ml to 300 ml for pediatric patients.

14. The breathing circuit of claim 1, wherein the circuit kit breathing circuit is suitable for treatment of pediatric and adolescent patients.

15. The breathing circuit of claim 1, wherein a difference between the inner diameter of the inspiratory tube and the nominal inner diameter of the expiratory tube is between 1 mm and 10 mm.

16. The breathing circuit of claim 1, wherein at least one of the inspiratory tube and the expiratory tube comprises multiple sections to accommodate other equipment, wherein the other equipment comprises a water trap, an intermediate connector with one or more sensors, a PCB, or a controller.

17. The breathing circuit of claim 1, the inspiratory tube having an inner diameter of 11.7 mm.

18. The breathing circuit of claim 1, wherein the inspiratory gases flow received by the inspiratory tube are delivered to the patient and the expiratory gases flow received by the expiratory tube comprises at least a portion of any gases delivered to and exhaled by the patient.

19. A breathing circuit comprising a combination of an inspiratory tube and an expiratory tube, the breathing circuit configured for use in respiratory therapy for a patient, the breathing circuit comprising:

the inspiratory tube configured to receive an inspiratory gases flow from a gas source, the inspiratory tube comprising an inspiratory inlet, an inspiratory outlet, and a wall enclosing an inspiratory central bore, wherein the inspiratory central bore of the inspiratory tube is smooth;

the expiratory tube configured to receive an expiratory gases flow from a patient, the expiratory tube comprising an expiratory inlet, an expiratory outlet, and a wall enclosing an expiratory central bore, wherein the expiratory central bore of the expiratory tube is corrugated; and a connector that in use connects the inspiratory outlet and the expiratory inlet to a patient interface to transfer the inspiratory gases flow from the inspiratory tube to the patient and to transfer the expiratory gases flow from the patient to the expiratory tube;

the inspiratory tube having an inner diameter between 9 mm and 13 mm and a length, and the expiratory tube having a nominal inner diameter between 13 mm and 19 mm and a length, wherein the breathing circuit is suitable for treatment of pediatric and neonatal patients.

\* \* \* \* \*